United States Patent
Keating et al.

(10) Patent No.: US 10,194,854 B2
(45) Date of Patent: *Feb. 5, 2019

(54) METHOD FOR NON-INVASIVE MONITORING OF FLUORESCENT TRACER AGENT WITH BACKGROUND SEPARATION CORRECTIONS

(71) Applicant: MediBeacon Inc., St. Louis, MO (US)

(72) Inventors: Jennifer Keating, Mountain View, CA (US); Kimberly Shultz, Mountain View, CA (US); Kate Bechtel, Pleasant Hill, CA (US); Edward Solomon, Menlo Park, CA (US)

(73) Assignee: MediBeacon Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/884,371

(22) Filed: Jan. 30, 2018

(65) Prior Publication Data

US 2018/0214062 A1 Aug. 2, 2018

Related U.S. Application Data

(60) Provisional application No. 62/452,021, filed on Jan. 30, 2017.

(51) Int. Cl.
*A61B 5/20* (2006.01)
*G01J 1/44* (2006.01)
(Continued)

(52) U.S. Cl.
CPC ............ *A61B 5/201* (2013.01); *A61B 5/0071* (2013.01); *A61K 49/0004* (2013.01);
(Continued)

(58) Field of Classification Search
CPC .............................. A61B 5/201; A61B 5/0071
See application file for complete search history.

(56) References Cited

U.S. PATENT DOCUMENTS

| 5,591,981 A | 1/1997 | Heffelfinger et al. |
| 6,733,744 B1 | 5/2004 | Achilefu et al. |
| (Continued) | | |

OTHER PUBLICATIONS

International Search Report and Written Opinion for PCT/US2018/016053, dated Apr. 12, 2018, 9 pages.

*Primary Examiner* — Rochelle Turchen
(74) *Attorney, Agent, or Firm* — Armstrong Teasdale LLP

(57) ABSTRACT

A method of monitoring a time-varying fluorescence emitted from a fluorescent agent from within a diffuse reflecting medium with time-varying optical properties is disclosed that includes providing at least two measurements obtained from a patient before and after administration of the fluorescent agent that includes an $Flr_{meas}$ signal detected adjacent to the medium by a filtered light detector during illumination of the medium by excitatory-wavelength light, and at least one DR signal selected from: a $DR_{ex_{meas}}$, $DR_{em}$, and $DR_{em,filtered}$ signal. The method further includes identifying a post-equilibration portion of the measurement data set and transforming each $Flr_{meas}$ signal within the post-equilibration portion of the measurement data set to an $IF_{agent}$ signal representing a detected fluorescence intensity emitted solely by the fluorescent agent from within the medium. The disclosed method includes removing the effects of leak-through of excitation-level light and removing the effects of autofluorescence from the $Flr_{meas}$ signal.

16 Claims, 32 Drawing Sheets

(51) Int. Cl.
*A61B 5/00* (2006.01)
*A61K 49/00* (2006.01)
*G01J 1/04* (2006.01)
*G01J 3/10* (2006.01)
*G01J 3/28* (2006.01)
*G01J 3/44* (2006.01)
*G01J 3/02* (2006.01)
*G01N 21/64* (2006.01)
*G01N 21/47* (2006.01)

(52) U.S. Cl.
CPC ........ *A61K 49/0021* (2013.01); *G01J 1/0488* (2013.01); *G01J 1/44* (2013.01); *G01J 3/027* (2013.01); *G01J 3/10* (2013.01); *G01J 3/28* (2013.01); *G01J 3/4406* (2013.01); *G01N 21/645* (2013.01); *G01N 21/6408* (2013.01); *A61B 2560/0228* (2013.01); *G01N 21/4738* (2013.01); *G01N 2201/0625* (2013.01)

(56) References Cited

U.S. PATENT DOCUMENTS

| | | |
|---|---|---|
| 7,674,902 B2 | 3/2010 | Rajagopalan et al. |
| 2003/0017111 A1 | 1/2003 | Rabito |
| 2004/0061070 A1 | 4/2004 | Hansen |
| 2008/0076985 A1 | 3/2008 | Matousek et al. |
| 2008/0277595 A1 | 11/2008 | Lundquist et al. |
| 2009/0285761 A1* | 11/2009 | Wang .................. A61B 5/0071 424/9.6 |
| 2011/0151409 A1 | 6/2011 | Binner |
| 2013/0288912 A1 | 10/2013 | Borrebaeck et al. |
| 2017/0014065 A1 | 1/2017 | Wang et al. |

* cited by examiner

US 10,194,854 B2

METHOD FOR NON-INVASIVE MONITORING OF FLUORESCENT TRACER AGENT WITH BACKGROUND SEPARATION CORRECTIONS

CROSS-REFERENCE TO RELATED APPLICATION

This application claims the benefit of U.S. Provisional Application No. 62/452,021 filed Jan. 30, 2017, which is incorporated herein in its entirety.

BACKGROUND OF THE DISCLOSURE

The present disclosure relates generally to methods for non-invasive monitoring of a fluorescent tracer agent within a medium characterized by scattering and/or absorption of light. More particularly, the present disclosure relates to methods for non-invasive assessment of kidney function by monitoring the clearance of an exogenous fluorescent tracer within the tissues of a patient in vivo.

Dynamic monitoring of renal function in patients at the bedside in real time is highly desirable in order to minimize the risk of acute renal failure brought on by various clinical, physiological and pathological conditions. It is particularly important in the case of critically ill or injured patients because a large percentage of these patients face the risk of multiple organ failure (MOF) incited by one or more severe dysfunctions, such as: acute lung injury (ALI), adult respiratory distress syndrome (ARDS), hypermetabolism, hypotension, persistent inflammation, and/or sepsis. Renal function may also be impaired due to kidney damage associated with administration of nephrotoxic drugs as part of a procedure such as angiography, diabetes, auto-immune disease, and other dysfunctions and/or insults causally linked to kidney damage. In order to assess a patient's status and to monitor the severity and/or progression of renal function over extended periods, there exists considerable interest in developing a simple, accurate, and continuous method for the determination of renal failure, preferably by non-invasive procedures.

Serum creatinine concentration, an endogenous marker of renal function, is typically measured from a blood sample and used, in combination with patient demographic factors such as weight, age, and/or ethnicity to estimate glomerular filtration rate (GFR), one measure of renal function. However, creatinine-based assessments of renal function may be prone to inaccuracies due to many potential factors, including: age, state of hydration, renal perfusion, muscle mass, dietary intake, and many other anthropometric and clinical variables. To compensate for these variances, a series of creatinine-based equations (most recently extended to cystatin C) have been developed which incorporate factors such as sex, race and other relevant factors for the estimation of glomerular filtration rate (eGFR) based on serum creatinine measurements. However, these eGFR equations are not provided with any means of compensating for most of the above sources of variance, and therefore have relatively poor accuracy. Further, the eGFR method typically yields results that lag behind true GFR by up to 72 hrs.

Exogenous marker compounds, such as inulin, iothalamate, $^{51}$Cr-EDTA, Gd-DTPA and $^{99m}$Tc-DTPA have been used in existing methods for measuring GFR. Other endogenous markers, such as $^{123}$I and $^{125}$I labeled o-iodohippurate or $^{99m}$Tc-MAG3 have been used to in other existing methods for assessing the tubular secretion process. However, the use of typical exogenous marker compounds may be accompanied by various undesirable effects including the introduction of radioactive materials and/or ionizing radiation into the patient, and laborious ex vivo handling of blood and urine samples, rendering existing methods using these exogenous markers unsuitable for real-time monitoring of renal function at a patient's bedside.

The availability of a real-time, accurate, repeatable measure of renal excretion rate using exogenous markers under patient-specific yet potentially changing circumstances would represent a substantial improvement over any currently practiced method. Moreover, a method that depends solely on the renal elimination of an exogenous chemical entity would provide a direct and continuous pharmacokinetic measurement requiring less subjective interpretation based upon age, muscle mass, blood pressure, etc.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

Figure 1:
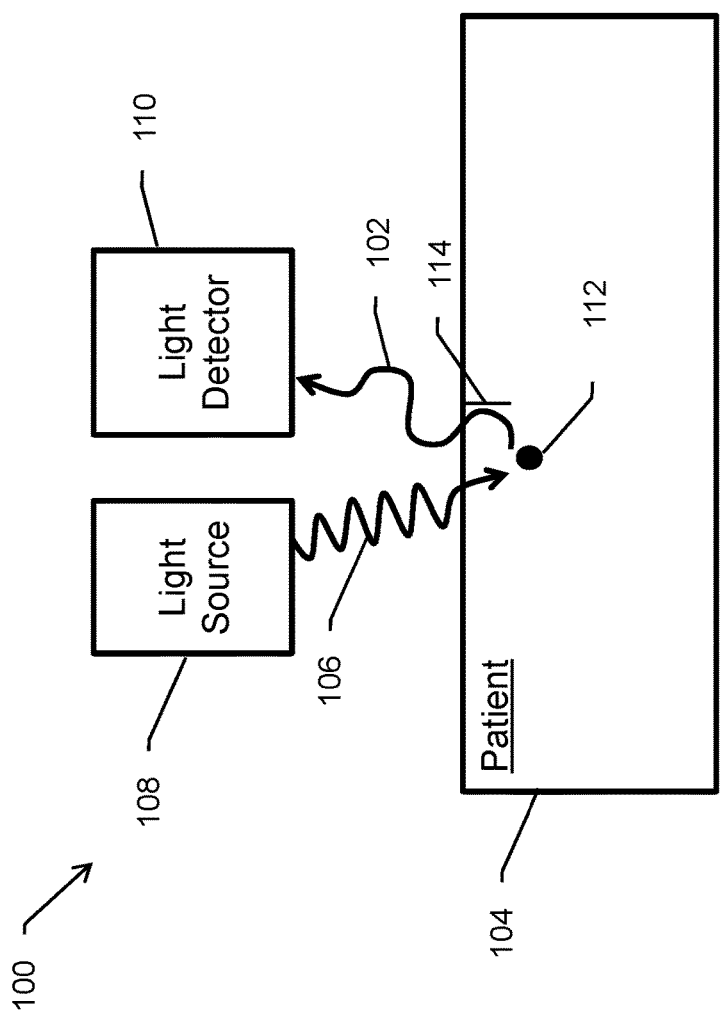
FIG. 1 is a schematic illustration of a single-wavelength renal monitoring device in one aspect.

derived from a database of 33 patients.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

A sample, as used herein, refers to a single, discrete data value acquired from a signal and/or telemetry analog-to-digital converter (ADC) for a single acquisition/telemetry channel.

A measured value, as used herein, refers to a single, discrete data value created by demodulating or accumulating a sequence of samples from one acquisition channel.

A measurement, as used herein, refers to a set comprising the Demodulated In-Phase, Demodulated Out-of-Phase, and Averaged measurement values from one acquisition channel.

A measurement subset, as used herein, refers to a set comprising all measurements for all acquisition channels during a single source LED illumination. For example, all measurements of an acquisition channel may include demodulated in-phase, demodulated out-of-phase, and averaged measurements.

A measurement set, as used herein, refers to a set comprising one measurement subset for each source LED.

An acquisition, as used herein, refers to the overall process by which a measurement set is obtained.

A measurement sequence, as used herein, refers to a sequence of one or more measurement sets.

A telemetry value, as used herein, refers to a single, discrete data value acquired from a single channel of a telemetry ADC.

A telemetry set, as used herein, refers to a set comprising one telemetry value from each telemetry channel.

A diffuse reflecting medium, as used herein, refers to any material through which light propagates, which includes a plurality of moieties, particles, or molecules that may scatter, reflect, and/or absorb the light as it propagates. The distribution of the plurality of moieties, particles, and/or molecules may be uniform or non-uniform, and may change over time.

In various aspects, systems and methods for monitoring time-varying fluorescence emitted from a fluorescent agent from within a diffuse reflecting medium with time-varying optical properties are disclosed herein below. In one aspect, systems and methods for monitoring a time-varying fluorescence emitted from an exogenous fluorescent agent within the tissues of a patient are disclosed. The systems and methods of this one aspect may be used in a variety of contexts including, but not limited to, the monitoring of renal function in vivo in a patient in real time by monitoring the decreasing fluorescence emitted by an exogenous fluorescent agent within the tissue of a patient as the exogenous fluorescent agent is eliminated by the kidneys of the patient. Although the systems and devices disclosed herein below are described in the context of methods and devices to monitor kidney function, it is to be understood that the disclosed systems and methods may be applied to any systems and methods that monitor the time-varying fluorescence emitted by a fluorescent agent from within a diffuse reflecting medium, in which the optical properties of the diffuse reflecting medium may also vary with time.

FIG. 1 is a schematic illustration of a system 100, provided as a non-limiting example, in which fluorescence 102 with an emission wavelength ($\lambda_{em}$) is detected from a region of interest of a patient 104 using a light detector 110 configured to detect only those photons with an emission wavelength ($\lambda_{em}$). In general, the exogenous fluorescent agent 112 produces fluorescence 102 in response to an excitation event including, but not limited to: illumination by light 106 at an excitation wavelength ($\lambda_{ex}$), occurrence of an enzymatic reaction, changes in local electrical potential, and any other known excitation event associated with exogenous fluorescent agents. In an aspect, the system 100 may include a light source 108 configured to deliver light 106 at an excitation wavelength ($\lambda_{ex}$) to the patient 104. In this aspect, the fluorescence 102 is produced in response to illumination by the light 106. In addition, the excitation wavelength ($\lambda_{ex}$) of the light 106 and the emission wavelength ($\lambda_{em}$) of the fluorescence 102 are spectrally distinct (i.e., $\lambda_{ex}$ is sufficiently different from $\lambda_{em}$) so that the light detector 110 may be configured to selectively detect only the fluorescence 102 by the inclusion of any known optical wavelength separation device including, but not limited to, an optical filter.

In some aspects, changes in the fluorescence 102 may be monitored to obtain information regarding a physiological function or status of the patient. By way of non-limiting example, the time-dependent decrease in the fluorescence 102 measured after introduction of the exogenous fluorescent agent 112 into a circulatory vessel of the patient 104 may be analyzed to obtain information regarding renal function of the patient 104. In this non-limiting example, the rate of decrease in fluorescence 102 may be assumed to be proportional to the rate of removal of the exogenous fluorescent agent 112 by the kidneys of the patient 104, thereby providing a measurement of renal function including, but not limited to: renal decay time constant (RDTC) and glomerular filtration rate (GFR).

Without being limited to any particular theory, the intensity of fluorescence 102 detected by the light detector 110 may be influenced by any one or more of numerous factors including, but not limited to: the intensity or power of the light 106 at $\lambda_{ex}$ delivered to the patient 104, the scattering and absorption of the light 106 passing through intervening tissues 114 of the patient 104 between the light source 108 and the exogenous fluorescent agents 112, the concentration of exogenous fluorescent agents 112 illuminated by the light 106, the scattering and absorption of the fluorescence 102 at $\lambda_{em}$ passing through intervening tissues 114 of the patient 104 between the exogenous fluorescent agents 112 and the light detector 110, leak-through of the excitation light 106 through any optical filters configured to transmit only light at emission wavelength $\lambda_{em}$, and fluorescence emitted by endogenous skin components.

Figure 14:
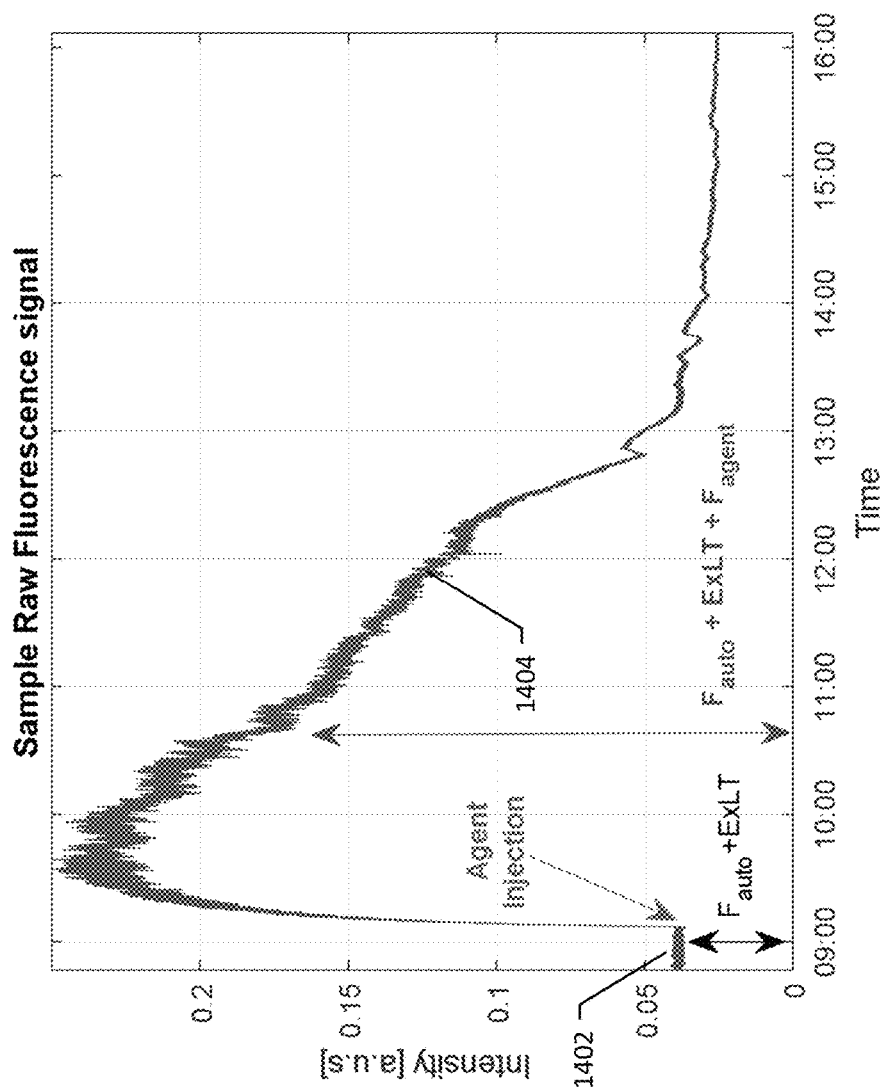
FIG. 14 is a graph of raw fluorescence signal as a function of time illustrating various phenomenon contributing to the total signal.

FIG. 14 is a graph showing a representative time history of a raw fluorescence signal obtained at the emission wavelength $\lambda_{em}$ corresponding to the wavelength of fluorescence emitted by an endogenous fluorescent agent within the tissues of a patient in response to illumination by excitation-wavelength light. The measured raw fluorescence signal obtained prior to the injection of the endogenous fluorescence agent (i.e. the background signal 1402) may include autofluorescence ($F_{auto}$) emitted by endogenous structures as well as leak-through of excitation-wavelength light (ExLT) through any optical filters configured to transmit only emission-wavelength light to the light detector producing the raw fluorescence signal. The measured raw fluorescence signal obtained after the injection of the endogenous fluorescent agent (i.e. $Flr_{meas}$ 1404) may include the intensity of the fluorescence emitted by the endogenous fluorescent agent ($F_{agent}$) superimposed over the background signal 1402 (i.e. $F_{auto}$ and ExLT).

Existing methods typically assume that the optical properties within the intervening tissue 114 remain essentially unchanged throughout the period during which measurements are obtained by the system 100. As a result, existing methods typically obtain initial measurements through the intervening tissue 114 of the patient 104 prior to introduction of the exogenous fluorescent agent 112, and these initial measurements are subtracted to correct all subsequent data obtained after introduction of the exogenous fluorescent agent 112. However, during long-term monitoring of the patient 104, changes in the optical properties of the intervening tissue 114 may occur due to changes in at least one characteristic including, but not limited to: optical coupling efficiency of the light detector 110 to the patient 104; concentration of chromophores such as hemoglobin due to changes in blood volume caused by vascular dilation, constriction, or compression; changes in the optical properties of chromophores such as hemoglobin due to changes in oxygenation status; and changes in tissue structure such as changes related to edema.

Figure 16:
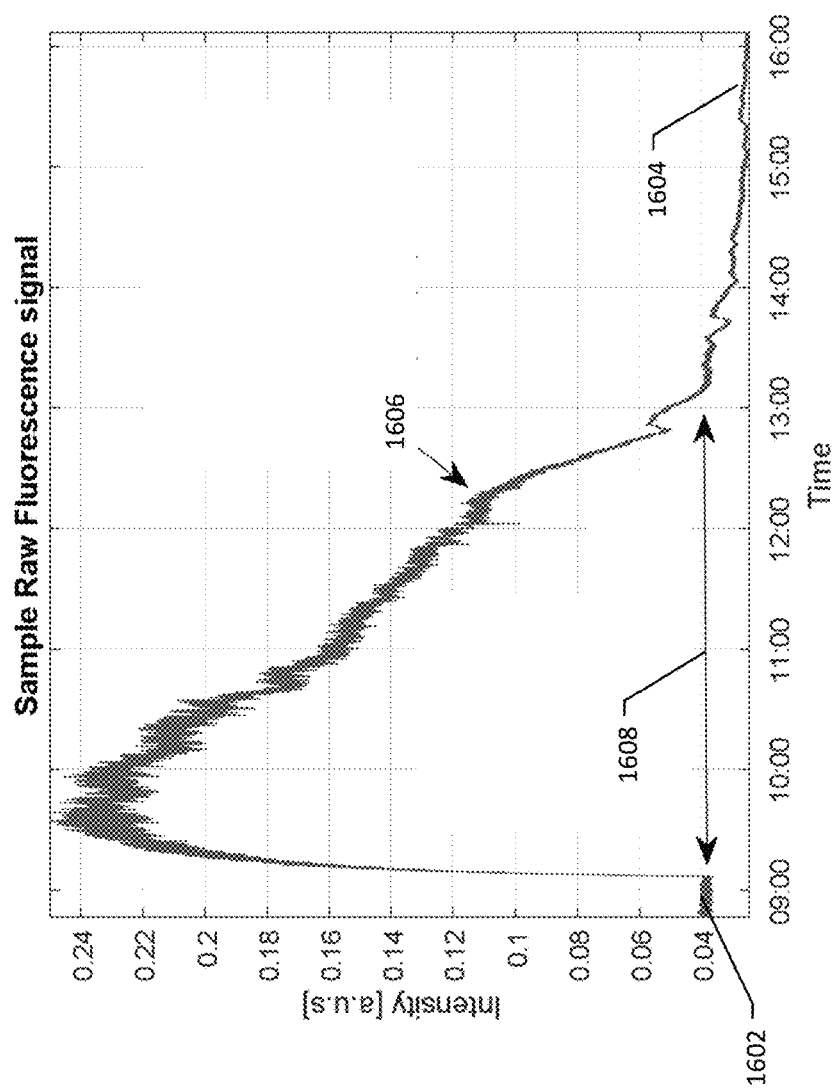
FIG. 16 is a graph of raw fluorescence signal as a function of time in which the final fluorescence signal falls below the original background fluorescence signal level due to various phenomena contributing to the total signal.

FIG. 16 is a graph of the raw fluorescence signal measured before and after the injection of an endogenous fluorescent agent, illustrating that the background signal may change over the extending data acquisition period associated with the renal clearance of the endogenous fluorescent agent from the patient. As illustrated in FIG. 16, the initial background signal level 1602 is about 0.01 intensity units higher than the final background signal level 1604 measured about nine hours after the measurement of the initial background signal level 1602. Without being limited to any particular theory, it is thought the administration of a blood pressure medication during the data acquisition period may have induced skin flushing and associated vasodilation of skin capillaries that may have altered the optical properties of the patient's skin, due to the increased concentration of blood, which contains hemoglobin, an known endogenous chromophore capable of absorbing light at both the excitation and emission wavelengths.

These dynamic changes in the optical properties of the intervening tissue 114 may introduce uncertainty into long-term measurements of fluorescence 102. By way of non-limiting example, changes in the optical properties of the intervening tissue 114 may modulate the intensity or power of the light 106 illuminating the exogenous fluorescent agents 112, causing a modulation of the fluorescence 102 produced by the exogenous fluorescent agents 112 that may be erroneously interpreted as a modulation in the concentration of the exogenous fluorescent agents 112. By way of another non-limiting example, changes in the optical properties of the intervening tissue 114 may modulate the intensity or power of the fluorescence 102 reaching the light detector 110 that may also be erroneously interpreted as a modulation in the concentration of the exogenous fluorescent agents 112. The potential modulation of changes in the optical properties of the intervening tissue 114 may introduce uncertainty into measurements of fluorescence 102, in particular those measurements associated with long-term monitoring of fluorescence 102 as described herein above.

Similarly, because autofluorescence ($F_{auto}$) produced by endogenous chromophores occurs in a similar manner to the fluorescence produced by the exogenous fluorescent agent, dynamic changes in the optical properties of the intervening tissue may introduce variability in the autofluorescence ($F_{auto}$) levels over the course of long-term measurements of fluorescence 102. By way of non-limiting example, changes in the scattering and absorption of the light 106 passing through the intervening tissue 114 may modulate the intensity or power of the light 106 illuminating the endogenous chromophores, causing a modulation of the autofluorescence that may modulate the background fluorescence over the course of data acquisition. By way of another non-limiting example, changes in the scattering and absorption of the autofluorescence passing through the intervening tissue 114 may modulate the intensity of the autofluorescence detected by the light detector 110 that may modulate the background fluorescence over the course of data acquisition. The potential modulation of background fluorescence, if not properly accounted for, may introduce uncertainty into raw fluorescence measurements and by extension may introduce uncertainty into parameters derived from an analysis of these florescence measurements.

Figure 15:
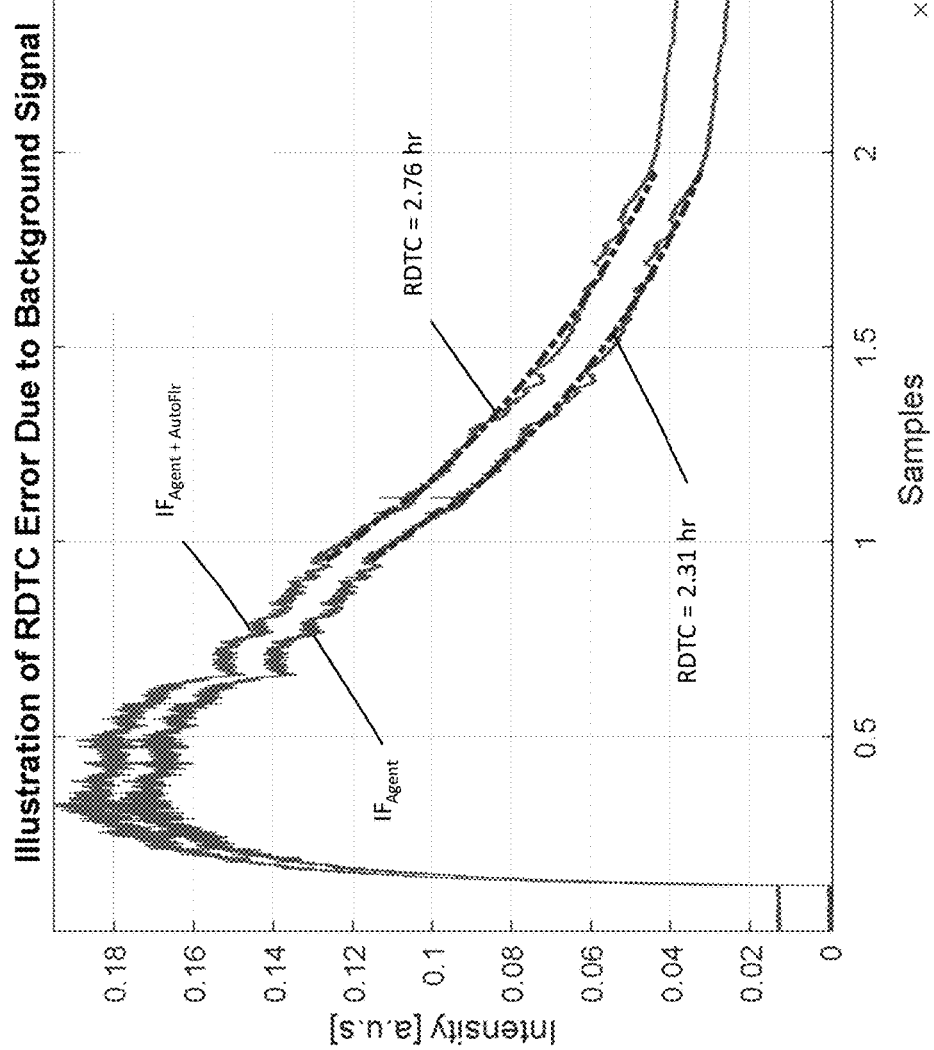
FIG. 15 is a graph of intrinsic fluorescence signals, with and without an autofluorescence correction, as a function of time illustrating the effect of an autofluorescence correction on the renal decay time constants (RDTC) derived from analysis of the intrinsic fluorescence signal.

By way of non-limiting example, changes in autofluorescence related to dynamic changes in the optical properties of the skin of the patient may introduce uncertainty into the calculation of renal decay time constant (RDTC), a measure of renal function as described herein below. FIG. 15 is a graph of a raw fluorescence signal measured before and after the injection of an endogenous fluorescent agent that includes autofluorescence ($IF_{Agent+AutoFlr}$, blue line). The graph of FIG. 15 also includes a corrected fluorescence signal ($IF_{Agent}$, green line) calculated by removing the effects of autofluorescence from the raw fluorescence signal using the methods described herein below. Superimposed on each signal are curve-fits associated with the calculation of RDTC. As shown in FIG. 15, the RDTC value of 2.76 hr. calculated using the raw fluorescence signal is considerably higher that the corresponding RDTC value of 2.31 hr. calculated using the corrected fluorescence signal.

In various aspects, a method of correcting in vivo real-time measurements of fluorescence from an exogenous fluorescent agent to remove the effects of changes in the optical properties within the tissue of the patient is provided. The inclusion of an additional measurement of light passing through the tissue of the patient via a separate optical pathway (i.e. diffuse reflectance) from the optical pathway of the fluorescence measurements enhanced the quantification of changes in the optical properties of the tissue during prolonged monitoring of fluorescence from an exogenous fluorescent agent within a patient. The inclusion of this additional measurement in the correction method in various aspects was discovered to significantly enhance the fidelity of fluorescence measurements.

Detailed descriptions of devices for monitoring the fluorescence of an exogenous fluorescent agent in vivo and methods of correcting the fluorescence measurements to remove the effects of changes in the background signal are provided herein below.

Although the devices and methods are described herein below in the context of a non-invasive optical renal function monitor, it is to be understood that the correction method described herein, with appropriate modification, may be applied to any compatible device configured to perform measurements by delivering EM radiation from an external source through any scattering medium and/or receiving EM radiation propagated through any scattering medium to an external detector. Non-limiting examples of EM radiation include visible light, near-IR light, IR light, UV radiation, and microwave radiation. The scattering media may include any living or non-living material capable of propagating EM radiation of at least one EM frequency without limitation. At least a portion of the scattering media may further include one or more substructures or compounds capable of reflecting and/or absorbing the EM radiation. Non-limiting examples of scattering media include: a tissue of a living or dead organism, such as a skin of a mammal; a gas such as air with or without additional particles such as dust, fluid droplets, or a solid particulate material; a fluid such as water with or without additional particles such as gas bubbles or a solid particulate material. Further, the devices and methods described herein below are not limited to detection of renal function, but may be modified for use in the detection of the function of other physiological systems including, but not limited to, liver systems, or gastro-intestinal systems.

System Description

Figure 2:
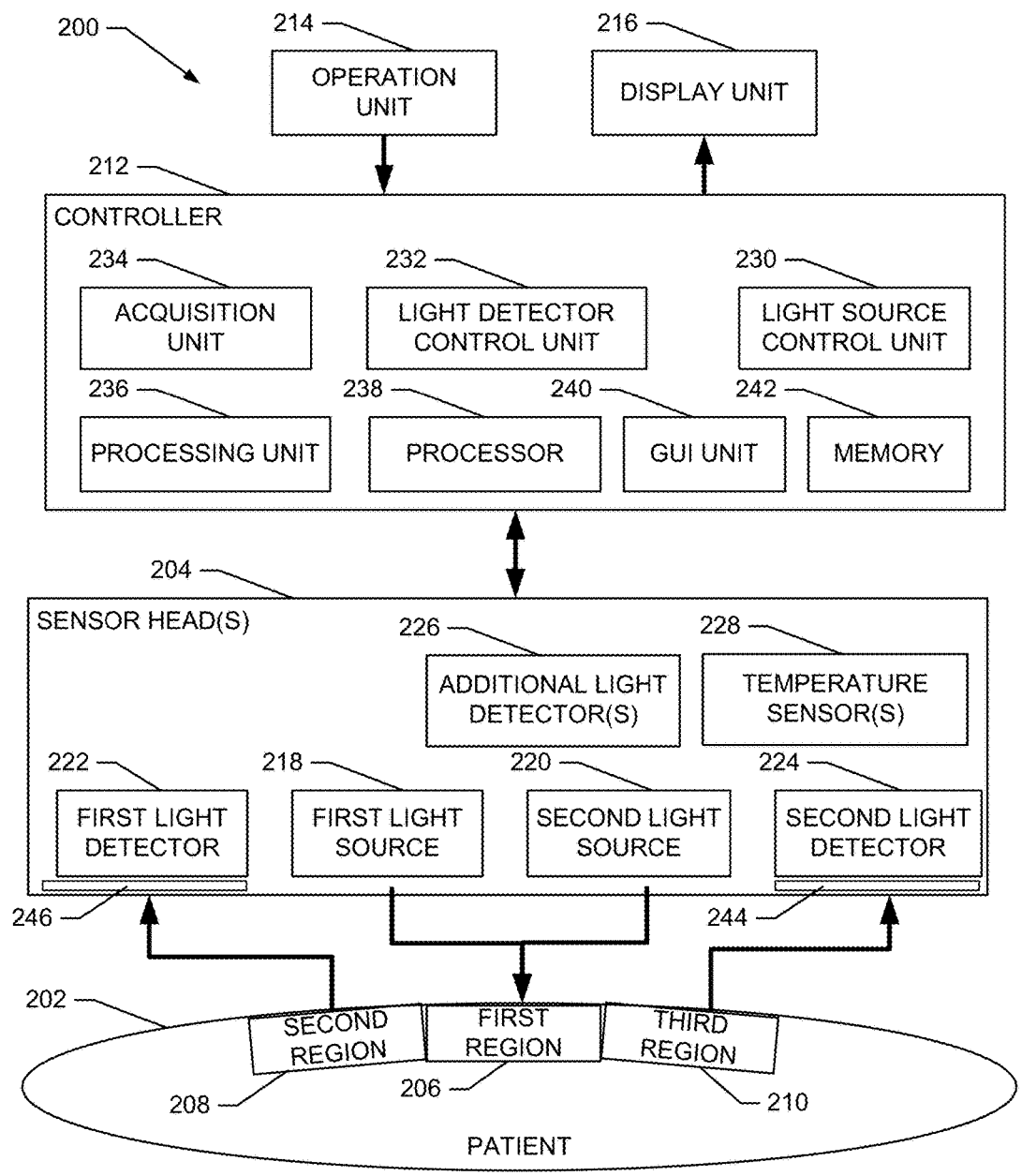
FIG. 2 is a schematic illustration of a dual-wavelength renal monitoring system in one aspect.

In various aspects, the methods of correcting fluorescence measurements to remove the effects of variations in local skin properties as disclosed herein may be incorporated into any fluorescence monitoring system including, but not limited to, a system for optically monitoring renal function in vivo and in real time by measuring changes in fluorescence of an exogenous fluorescent agent injected into a patient as the agent is renally eliminated from the patient. FIG. 2 is a block diagram of a system 200 for optically monitoring renal function of a patient 202 via measurements of the fluorescence of an injected exogenous fluorescent agent in the patient 202, in one aspect. The system 200 may include at least one sensor head 204 configured to deliver light at an excitatory wavelength ($\lambda_{ex}$) into a first region 206 of the patient 202. The system 200 is further configured to detect light at an emission wavelength ($\lambda_{em}$), at a second region 208 of the patient 202, and to detect light at the excitatory wavelength ($\lambda_{ex}$), and/or emission wavelength ($\lambda_{em}$), at a third region 210 of the patient 202.

The system 200 may further include a controller 212 operatively coupled to the at least one sensor head 204, an operation unit 214, and a display unit 216. In various aspects, the controller 212 is configured to control the operation of the at least one sensor head 204 as described in additional detail herein below. The controller 212 is further configured to receive measurements of light from the at least one sensor head 204. The controller 212 is further configured to correct the light measurements corresponding to fluorescence from exogenous fluorescent agents according to at least one method including, but not limited to, the disclosed methods of correcting fluorescence measurements using measurements indicative of dynamic changes in the background signal related to changes in autofluorescence and/or the leak-through of excitatory-wavelength light to the second light detector 224 configured to detect emission-wavelength light only. The controller 212 is further configured to transform the fluorescence measurements received from the at least one sensor head 204 into a summary parameter representative of the renal function of the patient 202. In addition, the controller 212 is configured to receive at least one signal representing user inputs from the operation unit 214 and to generate one or more forms for display on the display unit 216 including, but not limited to, a graphical user interface (GUI).

A detailed description of the sensor head 204 and controller 212 are provided herein below.

A. Sensor Head

Figure 6:
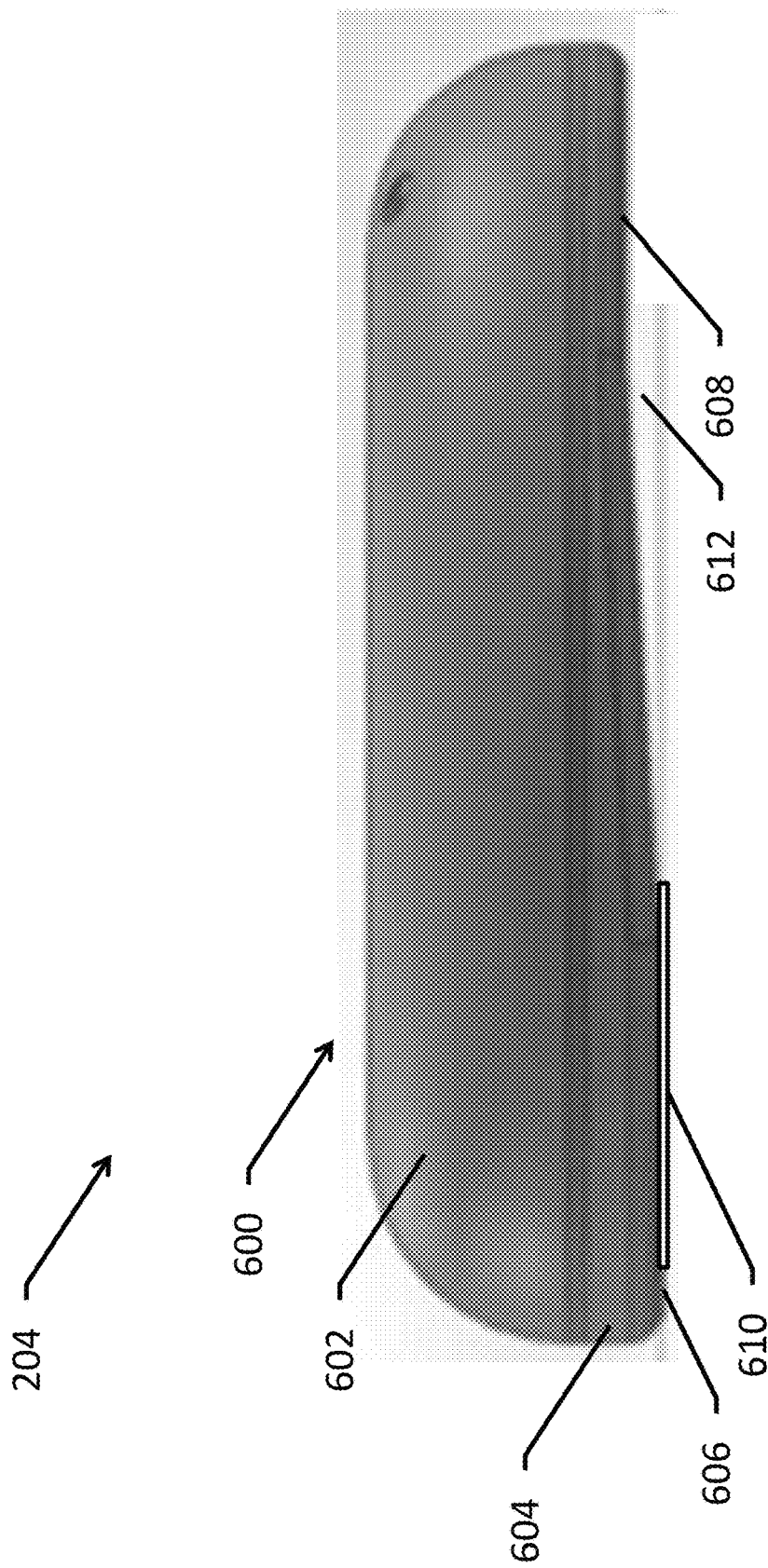
FIG. 6 is a side view of a sensor head of a renal function monitoring system in one aspect.

In various aspects, the sensor head 204 includes at least one light source and at least one light detector in a housing. FIG. 6 is a side view of a housing 600 for the sensor head 204 in one aspect that includes an upper housing 602 and a lower housing 604 attached together to enclose two light sources and two light detectors. The bottom surface 608 of the lower housing 604 further includes a contact surface 606 configured to be attached to the skin of a patient 202 using a biocompatible adhesive material including, but not limited to, a surgical adhesive. In use, the surface of the adhesive material opposite to the contact surface 606 may be affixed to the skin of the patient 202. In various aspects, the adhesive material may be configured to transmit light through the light sources into the patient and to further transmit the fluorescence from the patient to the light detectors. In one aspect, the adhesive material may be an optically transparent material. In another aspect, the adhesive material may be produced from a non-fluorescing material to prevent the production of confounding fluorescence by the adhesive material.

In various other aspects, the upper housing 602 may further include one or more openings 806 configured to provide access to the interior for a cable including, but not limited to, a USB cable, and/or to provide a window for a display generated by the circuitry contained within the housing 600, such as an indicator LED.

Figure 7:
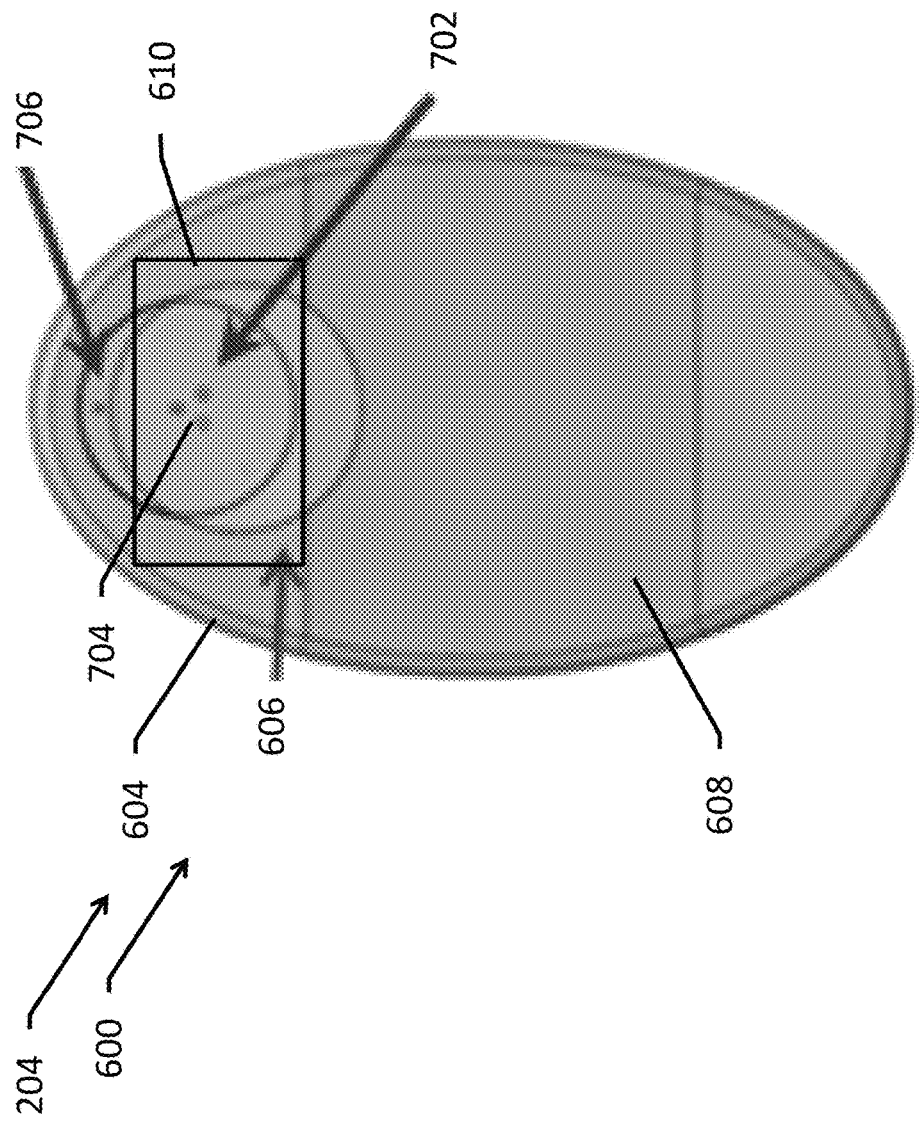
FIG. 7 is a bottom view of the sensor head of FIG. 6.
Figure 8:
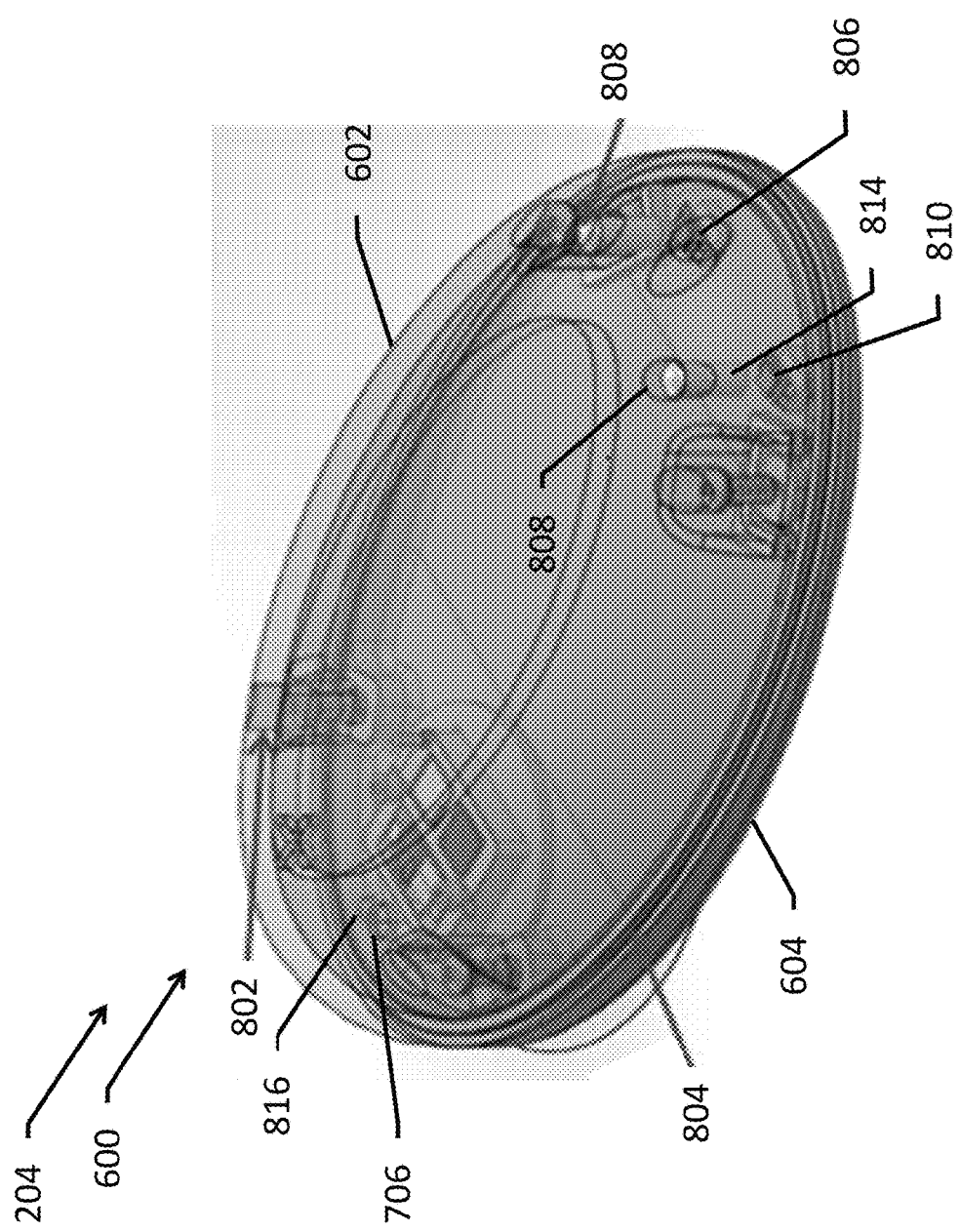
FIG. 8 is a top interior view of the sensor head of FIG. 6 illustrating an arrangement of various electrical components within a housing of a sensor head of a renal function monitoring system in one aspect.

FIG. 7 is a bottom view of the housing 600 illustrated in FIG. 8. The contact surface 606 may include an aperture plate 702 including one or more apertures 704 configured to transmit light between the skin of the patient and the light sources and light detectors contained inside the housing 600. In one aspect, the aperture plate 702 may be epoxied into the lower housing 604 to prevent liquid ingress into the interior of the housing 600. In various aspects, the dimensions, arrangement, and/or spacing of the one or more apertures 704 may be selected to enhance various aspects of the operation of the system 200, as described in additional detail herein below. In another aspect, the contact surface 606 may further include a temperature sensor opening 706 configured to provide a thermal path from the skin surface of the patient to an additional temperature sensor 228 configured to monitor the temperature at the skin surface of the patient.

FIG. 8 is a schematic diagram illustrating the arrangement of the electrical components within the housing 600. Referring to FIG. 8, the upper housing 602 and the lower housing 604 may be affixed together with screws 802, and the screw holes and the interface between the two housing pieces may be filled with a water-resistant filler material 804 including, but not limited to, a silicone material such as room temperature vulcanization silicone (RTV) to inhibit liquid ingress into the interior of the housing 600.

In an aspect, the housing 600 may further include a cable opening 806 formed through the upper housing 602. The cable opening 806 may be configured to provide access to the interior for an electrical cable including, but not limited to, a USB cable. In one aspect, the cable may enable the supply of power to the light sources, light detectors, indicator lights, and associated electrical devices and circuits as described herein below. In another aspect, the cable may further enable the communication of control signals into the housing to enable the operation of the electrical components within the housing 600, and the cable may further enable the communication of data signals encoding measurements obtained by one of more of the sensor devices contained within the housing 600 including, but not limited to: the first light detector 222, the second light detector 224, any additional light detectors, such as a first monitor photodiode 904 and a second monitor diode 906, and any additional temperature sensors 228 (see FIG. 9). In an aspect, the cable may be attached to the cable opening 806 and adjacent upper housing 602 with a light absorbent adhesive including, but not limited to, black epoxy and may further be sealed against water incursion using a water resistant filler material including, but not limited to, RTV.

In an additional aspect, the housing 600 may further include at least one display opening 808 formed through the upper housing 602. In one aspect, each display opening 808 may be configured to provide a window for a display generated by the circuitry contained within the housing 600, such as an indicator LED 810. In an aspect, each indicator LED 810 may be positioned on a circuit board 812. In an aspect, a light pipe 814 may be epoxied into the display opening 808 within the upper housing 602 above each indicator LED 810. Each a light pipe 814 may be filled with a water-resistant filler material such as RTV for liquid ingress protection. In various aspects, the at least one indicator LED 810 may illuminate in a predetermined pattern to enable a user of the system 200 to monitor the operational status of the sensor head 204.

Figure 9:
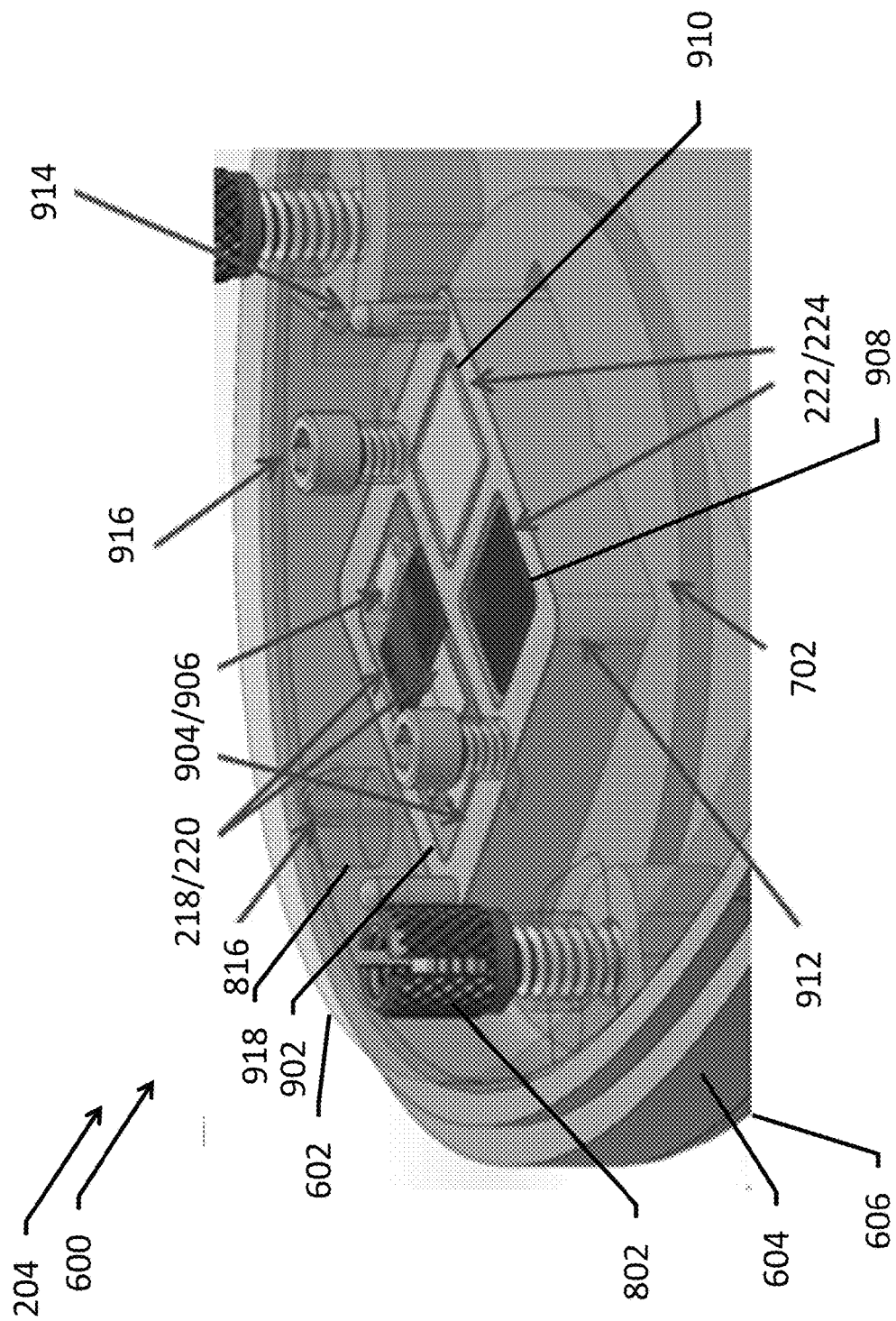
FIG. 9 is an enlargement of the interior view of FIG. 8.

FIG. 9 is a close-up view of the interior optical region of the sensor head 204 showing the arrangement of the light sources 218/220 and the light detectors 222/224 within the housing 600 in one aspect. In an aspect, the light sources 218/220 are separated from the light detectors 222/224, and the first light detector 222 is separated from the second light detector 224 are separated from one another by a sensor mount 912 affixed to the aperture plate 702. In an aspect, the sensor mount 912 ensures that light from the light sources 218/220 does not reach the light detectors 222/224 without coupling through the skin of the patient 202. The separation between the first light detector 222 within the first detection well 908 and the second light detector 224 within the second detection well 910 ensures that the fluorescence signal produced by the exogenous fluorescent agent within the tissues of the patient 202 is distinguishable from the unfiltered excitation light introduced by the first light source 218.

Referring again to FIG. 9, the sensor mount 912 may be aligned to a circuit board (not shown) containing the light sources 218/220 and light detectors 222/224 using alignment pins 914 and held in place using screws 916. In an aspect, the sensor mount 912 may be affixed to the circuit board containing the light sources 218/220 and light detectors 222/224 using a light absorbent adhesive including, but not limited to, black epoxy. In this aspect, this light-resistant join between the circuit board and the sensor mount 912 inhibits leakage of light between the light sources 218/220 and the light detectors 222/224, and further inhibits the leakage of light between the first light detector 222 and the second light detector 224. The apertures 704 configured to transmit light to and from the skin underlying the contact surface 606 of the sensor head 204 are formed through a structurally separate aperture plate 702 (see FIG. 7) to provide for precise alignment of the apertures 704 to the corresponding light sources 218/220 and light detectors 222/224, described in additional detail herein below.

In various aspects, the sensor mount 912 may further provide electrical shielding for any sensitive electrical devices within the sensor head 204 including, but not limited to, the light detectors 222/224. In one aspect, the sensor mount 912 may be constructed of an electrically conductive material including, but not limited to: aluminum and aluminum alloy. In this aspect, the sensor mount 912 may be electrically coupled to the ground of the circuit board using conductive screws 916. In addition, any glass windows positioned within the source well 902 and/or detector wells 908/910 adjacent to the aperture plate 702 including, but not limited to, an optical filter 244 and clear glass 246 as described herein below (see FIG. 2) may further include an electrically conductive coating. Non-limiting examples of suitable electrically conductive coatings for the glass windows of the sensor mount include a conductive indium tin oxide (ITO) coating and any other suitable transparent and electrically conductive coating.

Without being limited to any particular theory, the conductive material of the sensor mount 912 provides a partial Faraday cage to shield the electrically sensitive detectors 222/224 from electrical noise generated by or conducted through the patient's body. The partial Faraday cage provided by the sensor mount 912 may be completed with the conductive ITO coating on the glass windows within the source well 902 and/or detector wells 908/910. In an aspect, the electrically conductive coating on the glass windows, such as an ITO coating, are sufficiently conductive to provide electrical shielding while remaining sufficiently transparent for the transmission of light to and from the skin surface of the patient 202. In another aspect, the ITO coating of each glass window may be grounded to an electrically conductive sensor mount 912 using any known electrical grounding method including, by not limited to: a wire connecting the glass coating to the sensor mount 912 that is attached at both wire ends with conductive epoxy, or attaching the coated glass directly to a glass fitting such as a ledge or frame formed within each of the source well 902 and/or detector wells 908/910 using an electrically conductive epoxy.

In various aspects, the contact surface 606 of the housing 600 may be attached the patient's skin using a biocompatible and an adhesive material 610 including, but not limited to, a clear double-sided medical grade adhesive, as illustrated in FIG. 6 and FIG. 7. Any adhesive material selected to be optically transmissive at the excitation and emission wavelengths used by the system 100 as described herein. The adhesive material 610 may be positioned on the contact surface 606 such that the adhesive material covers the apertures 704, but exposes the temperature sensor opening 706 to ensure sufficient thermal contact with the skin of the patient 202. In one aspect, the sensor head 204 may be further secured to the patient 202 as needed using one or more additional biocompatible medical fastener devices including, but not limited to: Tegaderm bandages, medical tape, or any other suitable biocompatible medical fastener devices.

In an aspect, the contact surface 606 may be located near the front edge of the sensor head 204 to provide for accurate positioning of the contact surface 606 on a selected region of the patient's skin. In another aspect, the apertures 704 may be positioned towards the center of the contact surface 606 to reduce ambient light ingress. Without being limited to any particular theory, ambient light may enter one or more of the apertures 704 due to incomplete adhesion of the contact surface 606 to the patient's skin and/or due to the propagation of ambient light passing through the patient's exposed skin situated just outside of the footprint of the contact surface 606 into the apertures 704.

Referring again to FIG. 6, the bottom surface 608 of the sensor head 204 curves away from the plane of the contact surface 606 to enable attachment of the sensor head 204 to varied body type and locations. For attachment of the sensor head 204 to relatively flat or concave surfaces, any gap 612 between the bottom surface 608 and the skin surface of the patient 202 may be filled with a biocompatible foam to ensure consistent contact with the patient 202.

i) Light Sources

In various aspects, each sensor head 204 includes a first light source 218 and a second light source 220 configured to deliver light to a first region 206 of a patient 202. The first light source 218 is configured to deliver the light at the excitatory wavelength and the second light source 220 is configured to deliver light at the emission wavelength. In one aspect, the excitatory wavelength may be selected to fall within a spectral range at which the exogenous fluorescent agent exhibits relatively high absorbance. In another aspect, the emission wavelength may be selected to fall within a spectral range at which the exogenous fluorescent agent exhibits relatively high emission. The exogenous fluorescent agent may be selected for enhanced contrast relative to other chromophores within the tissues of the patient 202 including, but not limited to hemoglobin within red blood cells and/or melanin within melanocytes. In various aspects, the exogenous fluorescent agent may be selected to conduct measurements within spectral ranges with lower variation in absorption by other chromophores such as hemoglobin within the tissues of the patient 202 during use.

Without being limited to any particular theory, hemoglobin (Hb) is an absorber of visible light in the tissues of the patient 202, and has the potential to interfere with the measurements of fluorescence of the exogenous fluorescent agent if the Hb absorbance varies over the measurement period of the system 200. Because hemoglobin (Hb) enables gas exchange within virtually all tissues containing circulatory vessels, virtually all tissues are vulnerable to interference with fluorescence measurements of the system 200 due to fluctuations in hemoglobin concentration. Within most tissues, externally applied pressure may cause blood pooling which may be manifested as an apparent decay of the fluorescence measured at the skin surface. Periodic opening and closing of blood vessels ("vasomotion") near the surface of the skin may also cause fluctuations in hemoglobin concentration which may introduce additional noise in to measurements of fluorescence of the exogenous fluorescent agent by the system 200. Further, in some patients 202, such as those with pulmonary disorders, variation in the Hb oxygenation state may also be observed, leading to additional potential variations in the background skin absorbance due to differences in the absorption spectra of deoxyhemoglobin (Hb) and oxyhemoglobin ($HbO_2$), shown illustrated in FIG. 3.

In an aspect, the excitation and emission wavelengths for the exogenous fluorescent agent may be selected to coincide with a pair of $HbO_2$/Hb isosbestic points, each isosbestic point defined herein as a wavelength characterized by about equal light absorbance by $HbO_2$ and Hb. Without being limited to any particular theory, fluorescence measurements conducted at each isosbestic wavelength are less sensitive to variation due to changes in the oxygenation of hemoglobin, so long as the combined concentration of $HbO_2$ and Hb remains relatively stable during measurements of fluorescence by the system 200. Non-limiting examples of Hb/$HbO_2$ isosbestic wavelengths include: about 390 nm, about 422 nm, about 452 nm, about 500 nm, about 530 nm, about 538 nm, about 545 nm, about 570 nm, about 584 nm, about 617 nm, about 621 nm, about 653 nm, and about 805 nm.

Figure 4:
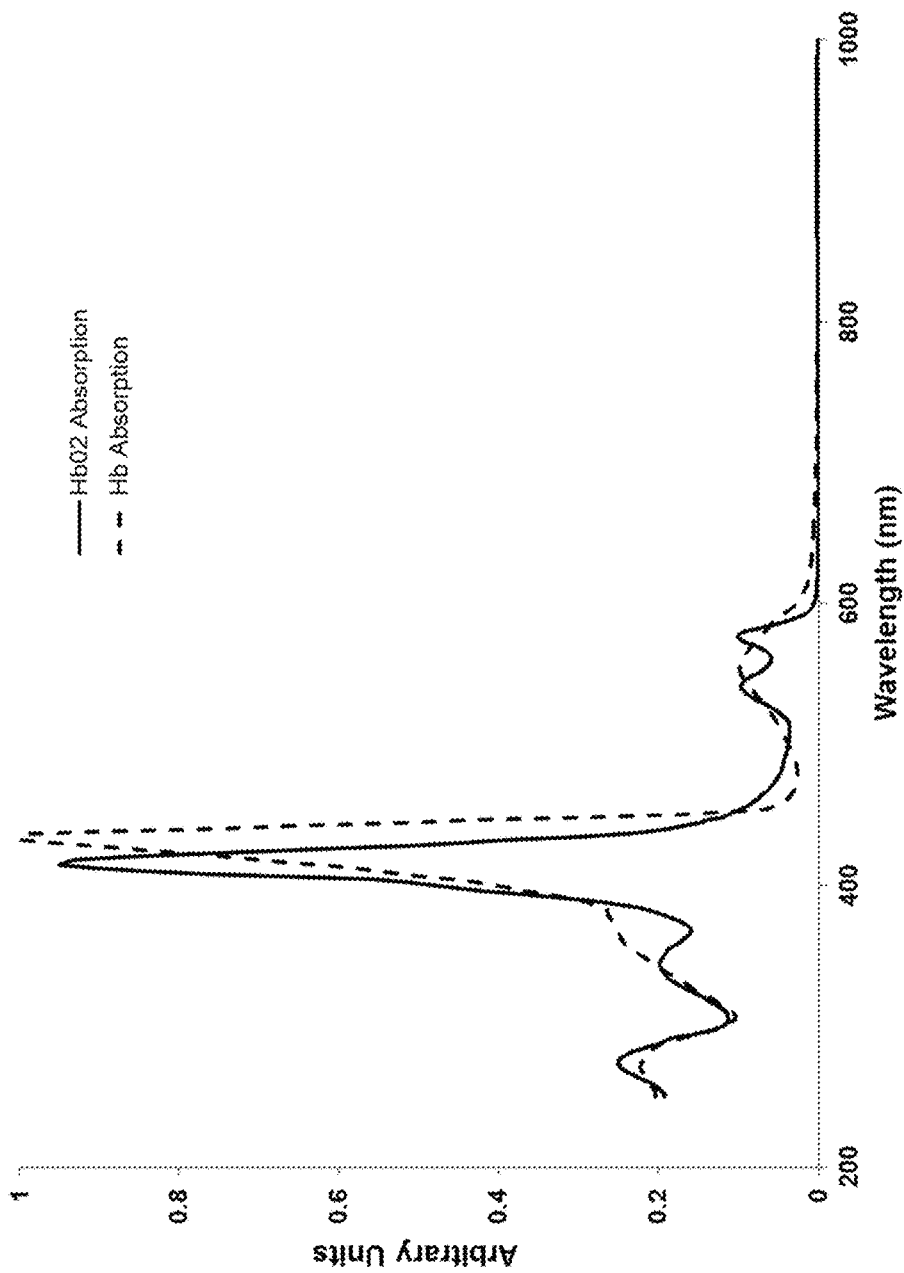
FIG. 4 is a graph summarizing the absorption spectra of oxyhemoglobin (HbO$_2$) and deoxyhemoglobin (Hb) defined over light wavelengths ranging from about 200 nm to about 650 nm.

In various aspects, the excitation and emission wavelengths may be selected based on the absorption and emission wavelengths of the selected exogenous fluorescent agent of the system 200. In one aspect, the excitatory wavelength may be an $HbO_2$/Hb isosbestic wavelength and simultaneously may be a wavelength within a spectral range of high absorbance of the exogenous fluorescent agent. In another aspect, the emission wavelength may be an $HbO_2$/Hb isosbestic wavelength and simultaneously may be a wavelength within a spectral range of emission by the exogenous fluorescent agent. Table 1 provides a summary of $HbO_2$/Hb isosbestic wavelengths within the spectral range of 200 nm to about 1000 nm. FIG. 4 is a graph of the absorption spectra used to identify the $HbO_2$/Hb isosbestic wavelengths of Table 1.

TABLE 1

$HbO_2$/Hb Isosbestic Wavelengths $\lambda$ = 200-1000 nm

| Excitation Wavelength (nm) | Hb Molar Extinct. Coeff. ($M^{-1}$ $cm^{-1}$) | $HbO_2$ dA/d$\lambda$ ($M^{-1}$ $cm^{-1}$ $nm^{-1}$) | Hb dA/d$\lambda$ ($M^{-1}$ $cm^{-1}$ $nm^{-1}$) |
| --- | --- | --- | --- |
| 260 | $1.2 \times 10^5$ | $1.8 \times 10^3$ | $6.3 \times 10^2$ |
| 288 | $1.1 \times 10^5$ | $-2.9 \times 10^3$ | $-3.4 \times 10^3$ |
| 298 | $7.0 \times 10^4$ | $-3.3 \times 10^3$ | $-3.2 \times 10^3$ |
| 314 | $6.5 \times 10^4$ | $1.6 \times 10^3$ | $1.5 \times 10^3$ |
| 324 | $8.2 \times 10^4$ | $1.9 \times 10^3$ | $1.8 \times 10^3$ |
| 340 | $1.1 \times 10^5$ | $6.5 \times 10^2$ | $1.6 \times 10^3$ |
| 390 | $1.7 \times 10^5$ | $1.0 \times 10^4$ | $5.1 \times 10^3$ |
| 422 | $4.3 \times 10^5$ | $-2.6 \times 10^4$ | $1.3 \times 10^4$ |
| 452 | $6.3 \times 10^4$ | $-2.3 \times 10^3$ | $-1.7 \times 10^4$ |
| 500 | $2.1 \times 10^4$ | $-1.7 \times 10^2$ | $4.8 \times 10^2$ |
| 530 | $3.9 \times 10^4$ | $2.0 \times 10^3$ | $7.2 \times 10^2$ |
| 545 | $5.1 \times 10^4$ | $-1.3 \times 10^3$ | $7.0 \times 10^2$ |
| 570 | $4.5 \times 10^4$ | $2.2 \times 10^3$ | $-9.0 \times 10^2$ |
| 584 | $3.4 \times 10^4$ | $-4.1 \times 10^3$ | $-7.1 \times 10^2$ |
| 738 | $1.1 \times 10^3$ | $6.8 \times 10^0$ | $3.5 \times 10^0$ |
| 796 | $8.0 \times 10^2$ | $8.8 \times 10^0$ | $1.1 \times 10^1$ |

Figure 3:
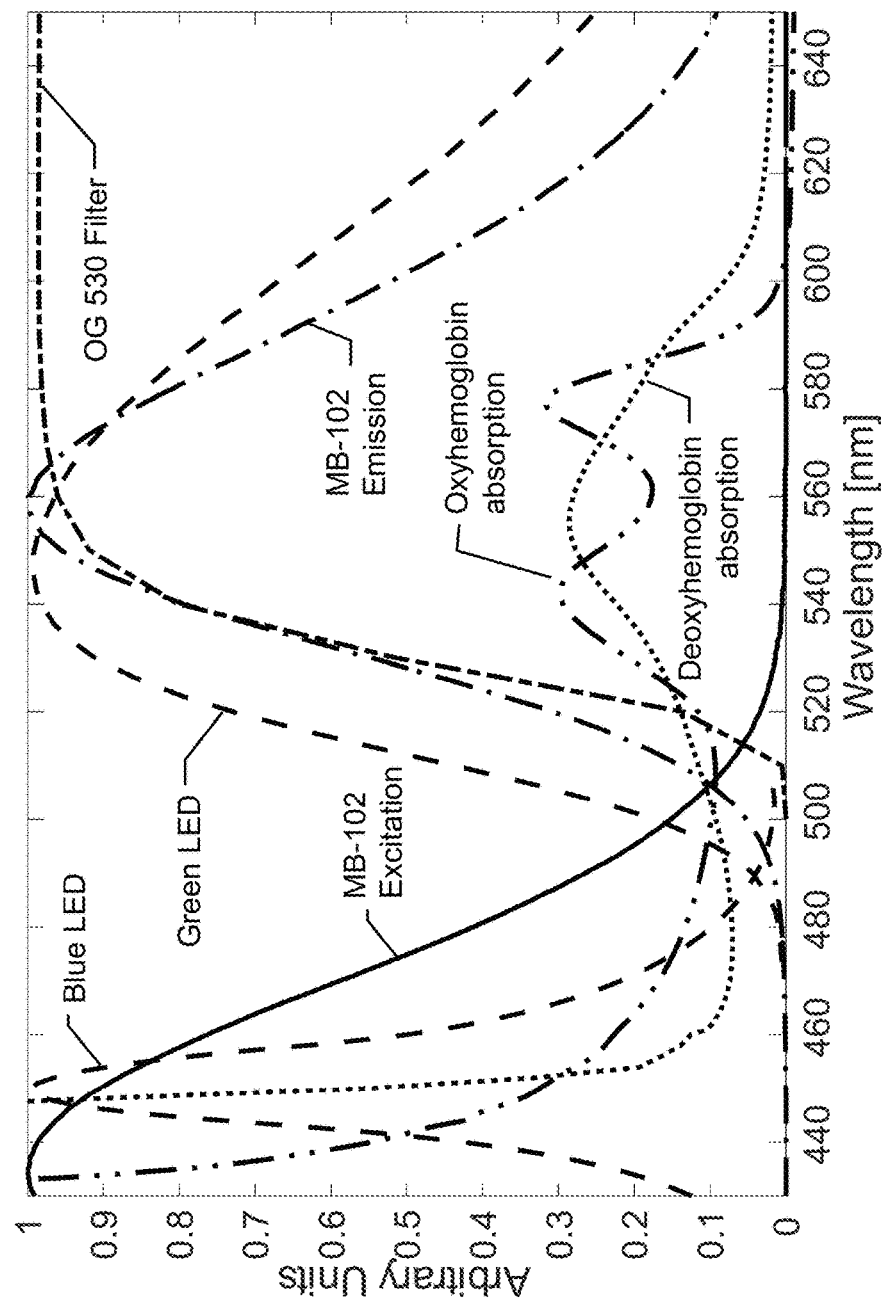
FIG. 3 is a graph summarizing the absorption, transmission, and emission spectra of various devices, materials, and compounds associated with the non-invasive monitoring of an exogenous fluorescent agent in vivo defined over light wavelengths ranging from about 430 nm to about 650 nm.

By way of illustrative example, FIG. 3 is a graph summarizing the absorption spectra for $HbO_2$ and Hb, as well as the absorption and emission spectra of frequency spectra of MB-102, an exogenous fluorescent agent in one aspect. Emission spectra for a blue LED light source and a green LED light source are also shown superimposed over the other spectra of FIG. 3. In this aspect, the system 200 may include a blue LED as the first light source 218, and the excitatory wavelength for the system 200 may be the isosbestic wavelength of about 450 nm. As listed in Table 1 and shown in FIG. 3, the Hb absorbance spectra is strongly sloped at the isosbestic wavelengths of about 420 nm to about 450 nm (see columns 3 and 4 of Table 1), indicating that the relative absorbance of $HbO_2$ and Hb at the isosbestic wavelength of about 450 nm is sensitive to small changes in excitatory wavelength. However, at wavelengths above about 500 nm, the $HbO_2$/Hb spectra are less steeply sloped, and a broader band light source including, but not limited to, an LED with a bandpass filter may suffice for use as a first light source 218.

In another aspect, the excitatory wave length may be selected to enhance the contrast in light absorbance between the exogenous fluorescent agent and the chromophores within the tissues of the patient 202. By way of non-limiting example, as shown in FIG. 3 at the isosbestic wavelength of 452 nm, the light absorption of the MB-102 is more than three-fold higher than the light absorption of the $HbO_2$ and the Hb. Without being limited to any particular theory, a higher proportion of light illuminating the tissue of the patient 202 at a wavelength of about 450 nm will be absorbed by the MB-102 relative to the $HbO_2$ and Hb, thus enhancing the efficiency of absorption by the MB-102 and reducing the intensity of light at the excitatory wavelength needed to elicit a detectable fluorescence signal.

In various aspects, a second isosbestic wavelength may also be selected as the emission wavelength for the system 200. By way of non-limiting example, FIG. 3 shows an emission spectrum of the MB-102 exogenous contrast agent that is characterized by an emission peak at a wavelength of about 550 nm. In this non-limiting example, the isosbestic wavelength of 570 nm may be selected as the emission wavelength to be detected by first and second detectors 222/224. In various other aspects, the emission wavelength of the system 200 may be selected to fall within a spectral range characterized by relatively low absorbance of the chromophores within the tissues of the patient 202. Without being limited to any particular theory, the low absorbance of the chromophores at the selected emission wavelength may reduce the losses of light emitted by the exogenous fluorescent agent and enhancing the efficiency of fluorescence detection.

In various aspects, the first light source 218 and the second light source 220 may be any light source configured to deliver light at the excitatory wavelength and at the emission wavelength. Typically, the first light source 218 delivers light at an intensity that is sufficient to penetrate the tissues of the patient 202 to the exogenous fluorescent agent with sufficient intensity remaining to induce the emission of light at the emission wave length by the exogenous fluorescent agent. Typically, the first light source 218 delivers light at an intensity that is sufficient to penetrate the tissues of the patient 202 to the exogenous fluorescent agent with sufficient intensity remaining after scattering and/or absorption to induce fluorescence at the emission wave length by the exogenous fluorescent agent. However, the intensity of light delivered by the first light source 218 is limited to an upper value to prevent adverse effects such as tissue burning, cell damage, and/or photo-bleaching of the exogenous fluorescent agent and/or the endogenous chromophores in the skin ("auto-fluorescence").

Similarly, the second light source 220 delivers light at the emission wavelength of the exogenous fluorescent agent at an intensity configured to provide sufficient energy to propagate with scattering and absorption through the first region 206 of the patient and out the second region 208 and third region 210 with sufficient remaining intensity for detection by the first light detector 222 and the second light detector 224, respectively. As with the first light source 218, the intensity of light produced by the second light source 220 is limited to an upper value to prevent the adverse effects such as tissue injury or photobleaching described previously.

In various aspects, the first light source 218 and the second light source 220 may be any light source suitable for use with fluorescent medical imaging systems and devices. Non-limiting examples of suitable light sources include: LEDs, diode lasers, pulsed lasers, continuous waver lasers, xenon arc lamps or mercury-vapor lamps with an excitation filter, lasers, and supercontinuum sources. In one aspect, the first light source 218 and/or the second light source 220 may produce light at a narrow spectral bandwidth suitable for monitoring the concentration of the exogenous fluorescence agent using the method described herein. In another aspect, the first light source 218 and the second light source 220 may produce light at a relatively wide spectral bandwidth.

In one aspect, the selection of intensity of the light produced by the first light source 218 and the second light source 220 by the system 200 may be influenced any one or more of at least several factors including, but not limited to, the maximum permissible exposure (MPE) for skin exposure to a laser beam according to applicable regulatory standards such as ANSI standard Z136.1. In another aspect, light intensity for the system 200 may be selected to reduce the likelihood of photobleaching of the exogenous fluorescent source and/or other chromophores within the tissues of the patient 202 including, but not limited to: collagen, keratin, elastin, hemoglobin within red blood cells and/or melanin within melanocytes. In yet another aspect, the light intensity for the system 200 may be selected in order to elicit a detectable fluorescence signal from the exogenous fluorescent source within the tissues of the patient 202 and the first light detector 222 and/or second light detector. In yet another aspect, the light intensity for the system 200 may be selected to provide suitably high light energy while reducing power consumption, inhibiting heating/overheating of the first light source 218 and the second light source 220, and/or reducing the exposure time of the patient's skin to light from the first light detector 222 and/or second light detector.

In various aspects, the intensity of the first light source 218 and the second light source 220 may be modulated to compensate any one or more of at least several factors including, but not limited to: individual differences in the concentration of chromophores within the patient 202, such as variation in skin pigmentation. In various other aspects, the detection gain of the light detectors may be modulated to similarly compensate for variation in individual differences in skin properties. In an aspect, the variation in skin pigmentation may be between two different individual patients 202, or between two different positions on the same patient 202. In an aspect, the light modulation may compensate for variation in the optical pathway taken by the light through the tissues of the patient 202. The optical pathway may vary due to any one or more of at least several factors including but not limited to: variation in separation distances between the light sources and light detectors of the system 200; variation in the secure attachment of the sensor head 204 to the skin of the patient 202; variation in the light output of the light sources due to the exposure of the light sources to environmental factors such as heat and moisture; variation in the sensitivity of the light detectors due to the exposure of the light detectors to environmental factors such as heat and moisture; modulation of the duration of illumination by the light sources, and any other relevant operational parameter.

In various aspects, the first light source 218 and the second light source 220 may be configured to modulate the intensity of the light produced as needed according to any one or more of the factors described herein above. In one aspect, if the first light source 218 and the second light source 220 are devices configured to continuously vary output fluence as needed, for example LED light sources, the intensity of the light may be modulated electronically using methods including, but not limited to, modulation of the electrical potential, current, and/or power supplied to the first light source 218 and/or the second light source 220. In another aspect, the intensity of the light may be modulated using optical methods including, but not limited to: partially or fully occluding the light leaving the first light source 218 and the second light source 220 using an optical device including, but not limited to: an iris, a shutter, and/or one or more filters; diverting the path of the light leaving the first light source 218 and the second light source 220 away from the first region 206 of the patient using an optical device including, but not limited to a lenses, a mirror, and/or a prism.

In various aspects, the intensity of the light produced by the first light source 218 and the second light source 220 may be modulated via control of the laser fluence, defined herein as the rate of energy within the produced light beam. In one aspect, the laser fluence may be limited to ranges defined by safety standards including, but not limited to, ANSI standards for exposure to laser energy such as ANSI Z136.1. Without being limited to any particular theory, the maximum fluence of light delivered to a patient 202 may be influenced by a variety of factors including, but not limited to the wavelength of the delivered light and the duration of exposure to the light. In various aspects, the maximum fluence of light may range from about 0.003 J/cm2 for light at delivered at wavelengths of less than about 302 nm to about 1 J/cm2 for light delivered at wavelengths ranging from about 1500 nm to about 1800 nm for a duration of up to about 10 sec. For light delivered at wavelengths ranging from about 400 nm to about 1400 nm (visible/NIR light) the maximum fluence may be about 0.6 J/cm2 for a duration of up to about 10 sec, and up to about 0.2 J/cm2 for a duration ranging from about 10 sec to about 30,000 sec. For extended exposures, the delivered light is limited to a maximum power density (W/cm2) according to ANSI standards: visible/NIR light is limited to 0.2 W/cm2 and far IR light is limited to about 0.1 W/cm2. Without being limited to a particular theory, extended exposure to light delivered at UV wavelengths is not typically recommended according to ANSI standards.

In another aspect, the fluence of light at the excitatory wavelength produced by the first light source 218 may be modulated in order to provide sufficient energy to propagate through the skin in the first region 206 of the patient 202 to the exogenous fluorescent agent without photobleaching, and to illuminate the exogenous fluorescent agent with energy sufficient to induce detectable fluorescence at the first light detector 222 and/or the second light detector 224. In an additional aspect, the fluence of light at the emission wavelength produced by the second light source 220 may be modulated in order to provide sufficient energy to propagate through the skin in the first region 206 of the patient 202 and through the skin in the second region 208 and the third region 210 without photobleaching to emerge as detectable light at the first light detector 222 and the second light detector 224, respectively. By way of non-limiting example, the fluence of light produced by a light source at 450 nm or 500 nm may be limited to 1.5 and 5 mW/cm$^2$, respectively, to prevent photo-bleaching.

In various aspects, the fluence of the light produced by the first light source 218 and the second light source 220 may be modulated by any suitable systems and/or devices without limitation as described herein above. This modulation may be enabled a single time during operation of the system 200, and as a result, the fluence of the light produced by each of the first light source 218 and the second light source 220 may be relatively constant throughout the operation of the system 200. In another aspect, the light modulation may be enabled at discrete times over the duration of operation of the system 200, or the light modulation may be enabled continuously over the duration of operation of the system 200.

In one aspect, the fluence of the light may be modulated via manual adjustment of any of the power source settings and/or optical device settings as described above when the system 200 is configured in an Engineering Mode. In another aspect, the fluence of the light may be modulated automatically via one or more control schemes encoded in the light source control unit of the controller 212 as described herein below. In this aspect, the degree of modulation may be specified at least in part on the basis of feedback measurements obtained by various sensors provide in the sensor head 204 of the system 200 including, but not limited to, additional light detectors 226 and temperature sensors 228 as described in additional detail herein below.

In various aspects, light produced by the first light source 218 and the second light source 220 are further characterized by a pulse width, defined herein as the duration of the produced light. Although pulse width is typically used to characterize the performance of a light source that produces light in discrete pulses, such as a pulsed laser, it is to be understood that the term "light pulse", as used herein, refers to any discrete burst of light produced by a single light source at a single wavelength to enable the acquisition of a single measurement of fluorescence by the system 200. Similarly, the term "pulse width", as used herein, refers to the duration of a single light pulse produced by a single light source. The pulse width is typically selected based on one or more of at least several factors including, but not limited to: delivery of sufficient light energy to elicit detectable fluorescence from the exogenous fluorescent agent without photobleaching the exogenous fluorescent agent or other chromophores within the tissues of the patient 202; compliance with safety standards for light delivery to patients such as ANSI standards; light delivery at sufficiently high rate to enable data acquisition at a rate compatible with real-time monitoring of renal function; performance capabilities of the selected light sources, light detectors, and other devices of the system 200; preservation of the working life of light sources, light detectors, and other devices related to producing and detecting light energy; and any other relevant factors.

In various aspects, the pulse width of the light produced by the first light source 218 and the second light source 220 may be independently selected to be a duration ranging from about 0.0001 seconds to about 0.5 seconds. In various other aspects, the pulse width of the light produced by the first light source 218 and the second light source 220 may be independently selected to be a duration ranging from about 0.0001 seconds to about 0.001 seconds, from about 0.0005 seconds to about 0.005 seconds, from about 0.001 seconds to about 0.010 seconds, from about 0.005 seconds to about 0.05 seconds, from about 0.01 seconds to about 0.1 seconds, from about 0.05 seconds to about 0.15 seconds, from about 0.1 seconds to about 0.2 seconds, from about 0.15 seconds to about 0.25 seconds, from about 0.2 seconds to about 0.3 seconds, from about 0.25 seconds to about 0.35 seconds, from about 0.3 seconds to about 0.4 seconds, from about 0.35 seconds to about 0.45 seconds, and from about 0.4 seconds to about 0.5 seconds. In one aspect, the pulse widths of the light produced by the first light source 218 and the second light source 220 are both about 0.1 seconds, as illustrated schematically in FIG. 5.

In another aspect, the light produced by the first light source 218 and the second light source 220 may be further characterized by a pulse rate, defined herein as the number of pulses produced by a light source per second. Although pulse rate is typically used to characterize the performance of a light source that produces light in discrete pulses, such as a pulsed laser, it is to be understood that the term "pulse rate", as used herein, refers to the rate of production of a discrete light pulse by a single light source at a single wavelength in association with the acquisition of measurements of fluorescence by the system 200. In various aspects, the pulse rate may be selected based on one or more of at least several factors including, but not limited to: compliance with safety standards for light delivery to patients such as ANSI standards; the performance capabilities of the selected light sources, light detectors, and other devices of the system 200; light delivery rates compatible with data acquisition rates sufficiently rapid for real-time monitoring of renal function; preserving the working life of light sources, light detectors, and other devices related to producing and detecting light energy; and any other relevant factor.

In various aspects, the light sources are configured to deliver light into the tissues of the patient 202 at a single position such as a first region 206, illustrated schematically in FIG. 2. In one aspect, the delivery of light at both the excitatory wavelength and the emission wavelength to the same first region 206 enables both light pulses to share at least a portion of the optical path traveled through the tissues of the patient 202 between the point of entry at the first region 206 and the point of detection at the second region 208 and the third region 210. As discussed in detail herein below, this arrangement of optical paths enhances the quality of data produced by the system 200.

In one aspect, the first light source 218 and the second light source 220 may be operatively coupled to a common means of light delivery. In one aspect (not illustrated) the first light source 218 and the second light source 220 may each be operatively coupled to a first optic fiber and a second optic fiber, respectively, and the first and second optic fibers may be joined to a third optic fiber configured to direct light from the first optic fiber and/or the second optic fiber into the first region 206 of the patient 202. In another aspect, the first light source 218 and the second light source 220 may be operatively coupled to a common optic fiber or other optical assembly configured to direct the light from the first light source 218 and/or the second light source 220 into the first region 206 of the patient 202. In this aspect, the light produced by the first light source 218 and the second light source 220 may be directed in an alternating pattern into the common optic fiber or other optical assembly using an adjustable optical device including, but not limited to, dichroic mirror or a rotating mirror.

Figure 10:
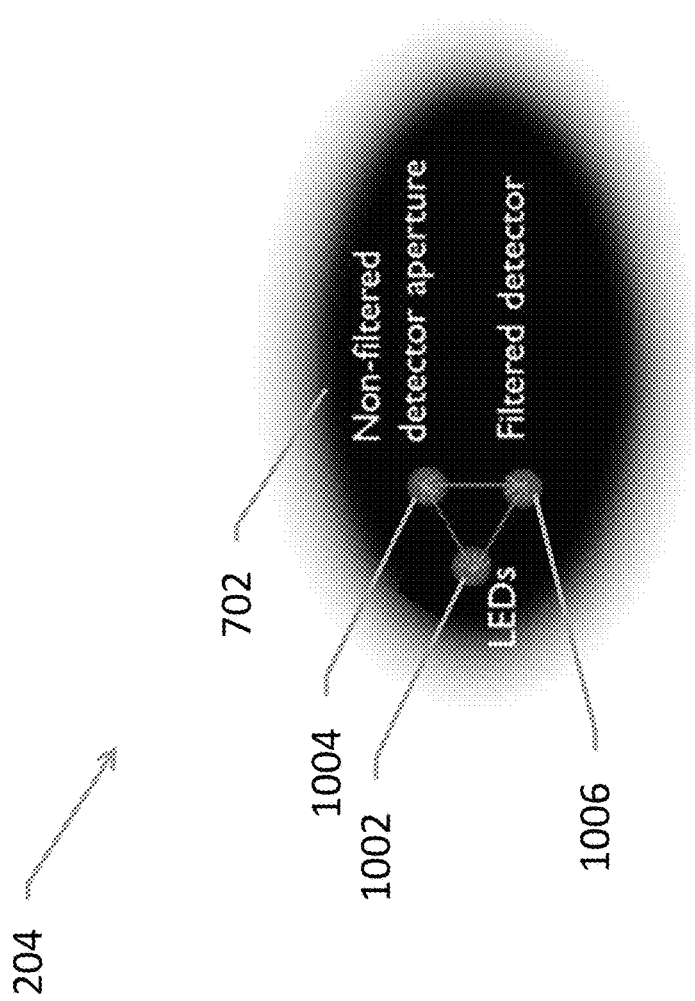
FIG. 10 is a schematic illustration of the apertures formed within a contact surface of a sensor head of a renal function monitoring system in one aspect.

In an aspect, the system 200 may include the sensor head 204 provided with a sensor mount 912 configured with one or more wells within which the light sources 218/220 and light detectors 222/224 may be attached in a predetermined arrangement. In one aspect, illustrated in FIG. 9 and FIG. 10, the first light source 218 and the second light source 220 may be situated within a source well 902 of the sensor mount 912 positioned within the sensor head 204 (see FIG. 9). In an aspect, the source well 902 may contain a first LED light source 218 producing light at the excitation wavelength and a second LED light source 220 producing light at the emission wavelength operatively coupled to a single light delivery aperture 1002 (see FIG. 10) formed through the aperture plate 702, which ensures that both wavelengths of light (i.e. excitatory and emission) enter the skin of the patient 202 at approximately the same location including, but not limited to, a first region 206 as illustrated schematically in FIG. 2. In an aspect, the source well 902 further contains a first monitor photodiode 904 and a second monitor photodiode 906, which are used to correct for variations in output power from the LED light sources as described in further detail herein below.

In an aspect, only a fraction of the light energy produced by the LED light sources is delivered to the skin of the patient 202 via the single light delivery aperture 1002. In one aspect, the skin of the patient 202 receives about 1% of the light energy produced by the LED light sources. In various other aspects, the skin of the patient 202 receives about 2%, about 3%, about 4%, about 5%, about 7.5%, about 10%, about 20%, and about 50% of the light energy produced by the LED light sources. Without being limited to any particular theory, the fraction of light produced by the LED light sources delivered to the skin of the patient 202 may be increased by the incorporation of additional optical elements configured to focus and/or direct the light from each LED light source to the light delivery aperture 1002. In another aspect, a diffuser may be used to mix the output of the light sources so that the light energy is rendered homogeneous at the surface of the skin of the patient.

ii) Light Detectors

Referring again to FIG. 2, the system 200 further includes a first light detector 222 and a second light detector 224 in various aspects. In an aspect, the first light detector 222 is configured to measure unfiltered light emitted from the tissue of the patient 202 at the second region 208, and the second light detector 224 is configured to measure filtered light emitted from the tissue of the patient 202 at the third region 210. In this aspect, the second light detector 224 further comprises a optical filter 244 configured to block light at the excitation wavelength. As a result, the first light detector 222 is configured to measure light received at both the excitation and emission wavelengths and the second light detector 224 is configured to detect light received at the emission wavelength only. Combined with the illumination of the tissues of the patient 202 with light at the excitatory wavelength only and at the emission wavelength only in an alternating series (see FIG. 5) the measurements from the first light detector 222 and a second light detector 224 may be analyzed as described herein below to measure the fluorescence of an exogenous fluorescence agent and to correct the fluorescence measurements by removing the effects of dynamic changes in the background signal to the correction methods described herein below.

In various aspects, the second region 208 and third region 210 within the tissues of the patient 202, from which light is detected by the first light detector 222 and a second light detector 224, respectively, are each separated by a nominal distance from the first region 206 to which light produced by the first light source 218 and the second light source 220 is delivered. This nominal separation distance may be selected to balance two or more effects that may impact the quality of data detected by the light detectors. Without being limited to any particular theory, as the nominal separation distance increases, the total detected signal from the light detectors may decrease due to light scattering along the longer optical path between light source and light detector. This effect may be mitigated by the choice of emission wavelength, which may result in a less pronounced decrease in the detected fluorescence signal (i.e. light at the emission wavelength) relative to the signals associated with detected light at the excitation wavelengths as the nominal separation distance increases. Longer nominal separation distances result in higher sensitivity to signal changes due to changing tissue optical properties.

In one aspect, the nominal separation distance may range from 0 mm (i.e. colocation of light sources and light detectors) to about 10 mm. In various other aspects, the nominal separation distance may range from about 1 mm to about 8 mm, from about 2 mm to about 6 mm, and from about 3 mm to about 5 mm. In various additional aspects, the nominal separation distance may be 0 mm, about 1 mm, about 2 mm, about 3 mm, about 4 mm, about 5 mm, about 6 mm, about 8 mm, and about 10 mm. In one aspect, the nominal separation distance may be about 4 mm to balance these competing effects of logarithmic drop-off of signal and reduced size of the background signal relative to the signal from the exogenous fluorescent agent.

Referring again to FIG. 9, the first light detector 222 may be positioned within a first detection well 908 of the sensor mount 912 and the second light detector 224 may be positioned within a second detection well 910 of the sensor mount 912 within the sensor head 204. The first light detector 222 and the second light detector 224 may receive light from tissue of the patient 202 through a first detector aperture 1004 and second detector aperture 1006, respectively. In an aspect, the first detector aperture 1004, the second detector aperture 1006, and the light delivery aperture 1002 are mutually separated from one another by the nominal separation distance disclosed herein above including, but not limited to, a nominal separation distance of 4 mm. In an aspect, the first detection well 908, second detection well 910, and light source well 902 of the sensor mount 912 may be optically isolated from one another to ensure that light from the light sources 218/220 does not reach the light detectors 222/224 without coupling through the skin of the patient 202. The separation between the two detection wells 908/910 ensures that the detected fluorescence signal from the exogenous fluorescent agent is distinguishable from the unfiltered excitation light, as described in detail herein below.

In an aspect, the three apertures 704 of the aperture plate 702 (see FIG. 7) are circular with a diameter ranging from about 0.5 mm to about 5 mm. In various other aspects, the diameters of the apertures may range from about 0.5 mm to about 1.5 mm, about 1 mm to about 2 mm, about 1.5 mm to about 2.5 mm, about 2 mm to about 3 mm, about 2.5 mm to about 3.5 mm, about 3 mm to about 4 mm, about 3.5 mm to about 4.5 mm, and about 4 mm to about 5 mm.

In one aspect, the three apertures 704 of the aperture plate 702 are circular apertures with a diameter of about 1 mm diameter. This finite width of the apertures may result in an effective source-detector separation of less than the nominal separation distance because of the logarithmic drop-off of signal with increasing separation distance from the light sources at the skin interface of the sensor head 204.

In various aspects, the light detectors 222/224 of the system 200 may be any suitable light detection device without limitation. Non-limiting examples of suitable light detection devices include: photoemission detectors such as photomultiplier tubes, phototubes, and microchannel plate detectors; photoelectric detectors such as LEDs reverse-biased to act as photodiodes, photoresistors, photodiodes, phototransistors; and any other suitable light detection devices. In an aspect, the light detectors 222/224 are sufficiently sensitive to detect the fluorescence emitted by the exogenous fluorescent agents within the tissues of patients 202 that include melanin ranging from about 1% to about 40% melanin in the epidermis and blood volume ranging from about 0.5% to about 2% of the skin volume. In one aspect, the light detectors 222/224 may be silicon photo-multiplier (SPM) devices.

In an aspect, the first light detector 222 may be configured to detect light at both the excitatory frequency and at the emission frequency, and the second light detector 224 may be configured to detect light at the emission frequency only. In one aspect, the second light detector 224 may respond only to light of the emission wavelength as a result of the design and materials of the sensor elements of the second light detector 224. In another aspect, the second light detector 224 may respond to a wider range of light wavelengths, but may be positioned downstream from an optical filter configured to pass only the portion of incoming light with the emission wavelength and further configured to block the passage of light wavelengths outside of the emission wavelength.

Any suitable optical filter may be selected for use with the second light detector 224 to detect light selectively at the emission wavelength. Non-limiting examples of suitable optical filters include absorptive filters and interference/dichroic filters. Without being limited to any particular theory, the performance of an absorption filter does not vary significantly with the angle of incident light, whereas the performance of an interference/dichroic filter is sensitive to the angle of incident light and may require additional collimation optics to effectively filter the Lambertian light distribution representative of light emitted from the skin of the patient 202.

In one aspect, the second light detector 224 may be positioned downstream of an absorptive long-pass filter configured to pass light above a predetermined wavelength to the second light detector 224. By way of non-limiting example, the second light detector 224 may be positioned downstream of an long-pass OG530 filter configured to pass light with wavelengths above about 530 nm. Other non-limiting examples of suitable filters include a Hoya 054 filter and a Hoya CM500 filter.

In various aspects, an optical filter 244 configured to absorb excitation wavelength light may be positioned within the second detection well 910 between the second light detector 224 and the second detector aperture 1006. In one aspect, the optical filter 244 may be constructed from OG530 Schott glass. The thickness of the optical filter 244 may be selected to enable an optical density sufficient to filter the excitation light by about three orders of magnitude. In one aspect, the thickness of the optical filter 244 may range from about 1 mm to about 10 mm. In various other aspects, the thickness of the optical filter 244 may range from about 1 mm to about 8 mm, from about 2 mm to about 6 mm, and from about 3 mm to about 5 mm. In various additional aspects, the thickness of the optical filter 244 may be about 1 mm, about 2 mm, about 3 mm, about 4 mm, about 5 mm, about 6 mm, about 7 mm, about 8 mm, about 9 mm, and about 10 mm. In one aspect, the optical filter 244 is a 3-mm thick filter constructed of OG530 Schott glass.

In an additional aspect, an optical diffuser may be provided within the light source well 902. In this aspect, the optical diffuser enables mixing of the light entering the light source well 902 from the first and second light sources 218/220. By mixing the light from the first and second light sources 218/220 using the optical diffuser prior to illumination of the first region 206 of the patient 202, the similarity of the optical paths taken by emission-wavelength light and excitation-wavelength light through the tissues of the patient is enhanced relative to the corresponding optical paths taken by unmixed light, thereby reducing a potential source of variation.

In an aspect, a transparent material configured to pass light of both the excitatory and emission wavelengths may be positioned within the first detection well 908 between the first light detector 222 and the first detector aperture 1004. In this aspect, the transparent material may be any material with similar optical properties to the material of the optical filter 244 including, but not limited to, thickness and index of refraction. In one aspect, the transparent material within the first detection well 908 may be fused silica glass of the same thickness as the optical filter 244.

By way of non-limiting example, the transmission spectrum of the OG 530 filter is provided in FIG. 3. As illustrated in FIG. 3, the transmission spectrum of the OG 530 filter overlaps with the emission spectrum of the MB-102 exogenous fluorescent agent and the emission spectrum of a green LED used as a second light source 220 (emission wavelength). In addition, the transmission spectrum of the OG 530 filter excludes the emission spectrum of the blue LED used as a first light source 218 and the absorbance spectrum of the MB-102 exogenous fluorescent agent (excitation wavelength).

In an aspect, the transparent material such as glass 246 and the optical filter 244 may be secured to ledges formed within the first detection well 908 and the second detection well 910, respectively. The transparent material such as glass 246 and the optical filter 244 may be secured in place using an opaque and/or light absorbing adhesive including, but not limited to, black epoxy to ensure that all light received through the first detector aperture 1004 and the second detector aperture 1006 travels through the optical filter 244 or glass 246 before detection by the first and second light detectors 222/224. In another aspect, the sides of the optical filter 244 or glass 246 may be painted black with a light-absorbing coating including, but not limited to, India ink to ensure that light does not reach the first and second light detectors 222/224 without passing through the optical filter 244 or glass 246.

In an aspect, the height of the detection wells 908/910, combined with the diameter of the detector apertures 1004/1006 may limit the fraction of the light emitted from the second region 208 and third region 210 of the patient's skin that reaches the active areas of the light detectors 222/224 due to the Lambertian distribution of the angle of the light leaving the patient's skin. In one aspect, the fraction of light emitted from the second region 208 and third region 210 of the patient's skin received by the light detectors 222/224 may range from about 5% to about 90%. In various other aspects, the fraction of light may range from about 5% to about 15%, from about 10% to about 20%, from about 15% to about 25%, from about 20% to about 30%, from about 25% to about 35%, from about 30% to about 40%, from about 35% to about 45%, from about 40% to about 60%, from about 50% to about 70%, and from about 60% to about 90%.

In one aspect, for the sensor head 204 illustrated in FIG. 6 and FIG. 7 with 1-mm diameter apertures 1002/1004/1006, about 10% of the light emitted from the surface of the patient's skin may reach the active area of the light detectors 222/224 to be detected. In various aspects, the sensor head 204 may further include additional optical elements including, but not limited to, lenses and/or prisms configured to compensate for the Lambertian distribution of light angles in order to enhance the fraction of light emitted from the patient's skin that is directed to the active area of the light detectors 222/224.

iii) Temperature Sensors

Referring to FIG. 2, the sensor head 204 may further include one or more additional temperature sensors 228 configured to monitor temperatures of various regions within the sensor head 204 and in the vicinity of the sensor head 204. Non-limiting examples of suitable regions for which the temperature may be monitored by the one or more additional temperature sensors 228 include: temperature at the skin surface of the patient 202; temperature in the vicinity of the first light source 218 and/or second light source 220; ambient temperature outside of the sensor head 204; temperature of housing 600 of sensor head 204; and any other suitable region. In one aspect, additional temperature sensors 228 may be configured to monitor the temperatures in the vicinity of temperature-sensitive electrical components including, but not limited to: light sources 218/220 such as LEDs, light detectors 222/224 such as silicon photomultipliers (SPMs), and any other temperature-sensitive electrical components of the sensor head 204. In some aspects, one or more temperatures measured by one or more additional temperature sensors 228 may be used as feedbacks in a control method for one or more of the temperature-sensitive devices of the system 200 as described herein below.

By way of non-limiting example, a temperature measurement may be used to control the amount of light energy produced by an LED used as a first or second light source 218/220. In this example, LED temperatures measured by an second temperature sensor 1108 (see FIG. 11) may be used in a control scheme to modulate the amount of power supplied to an LED light source to compensate for the effect of LED temperature on the light output of the LED. In another aspect, additional temperature sensors 228 may monitor the temperatures of LED light sources 218/220 to monitor and/or compensate for temperature variations of the LEDs as well as to monitor and/or compensate for temperature-dependent transmission of the optical filters to maintain relatively constant output wavelengths.

By way of another non-limiting example, an additional temperature sensor 228 may be included in the sensor head 204 in the form of a temperature sensor 816 (see FIG. 8) configured to monitor the temperature of the housing 600 in the vicinity of the contact surface 606 of the sensor head 204. Referring to FIG. 7, FIG. 8, and FIG. 9, the temperature sensor 816 may be epoxied into the temperature sensor opening 706 in the aperture plate 702 in one aspect. In this aspect, the space 918 between the circuit board (not shown) and the lower housing 604 may be filled with a thermally conductive putty to ensure good thermal conduction and dissipation.

In this example, the measured housing temperature may be used to modulate the light output of the sensor head 204 to prevent overheating of the skin of the patient 202 during use. In another aspect, additional temperature sensors 228 may monitor the temperatures of LED light sources 218/220 to monitor and/or compensate for temperature variations of the LEDs to enable the maintenance of relatively constant output wavelengths by the LED light sources 218/220.

In an additional aspect, temperatures measured by one or more additional temperature sensors 228 may provide for subject safety by disabling one or more electrical devices including the light sources 218/220 and/or light detectors 222/224 if an over-temperature condition is detected. In one aspect, an over-temperature condition may be indicated if the housing temperature detected by the temperature sensor 816 is greater than about 40° C. In various other aspects, an over-temperature condition may be detected of the housing temperature is greater than about 40.5° C. or greater than about 41.0° C.

B. Controller

Figure 11:
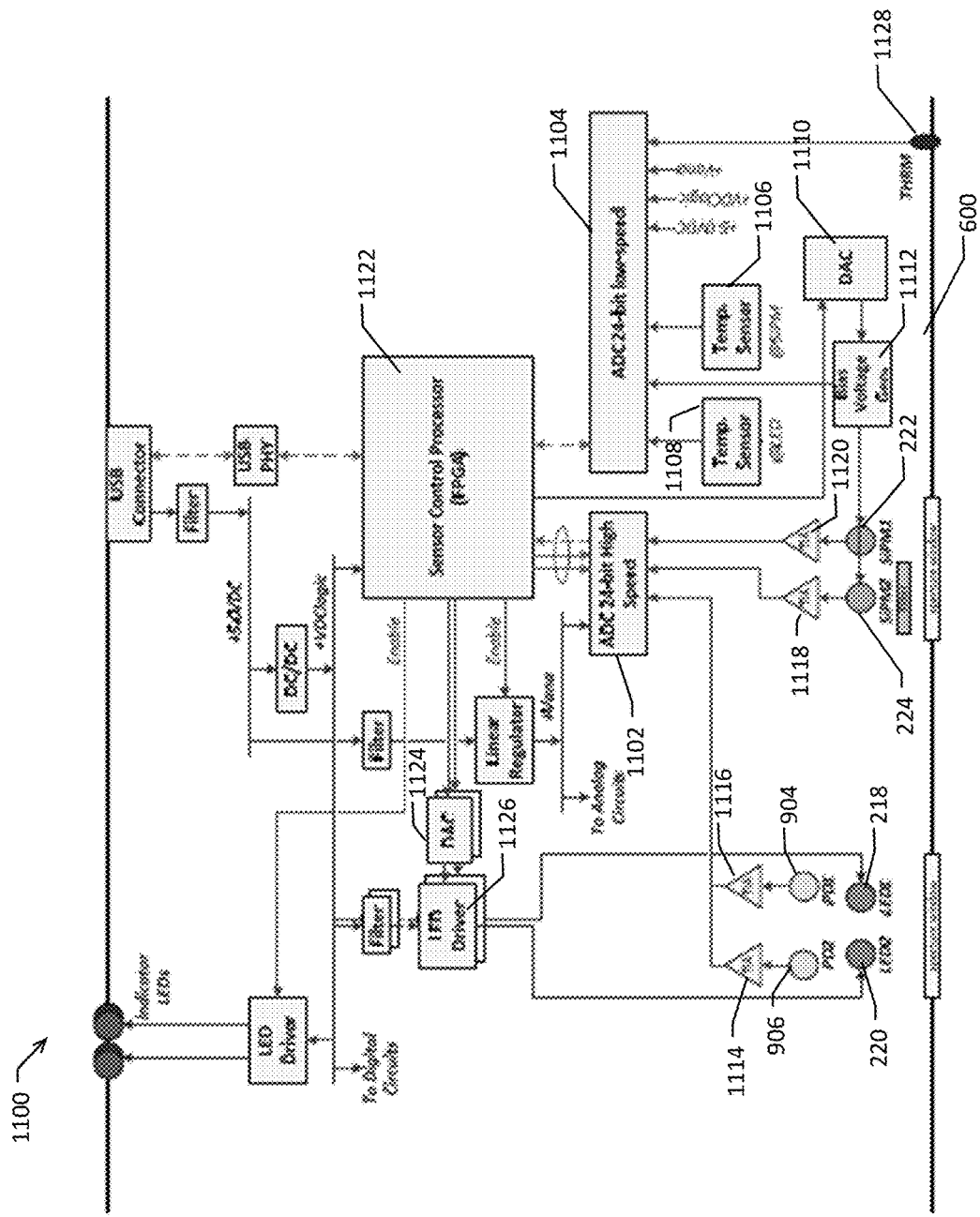
FIG. 11 is a schematic illustration of synchronous detection of light by a light detector of a sensor head in one aspect.

Referring again to FIG. 2, the system 200 in various aspects may include a controller 212 configured to operate the light sources 218/200 and light detectors 222/224 in a coordinated fashion to obtain a plurality of measurements used to obtain the fluorescence of the exogenous fluorescent agent within the tissues of the patient 202, to correct the fluorescence data to remove the effects of dynamic changes in the background signal as described herein below, and to transform the fluorescence measurements into a parameter representative of the renal function of the patient 202. FIG. 11 is a schematic diagram of an electronic circuit 1100 that illustrates the arrangement of various electrical components that enable the operation of the system 200 in an aspect. In one aspect, the controller 212 may be a computing device further including an operation unit 214 and a display unit 216.

i) Light Source Control Unit

Figure 5:
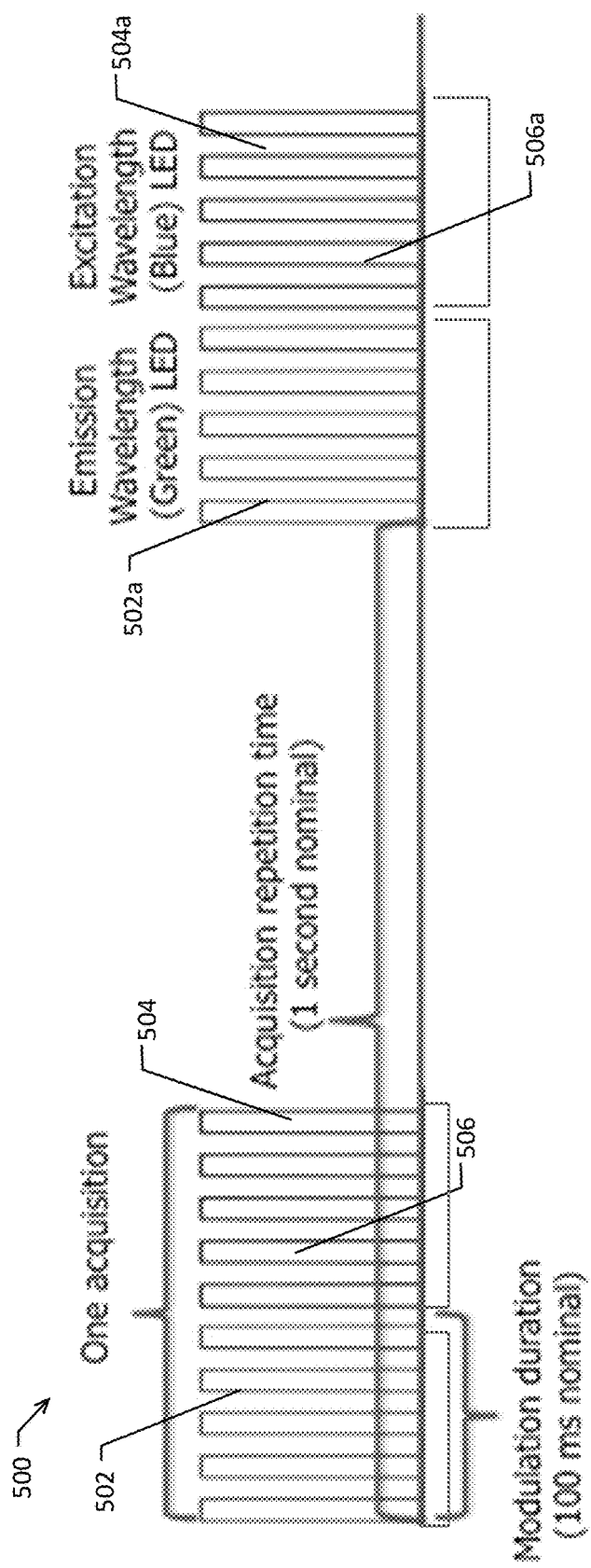
FIG. 5 is a schematic illustration of the timing of light pulse cycles associated with data acquisition by a dual-wavelength renal monitoring system in one aspect, in which each light pulse cycle includes light pulses produced at the excitation wavelength and at the emission wavelength in sequence.

Referring again to FIG. 2, the controller 212 may include a light source control unit 230 configured to operate the first light source 218 and the second light source 220 to produce light at the excitation wavelength and emission wavelength, respectively in a coordinated manner to produce a repeating pulse sequence as illustrated schematically in FIG. 5. In various aspects, the light source control unit 230 may produce a plurality of light control signals encoding one or more light control parameters including, but not limited to: activation or deactivation of each light source; relative timing of activation and deactivation of each light source to enable light pulse width, pulse repetition rate, electrical power delivered to the light source or other parameter associated with light pulse fluence or light pulse power; other light source-specific parameters controlling the light output of the light source; and any other relevant light control parameter. In an aspect, the light source control unit 230 may receive one or more feedback measurements used to modulate the plurality of control signals to compensate for variations in performance of the light sources in order to maintain a relatively stable output of light from the light sources. Non-limiting examples of feedback measurements used by the light source control unit 230 include: light output of the light sources 218/220 measured within the source well 902 by the first monitor photodiode 904 and the second monitor photodiode 906, respectively, temperatures of the light sources 218/220, and any other feedback measurement relevant to monitoring the performance of light sources 218/220.

By way of non-limiting example, the light source control unit 230 may be configured to operate LED light sources 218/220. In this example, the light output of the LED light sources 218/220 may be controlled by controlling the magnitude of current provided to each LED. In an aspect, the light source control unit 230 may include at least one waveform generator 1122 including, but not limited to, a field programmable gate array FPGA with a 16-bit DAC 1124 operatively coupled to a LED current source 1126, as illustrated in FIG. 11. In an aspect, waveforms generated by the at least one waveform generator 1122 including, but not limited to square waves, may control the output from the LED current source 1126. In an aspect, the magnitude of the current supplied to the LED light sources 218/220 may be adjustable based on the waveform signals provided by the waveform generator/FPGA 1122.

Referring to FIG. 5, in one aspect, each light pulse sequence 500 includes an emission wavelength light pulse 502 and an excitatory wavelength light pulse 504 that are both made up of a plurality of square waves 506 produced by the first and second LED light sources 218/220. Referring to FIG. 11, square waves generated by the waveform generator 1122 are received by the LED current source 1126. The current generated by the LED current source includes a square waveform similar to the waveform generated by the waveform generator 1122. Without being limited to any particular theory, because the intensity of light produced by the LED light sources 218/220 is proportional to the magnitude of the current received, the light produced by the LED light sources 218/220 also includes the square waveform as illustrated in FIG. 5. In another aspect, discussed in additional detail below, the square waves produced by the waveform generator 1122 may also be used by the acquisition unit 234 in a synchronous detection method to reduce the effects of various confounding factors including, but not limited to, the detection of ambient light, from the detector signals generated by the light detectors 222/224 during illumination of the tissues of the patient at the emission and excitatory wavelengths by the first and second light sources 218/220, respectively.

In various other aspects, a variety of alternate LED pulse modulation schemes may be equivalently employed without limitation. In one aspect, the excitation and emission pulses are delivered in an alternating series interspersed with a dark period after each pulse. In another aspect, the first and second LED light sources 218/220 are each modulated with a 50% duty cycle but at different modulation frequencies, allowing the signals associated with the excitation and emission pulses to be separated by frequency filtering.

Without being limited to any particular theory, the overall optical power delivered to the patient's skin may be limited by at least two factors: photobleaching of the exogenous fluorescent agent and/or endogenous chromophores, as well as overheating of the patient's tissues illuminated by the system 200. In one aspect, tissue heating may impose an absolute limit of about 9 mW on the optical power that can be delivered to the skin, based on safety standards including, but not limited to, ANSI/IESNA RP-27.1-05. In another aspect, photobleaching of the skin autofluorescence associated with endogenous chromophores including, but not limited to, collagen, hemoglobin, and melanin may contribute a background signal to the measured fluorescence that remains relatively constant so long as no autobleaching of the chromophores occurs. This constant autofluorescence background may be subtracted from the raw fluorescence signal, but if autofluorescence varies over time due to photobleaching, this background correction may interfere with the kinetic calculation of the renal decay time constant (RDTC). In an aspect, the light output power of the first light source 218 and/or second light source 220 may be limited to levels below power thresholds associated with chromophore photobleaching.

Referring again to FIG. 9, the light output of the light sources 218/220 may be measured using monitor photodiodes 904/906 in various aspects. Because the light intensity reaching these monitor photodiodes 904/906 is typically much stronger than the light intensity that reaches the light detectors 222/224 through the patient's skin, less sensitive light detecting devices including, but not limited to, PIN photodiodes may be used to monitor the output of the light sources 218/220.

In various aspects, the system 200 may be configured to operate over a range of skin tones observed in the human population. Without being limited to any particular theory, variations in skin tones between different patients 202 may result in variations in the detected fluorescence signals ranging over about three orders of magnitude. In addition, variations in the concentrations of exogenous fluorescent agent within each patient 202 may vary over a range of about two orders of magnitude due to renal elimination of the agent over time. In various aspects, the system 200 may be configured to detect fluorescence from the endogenous fluorescent agent over an intensity range of more than five orders of magnitude. In these various aspects, the system 200 may be configured by modulation of at least one operational parameter including, but not limited to: magnitude of light output by the light sources 218/220 and sensitivity of light detectors 222/224 corresponding to detector gains.

In one aspect, the intensity of the light output by the light sources 218/220 may be manually set by a user via the operation unit 214. In another aspect, the light source control unit 230 may be configured to modulate the intensity of light produced by the light sources 218/220 automatically. In an aspect, the light source control unit 230 may be configured to control the light intensity produced by the LED light sources 218/220 within a range of normalized output intensities from 0 (off) to 1 (maximum power). In an aspect, the intensity of the light sources 218/220 may be set by the light source control unit 230 in coordination with the detector gains of the light detectors 222/224 set by the light detector control unit 232, as described herein below.

In one aspect, signals obtained during the first 10 detection cycles obtained by the system 200 after initialization of data acquisition, but prior to the injection of the exogenous fluorescent agent, may be used by the light source control unit 230 to automatically adjust the light intensity produced by the LED light sources 218/220, as well as the gain of the light detectors 222/224. In this example, the initial detection cycle may be obtained with the LED light sources 218/220 set at about 10% of maximum LED intensity (corresponding to a normalized output intensity of 0.1) and with a low gain setting for the light detectors 222/224. Based on the detected intensity of light received at the light detectors 222/224 at the excitation and emission wavelengths for one detection cycle, the corresponding LED intensities may be modulated to enable the analog signals produced by the light detectors 222/224 to correspond to about ¼ of the full range of each detector analog-to-digital convertor (ADC) at the low detector gain setting. If the signals produced by the light detectors 222/224 in response to the light produced by the second LED light source 220 at the emission wavelength do not agree, the larger signal may be used to modulate the power setting of the second LED light source 220. If the method described above results in modulation to an LED intensity setting higher than the maximum intensity (corresponding to a normalized output intensity of 0.1), the LED intensity setting is set to the maximum setting. Without being limited to any particular theory, the targeted levels of signals produced by the light detectors 222/224 (i.e. ¼ of the ADC range) is selected to reserve additional light detection capacity to detect signals resulting from variations in optical properties of the tissues of the patient 202 during the study due to any one or more of a plurality of factors including, but not limited to, the introduction of the exogenous fluorescent agent into the patient 202.

In the above one aspect, once the LED intensities are set by the light source control unit 230 in coordination with the detector gains of the light detectors 222/224 set by the light detector control unit 232 over the first 10 detection cycles, an additional 10 detection cycles are obtained to confirm the suitability of these settings for operation of the system 200 given the tissue properties of the particular patient 202, followed by a recalculation of the LED intensity settings and detector gains as described herein. If the newly calculated LED intensity is within a factor of two of the previously determined setting, and the detector gains are not changed, the previously determined settings are maintained for subsequent data acquisition cycles used to determine renal function. Otherwise, the settings are updated using the same method described herein and another 10 data acquisition cycles conducted to confirm the stability of the settings. This process repeats until either the settings are determined to be acceptably stable or 10 data acquisition cycles are conducted to obtain the settings, in which case the most recently determined settings are used for all subsequent data acquisitions, and the user may be notified via the display unit 216 that the settings may not be optimal.

ii) Light Detector Control Unit

Referring again to FIG. 2, the controller 212 may include a light detector control unit 232 configured to operate the first light detector 222 and the second light detector 224 to enable the detection of light at the emission wavelength and unfiltered light at all wavelengths, respectively. In various aspects, the light detector control unit 232 may produce a plurality of detector control signals encoding one or more detector control parameters including, but not limited to, detector gains. In various other aspects, the light detector control unit 232 may produce a plurality of light measurement signals encoding the intensity of light detected by the light detectors 222/224 including, but not limited to raw detector signals that may be received by an analog-to-digital convertor (ADC) 1102 (see FIG. 11) in various aspects. In another aspect, the detector gains and/or other detector control signals may be manually set by a user detector gains when the system 200 is configured in an Engineering Mode.

In various other aspects, the amount of light received by the light detectors 222/224 may vary due to any one or more of at least several factors including, but not limited to: variation in skin tones observed between individual patients 202, variations in the concentrations of exogenous fluorescent agent within each patient 202, and any other relevant parameter. In one aspect, gains of the first light detector 222 and the second light detector 224 may be set by a user via the operation unit 214. In another aspect, the light detector control unit 232 may be configured to modulate the gain of the light detectors 222/224 automatically via a bias voltage gain of the bias voltage generator 1112 (see FIG. 11).

In one aspect, signals obtained during the first 10 detection cycles obtained by the system 200 after initialization of data acquisition, but prior to the injection of the exogenous fluorescent agent, may be used by the light detector control unit 232 to automatically adjust the gains of the light detectors 222/224, as well as the output intensities of the light sources 218/220. As described herein previously, the initial detection cycle may be obtained with the LED light sources 218/220 set at about 10% of maximum LED intensity (corresponding to a normalized output intensity of 0.1) and with a low gain setting for the light detectors 222/224 and the LED intensities may be modulated to enable the analog signals produced by the light detectors 222/224 to correspond to about ¼ of the full range of each detector analog-to-digital convertor (ADC) at the low detector gain setting.

In this one aspect, if the intensity of the first LED light source 218 (producing light at the excitation wavelength) is set to the maximum of the LED power range, a high detector gain may be considered for the second light detector 224 corresponding to the filtered measurements of the excitation wavelength only. In various aspects, the high detector gain may be 10-fold higher than the corresponding low detector gain for a given light detector. Without being limited to any particular theory, the expected peak detected fluorescence signal from the exogenous fluorescence agent over the course of injection and renal elimination is typically expected to be about 10% of the magnitude of the signal received during illumination at the excitation wavelength by the first light source 218, assuming that the exogenous fluorescence agent is MB-102 introduced into the patient 202 at a dose level of about 4 μmol/kg of patient weight. In an aspect, if the expected detector signal received during illumination at maximum LED intensity and with the detector gain set to the high setting remains below 10% of the range of the detector ADC, the detector gain for that measurement be increased by ten-fold. In another aspect, the saturation condition may persist for a pre-defined period of time including, but not limited to, a 30-second period before adjustments are made to the detector gain or LED power to avoid reacting to spurious signal spikes.

In another aspect, the light detector control unit 232 may adjust the detector gain to a lower gain level if the detected light signals from one of the light detectors 222/224 exceed a threshold percentage of the maximum ADC range to avoid signal saturation. Although the highest threshold percentage of the maximum ADC range associated with signal saturation is 100%, the onset of severe detector non-linearity takes place at threshold percentages of about 40% or more, and mild detector non-linearity occurs at threshold percentages in excess of about 15%. In various aspects, the threshold percentage of the maximum ADC range may be 40%, 35%, 30%, 25%, 20%, 18%, 17%, 16%, 15%, 14%, 13%, 12%, 11%, 10%, 9%, 8%, 7%, 6%, or 5% of the maximum ADC range. In one aspect, if the detected light signals from one of the light detectors 222/224 exceed about 8% of the maximum ADC range, the gain setting will be adjusted. By way of non-limiting example, if the detector gain on the nearly saturated signal is high, it will be adjusted to low. If the current detector gain is set to low and the corresponding detected light signal remains above the threshold percentage of the maximum ADC range, the LED output power setting of the corresponding LED light source may be reduced ten-fold.

In an aspect, the light detector control unit 232 may receive one or more feedback measurements used to modulate the plurality of detector signals to compensate for variations in the performance of the light detectors due to variations in temperature and/or light source output. Non-limiting examples of feedback measurements used by the light detector control unit 232 include: light output of the light sources 218/220 measured within the source well 902 by the first monitor photodiode 904 and the second monitor photodiode 906, respectively (see FIG. 11), temperatures of the light detectors 222/224 measured by a first temperature sensor 1106, LED temperatures measured by a second temperature sensor 1108, temperature of the sensor head housing measured by a third temperature sensor 1128, LED supply current from the LED current source 1126, and any other feedback measurement relevant to monitoring the performance of light detectors 222/224.

In various aspects, the light detectors 222/224 may be silicon photon multiplier (SPM) detectors that may include low-noise internal amplification, and may function at lower light levels relative to other light sensor devices such as PIN photodiodes. The detector signal generated by the SPM detectors 222/224 may be amplified using transimpedance amplifiers 1120/1118, respectively (see FIG. 11) to translate a current generated by each SPM light detector 222/224 into a measurable detector voltage. The transimpedance amplifier 1118 on the second SPM light detector 224 (i.e. detects filtered lights at the excitation wavelength only) may include a switchable detector gain that may select a low gain configured to detect a larger dynamic range for fluorescence measurements when the first LED light source 218 is activated to produce light at the emission wavelength. The switchable detector gain that may further select a high gain setting for the second SPM light detector 224 when the second light source 220 is inactive to enhance the sensitivity of the second SPM light detector 224 during the phase of the detection cycle when light at the emission wavelength produced by the exogenous fluorescent agent within the tissues of the patient 202 is detected, to ensure that the expected dark current from the second SPM light detector 224 occupies less than ¼ of the total ADC output range. In one aspect, the second transimpedance amplifier of the second SPM light detector 224 may include a low detector gain configured to provide a transimpedance gain of about 4 kΩ corresponding to about twice the value of the transimpedance resistor due to differential operation, and may further include a high detector gain configured to provide a transimpedance gain of about 40 kΩ. In another aspect, the first transimpedance amplifier of the first SPM light detector 222 may include a fixed detector gain configured to provide a transimpedance gain of about 2 kΩ.

iii) Acquisition Unit

Referring again to FIG. 2, the controller 212 may further include an acquisition unit 234 in various aspects. The acquisition unit 234 may be configured to receive a plurality of signals from the light sources 218/220, light detectors 222/224, and additional light detectors 226 and additional temperature sensors 228 and processing the plurality of signals to produce one or more raw signals including, but not limited to, raw fluorescence signals encoding the intensity of fluorescence detected by the second light detector 224 during illumination at the excitation wavelength, and raw internal reflectance signals corresponding to the intensity of light at the excitation wavelength detected by the first light detector 222 during illumination at the excitation wavelength as well as the intensity of light at the emission wavelength detected by the both light detectors 222/224 during illumination at the emission wavelength.

The plurality of signals received from the various sensors and devices described herein above are typically analog signals including, but not limited to, electrical voltages and currents. In various aspects, the acquisition unit 234 may enable the transmission of the analog signals to one or more analog-to-digital converters (ADCs) to convert the analog signals into digital signals for subsequent processing by the processing unit 236. FIG. 11 is a schematic diagram of a circuit 1100 illustrating the arrangement of various electrical devices and components of the sensor head 204. In one aspect, the analog signals encoding the intensity of light detected by the first light detector 222 and the second light detector 224 may be received by a first ADC 1102.

In various aspects, the analog signals produced by the light detectors 222/224 and various monitor sensors may be digitized using at least one 24-bit Sigma-Delta ADC. Referring again to FIG. 11, analog signals encoding the measurements from time-sensitive sensors may be digitized using a high-speed 24-bit Sigma-Delta ADC 1102 in one aspect. In this aspect, time-sensitive sensors include sensors associated with the production and detection of light pulses characterized by potentially rapidly-changing signals. Non-limiting examples of time-sensitive sensors of the system 200 include: first and second light detectors 1118/1120, and first and second monitor photodiodes 904/906. In another aspect, analog signals encoding the measurements from less time-sensitive sensors may be digitized using a low-speed 24-bit Sigma-Delta ADC 1104. In this other aspect, the less time-sensitive sensors include sensors associated with monitoring system conditions characterized by typically slow-changing signals including, but not limited to, temperatures of various system components and/or regions. Non-limiting examples of less time-sensitive sensors of the system 200 include: a first and second temperature sensor 1106/1108 configured to monitor the temperatures of the light detectors 222/224 and light sources 218/220, respectively, and a third temperature sensor 1128 configured to monitor a temperature of the housing 600 of the sensor head 204.

In various aspects, the acquisition unit 234 may be further configured to enable synchronous detection of light by detectors 222/224. Without being limited to any particular theory, synchronous detection methods are thought to reject noise from the detector signals associated with the detection of light produced by the light sources 118/120 and fluorescence produced by the exogenous fluorescent agents within the tissues of the patient 202 by distinguishing the detector signals from noise associated with the detection of ambient light or other sources of interference.

Figure 12:
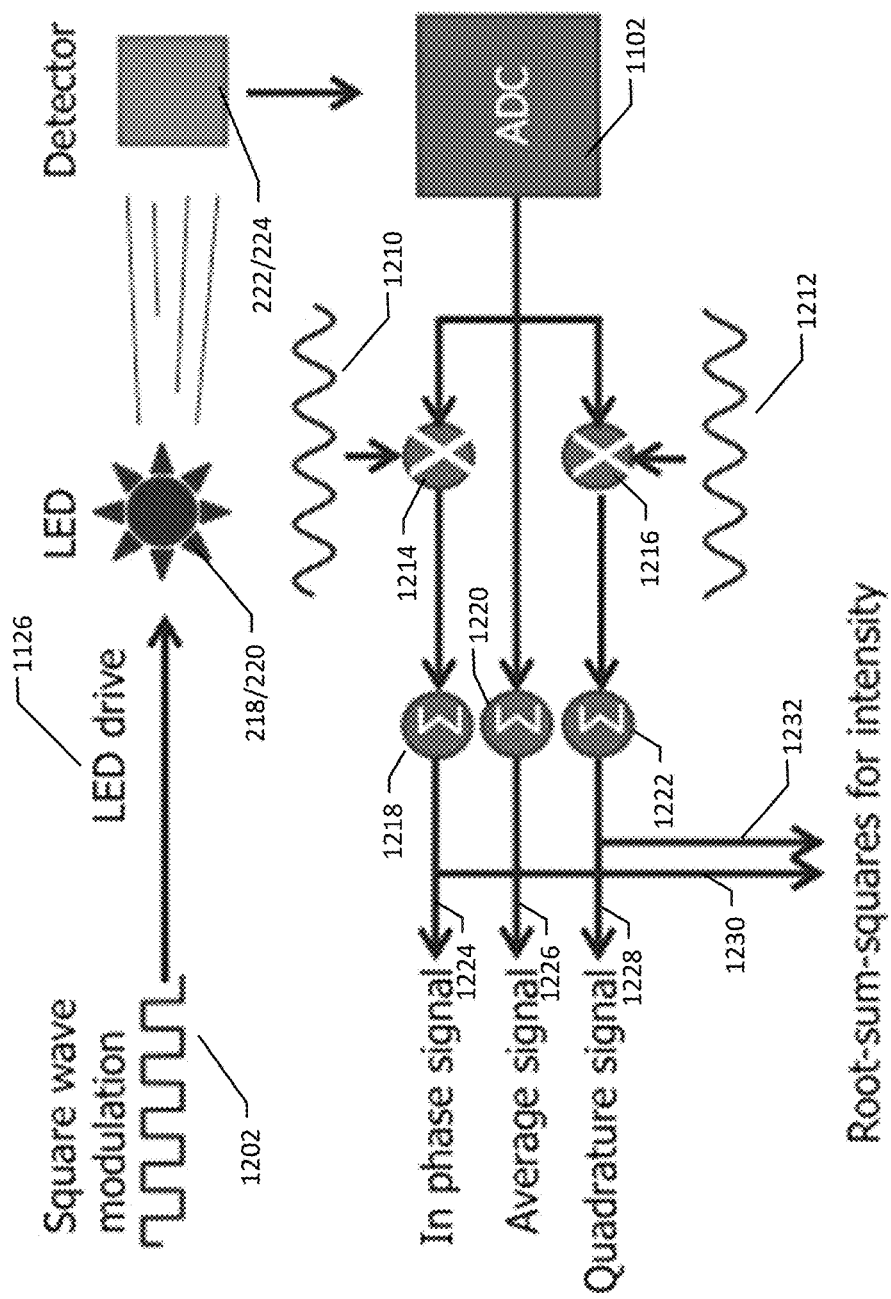
FIG. 12 is a schematic illustration of light signal modulation and demodulation by the sensor head in one aspect.

FIG. 12 is a schematic illustration of a synchronous detection method in one aspect. Referring to FIG. 11 and FIG. 12, the waveform generator/FPA 1122 may generate a digital square wave 1202 that is received by the DAC 1124, and the resulting analog-converted square wave is received by the LED current source 1126. The resulting current produced by the LED current source 1126, also characterized by a waveform proportional to the analog-converted square wave drives LED light sources 218/220. The light produced by LED light sources 218/220, after passing through the tissues of the patient 202 are detected, along with the fluorescence produced by the endogenous fluorescent agent, by the light detectors 222/224 and are digitized by the high-speed ADC 1102.

Referring again to FIG. 11 and FIG. 12, the digital square wave 1202 generated by the waveform generator/FPA 1122 may also be converted by a DAC 1110 (see FIG. 11) to an in-phase reference sine wave 1210 and an out-of-phase/quadrature reference cosine wave 1212. In an aspect, the digitized detector signals from the ADC 1102 and the in-phase reference sine wave 1210 may be sampled and subjected to signed multiplication at a first multiplier 1214 to generate a plurality of in-phase modulated signals. In addition, the digitized detector signals and the quadrature reference cosine wave 1212 may be sampled and subjected to signed multiplication at a second multiplier 1216 to generate a plurality of quadrature (out-of-phase) modulated signals. In this aspect, the acquisition unit 234 may delay the samples from the reference waves 1210/1214 by an amount equivalent to the relative delay between the DAC 1124 generating the reference waves 1210/1214 and the ADC 1102 digitizing the detector signals to synchronize the reference waves 1210/1214 to the detector data being acquired.

Referring again to FIG. 12, the in-phase modulated signals may be summed in a first accumulator 1218 to generate an in-phase intensity signal 1224. Similarly, the quadrature modulated signals may be summed in a third accumulator 1222 to generate a quadrature intensity signal 1228. The raw digitized detector signal may also be summed in a second accumulator 1220 to generate an average intensity signal 1226. In addition, the in-phase intensity signal 1224 and the quadrature intensity signal 1228 may be root-sum squared to generate a magnitude signal 1230.

Without being limited to any particular theory, the integration interval of the accumulators 1218/1220/1222 may correspond to an integer number of modulation cycles (corresponding to cycles of the digital square wave 1202) to avoid a bias on the measured signal. The phase accumulators 1218/1220/1222 used to control the synchronous detection operates on integer numbers, but the sample clock frequency and the modulation frequency are not integer-divisible, so the number of cycles is not exactly an integer. However, the error associated with this mismatch may be minimized by adjusting the actual modulation frequency to match as closely as possible with the achievable sampling intervals and allocating an appropriate number of bits to the phase accumulator. In one aspect, the error associated with the mismatch between the modulation frequency and the sampling intervals may be on the order of about one part in $10^6$.

In one aspect, the digital square wave 1202 used to modulate the LED light sources 218/220 and to enable synchronous detection method as described herein above is produced at a frequency of about 1 kHz. Without being limited to any particular theory, a square wave was selected as the modulating waveform to enable an enhancement in signal to noise ratio (SNR), as compared to a pure sinusoidal wave as the modulating waveform for the same peak power level.

In another aspect, the acquisition unit 234 may be further configured to enable demodulation of the in-phase intensity signal 1224, average intensity signal 1226, and quadrature intensity signal 1228. In one aspect, the acquisition unit 234 may pick out each component at the fundamental harmonic, which is characterized by an amplitude that is $(4/\pi)$ times larger than the amplitude of the square wave 1202 used to modulate the intensity signals 1224/1226/1228. In various aspects, to reject 50/60 Hz electrical noise generated by the alternating current electrical power sources, and corresponding 100/120 Hz optical noise generated by ambient light sources powered from those electrical power sources, the integration period of the accumulators 1218/1220/1222 may be selected to be a multiple of 100 ms. In these various aspects, this selected integration period ensures that integration by the accumulators 1218/1220/1222 occurs over an integer number of cycles for the 50, 60, 100, and 120 Hz signals.

iv) Processing Unit

Figure 13:
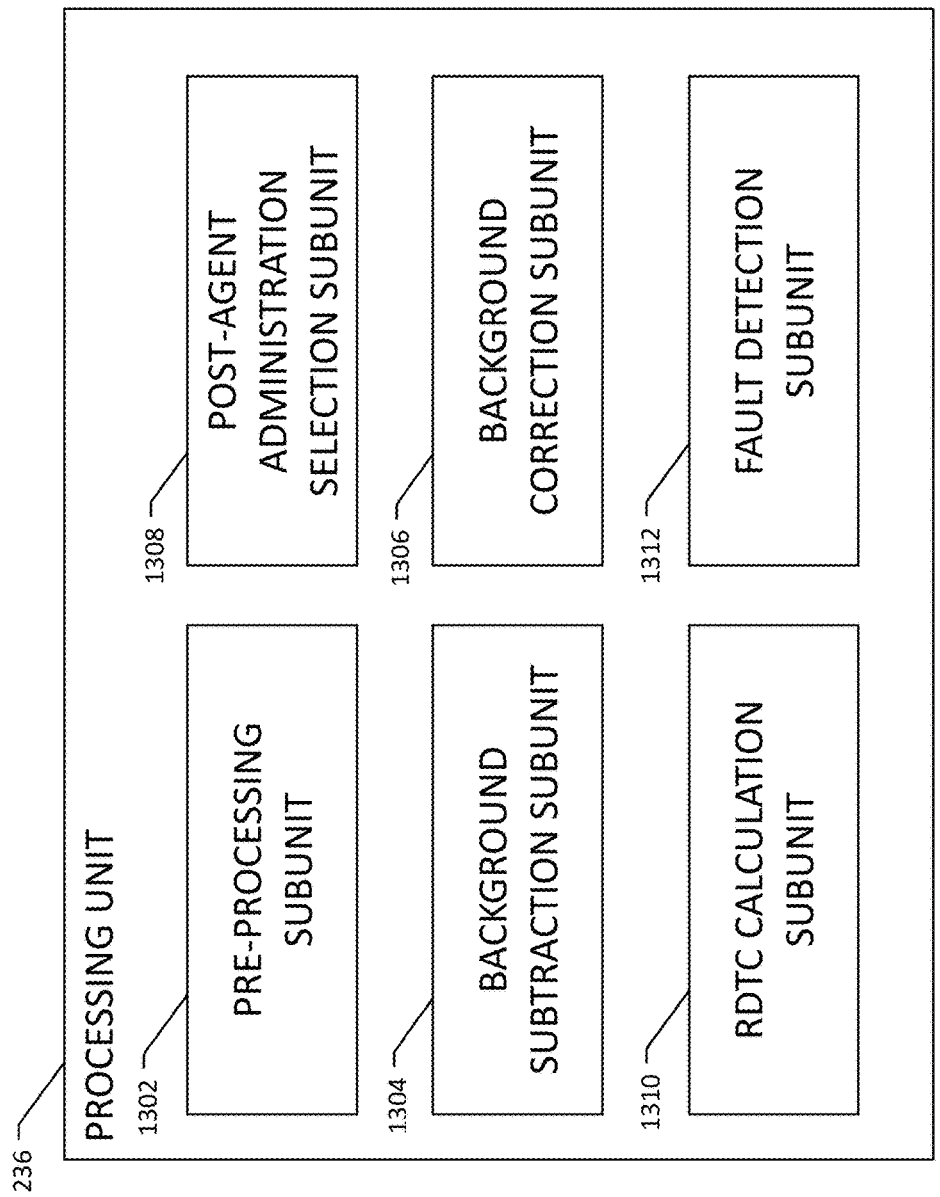
FIG. 13 is a block diagram illustrating the subunits of a processing unit in one aspect.

Referring again to FIG. 2, the controller 212 may further include a processing unit 236 configured to apply corrections to the demodulated detector signals and to transform a selected portion of the corrected detector signals into a measure of renal function in various aspects. FIG. 13 is a block diagram illustrating the subunits of the processing unit 236 in an aspect. Referring to FIG. 13, the processing unit 236 may include a pre-processing subunit 1302 configured to determine and correct the detector signals to remove signal artifacts associated with a variety of confounding effects including, but not limited to, physiologically-induced signal variations, variations in power supplied to the light sources 218/220, non-linearities in detector response, ambient temperature variation, and tissue heterogeneity. The processing unit 236 may further include a background subtraction subunit 1304 configured to remove the portion of the detector signals attributable to background factors such as autofluorescence of the tissues and/or leakage of light at the excitation wavelength through the optical filter 244 of the second light detector 224. The processing unit 236 may additionally include a background correction subunit 1306 configured to enable a method of applying a background correction method to remove the effects of dynamic changes in the background signal related to changes in autofluorescence and/or the leak-through of excitatory-wavelength light to the second light detector 224 configured to detect emission-wavelength light only, and to apply the background correction to the first detector, turning $DR_{ex,meas}$ into $DR_{ex,photons}$. The processing unit 236 may further include a post-agent administration selection subunit 1308 configured to select a portion of the detector data associated with the post-equilibration period for subsequent analysis to determine renal function of the patient. The processing unit 236 may further include an RDTC calculation subunit 1310 configured to transform the detector signals obtained over the post-equilibration period to produce a renal decay time constant indicative of the renal function of the patient. The processing unit 236 may also include a fault detection subunit 1312 configured to monitor the magnitudes of the detector signals to detect any malfunctions of the system.

Pre-Processing Subunit

In one aspect, the raw signals corresponding to the light intensity detected by light detectors 222/224 corresponding to illumination by the first light source 218 and the second light source 220 at the excitation and emission wavelength, respectively, are pre-processed using various modules of the pre-processing subunit 1302 to remove the effects of a plurality of confounding factors from the raw signals, resulting in signals that more accurately reflect the underlying specific signals of interest.

By way of several non-limiting examples, the intensity of light produced by a light source may vary due to one or more of a plurality of factors including, but not limited to: fluctuations in the electrical current supplied to the light source and variations in the ambient temperature of the light source. Light characterized by two or more wavelengths emanating from the same source aperture of the sensor head may not share the same path to the same detector. The detectors may have thermally-dependent sensitivity and gain. Further, the optical filter associated with the second light detector 224 may have temperature-dependent transmission properties.

Figure 22A:
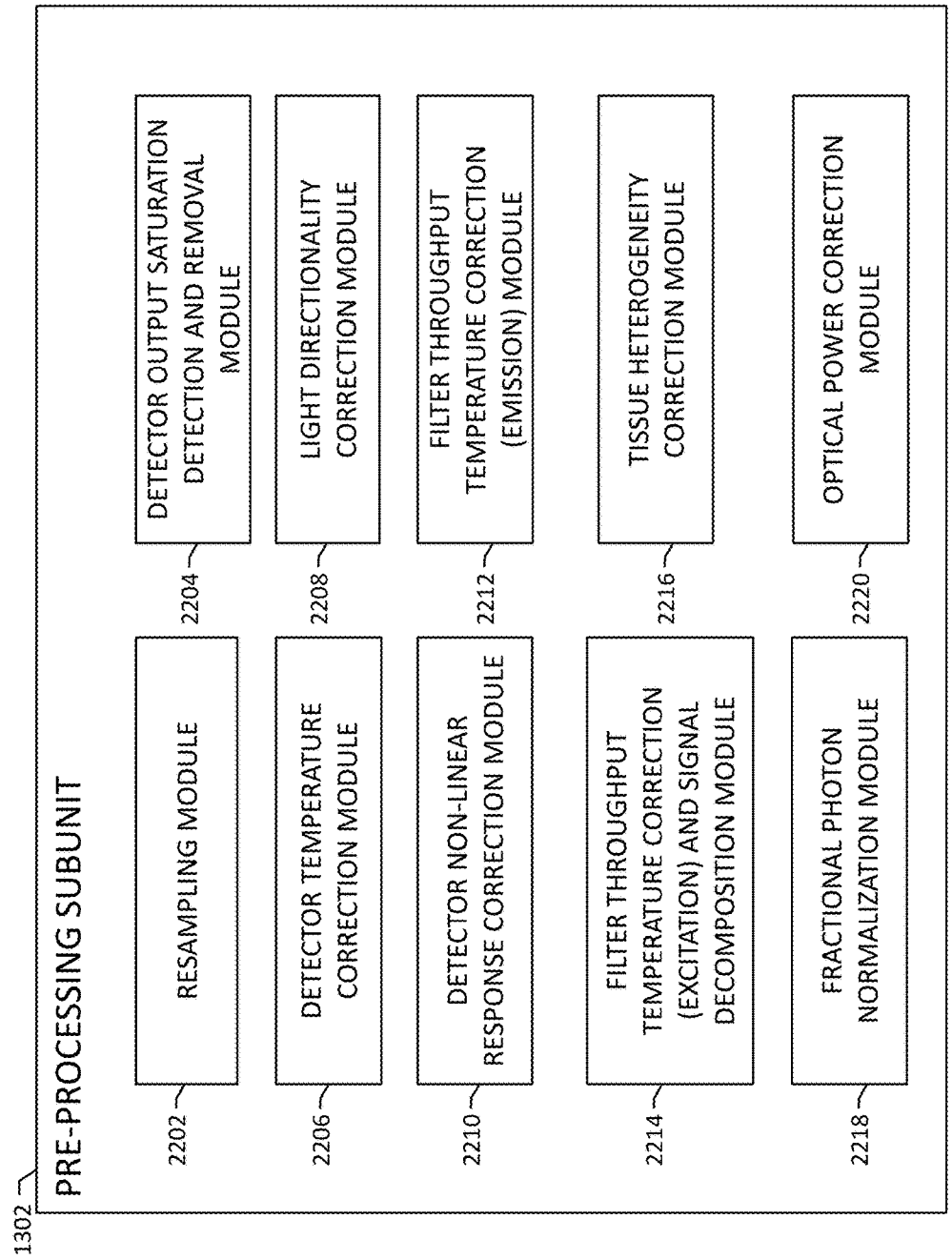
FIG. 22A is a block diagram illustrating a plurality of modules of a pre-processing subunit in one aspect.
Figure 22B:
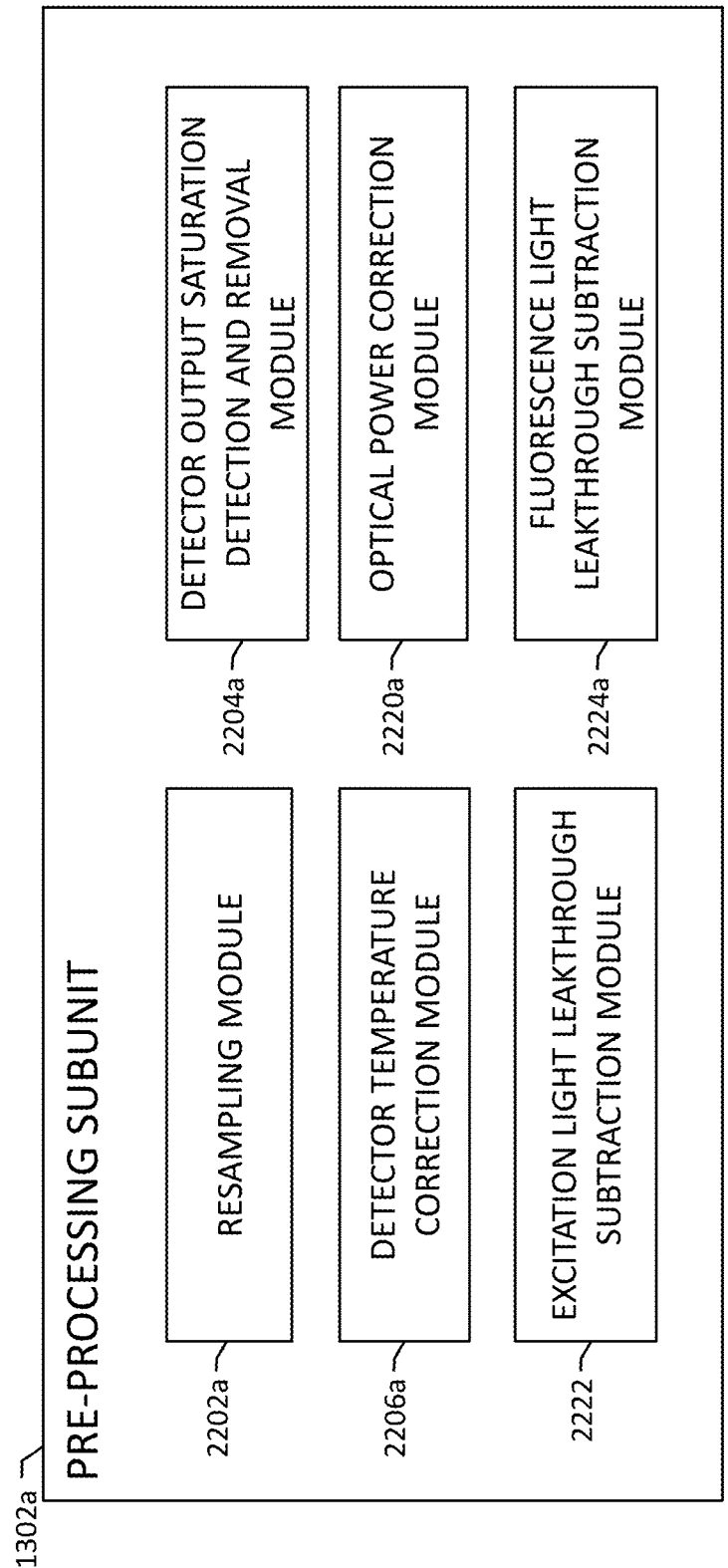
FIG. 22B is a block diagram illustrating a plurality of modules of a pre-processing subunit in a second aspect.

In one aspect, the pre-processing subunit 1302 is configured to process the raw signals corresponding to light intensities detected by the first and second light detectors 222/224 in order to remove one or more of the measurement errors associated with the devices and elements of the system 200 and patient-specific factors including, but not limited to, the plurality of factors described above. FIG. 22A is a block diagram illustrating the modules of the pre-processing subunit 1302 in one aspect. FIG. 22B is a block diagram illustrating the modules of the pre-processing subunit 1302a in a second aspect.

In one aspect, illustrated in FIG. 22A, the pre-processing subunit 1302 1) resamples the signals using the methods of the resampling module 2202 as described below, 2) removes saturated detector signals using the methods of the detector output saturation detection and removal module 2204 as described below, 3) corrects for temperature-dependent detector gain using the methods of the detector temperature correction module 2206 described below, 4) corrects the signals for instrument light directionality using the methods of the light directionality correction module 2208 described below, 5) corrects the signals for filter throughput and temperature-dependent variation of fluorescence light using the methods of the filter throughput temperature correction (emission) module 2212 described below, 6) corrects for tissue heterogeneity using the methods of the tissue heterogeneity correction module 2216 described below, 7) corrects the signals for filter throughput and temperature-dependent variation of excitation light and signal decomposition using the methods of the filter throughput temperature correction (excitation) module and signal decomposition module 2214 as described below, 8) corrects for optical power variation using the methods of the fractional photon normalization module 2218 as described below.

In one aspect, illustrated in FIG. 22B, the pre-processing subunit 1302a calculates signal magnitudes using the methods of the detector temperature correction module 2206a as described below, resamples the signals using the methods of the resampling module 2202a as described below, removes saturated samples using the methods of the detector output saturation detection and removal module 2204a as described below, corrects the signals for temperature-dependent detector gain using the methods of the detector temperature correction module 2206a described below, corrects the signals for optical power variation using the methods of the fractional photon normalization module 2218a as described below, corrects for excitation light leakthrough onto the measured fluorescence signal using the filter throughput temperature correction (excitation) module and signal decomposition module 2214a as described below, and corrects for fluorescence light leakthrough onto the measured excitation diffuse reflectance signal using the filter throughput temperature correction (emission) module 2212a as described below.

Resampling Module

Referring to FIG. 22A and FIG. 22B the pre-processing subunit 1302/1302a in various aspects includes a resampling module 2202/2202a configured to reduce signal variations associated with physiological processes of the patient 202 including, but not limited to, heartbeat and breathing. Typically, an acquisition sequence is characterized by alternating interval of illumination at the excitation and emission separated by intervals of no illumination (i.e. dark intervals). Although both illumination intervals (excitation/emission) are time-stamped with the same timestamp value as described above, the dark interval between the excitation and emission illumination intervals results in a separation interval between the excitation and emission illumination intervals. Without being limited to any particular theory, if the separation interval associated with an acquisition sequence is on the order of a separation interval between physiological events, such as heartbeats or respiration, physiological noise may be introduced to the signals. In various aspects, this physiological noise may be reduced by resampling the signals associated with the excitation and emission illumination to overlap prior to subsequent processing of the signals.

By way of non-limiting example, a sample sequence may include a 100 ms dark interval, a 100 ms interval of illumination at the excitatory wavelength, a second 100 ms dark interval, and a 100 ms interval of illumination at the emission wavelength. Each sample packet is logged with a single timestamp, and each sample packet is separated by a 400 ms interval. Because physiological signal variations, such as from heartbeats, occur on this same timescale, the 200 ms difference between signal acquisition associated with the excitatory and emission wavelengths becomes apparent in the signals. This physiological signal noise may be reduced using the pre-processing subunit 1302 by first resampling the signals associated with illumination at the excitatory and emission wavelength illumination to overlap prior to performing any additional signal processing as described below. In this non-limiting example, the signals associated with illumination at the excitatory wavelength may be shifted forward by 100 ms and the signals associated with illumination at the emission wavelength may be shifted backwards by 100 ms, resulting in an overlap of the signals.

In various aspects, the resampling module 2202 performs resampling as described above on signals detected by both the first and second detectors 222/224. In one aspect, the resampling module 2202 functions as a form of low-pass filter.

Detector Output Saturation Detection and Removal Module

Referring again to FIG. 22A and FIG. 22B the pre-processing subunit 1302/1302a in various aspects includes a detector output saturation detection and removal module 2204/2204a configured to detect and remove signal values that fall outside the detection range of the light detectors 222/224. In one aspect, the pre-processing subunit 1302 compares the detected signals to the maximum ADC signal. If any signal falls within a threshold range of the maximum ADC signal using the average or peak signal value, the detector output saturation detection and removal module 2204 identifies and removes that value from further processing.

Detector Temperature Correction Module

Referring again to FIG. 22A and FIG. 22B the pre-processing subunit 1302/1302a in various aspects includes a detector temperature correction module 2206/2206a configured to enable a temperature correction to compensate for the thermal sensitivity of the light detectors 222/224. In one aspect, the intrinsic detector gain for a silicon photomultiplier (SPM) device typically used as a light detector is proportional to the difference between the device breakdown voltage and the bias voltage applied by the bias voltage generator 1112 (see FIG. 11), referred to herein as an overvoltage. In this aspect, the breakdown voltage varies with temperature in a well-characterized manner. In one aspect, the temperature correction accounts for both this internal detector gain variation and additionally temperature-related variation in the photon detection efficiency.

In one aspect, the temperature correction may be a scaling correction applied to the detector measurements in which the scaling correction is based on a measured detector temperature. In an aspect, the measured light detector signals may be divided by the calculated gain $G(t)$ to remove the temperature dependency. The scaling correction $G(t)$ may be calculated according to Eqn. (2):

$$G(T) = C_v \cdot V_{bias} - V_{breakdown}(1 + C_T)^{T-T_0} \qquad \text{Eqn. (2)}$$

In Eqn. (2), the monitor temperature T is obtained from a first temperature sensor 1106 (see FIG. 11) configured to monitor the temperature of the sensors 222/224. The bias voltage ($V_{bias}$) may be measured by the bias voltage generator 1112. The breakdown voltage ($V_{breakdown}$) and reference temperature ($T_0$) are constants specific to the particular light detector device included in the system 200. By way of non-limiting example, if the light detectors 222/224 are silicon photomultiplier (SPM) devices, $V_{breakdown}$ may be 24.5 V and $T_0$ may be 21 degrees C. In another aspect, the coefficients $C_v$ and $C_T$ used in Eqn. (2) may be derived empirically based on measurements obtained using a constant phantom over an ambient temperature ranging from about 18 degrees C. to about 26 degrees C.

In another aspect, the temperature portion of the gain correction is determined by the Eqns. (3)-(5).

$$G_{useCase} = C_v \cdot V_{bias_{measured}} - V_{breakdown}(1 + C_T)^{T_{measured}-T_0} \qquad \text{Eqn. (3)}$$

$$G_{nominal} = C_v \cdot V_{bias_{nominal}} - V_{breakdown}(1 + C_T)^{T_{nominal}-T_0} \qquad \text{Eqn. (4)}$$

$$G_{correction} = \frac{G_{useCase}}{G_{nominal}} \qquad \text{Eqn. (5)}$$

This gain correction can be applied to each of the signal magnitudes as measured by the first and second light detectors 222/224 as follows:

$$SPMmagnitude_{corrected} = \frac{SPMmagnitude}{G_{correction}} \qquad \text{Eqn. (6)}$$

In an aspect, the magnitudes of the measurements from each detector and monitor photodiode are calculated from the root sum-squares of the in-phase magnitude signals 1230 (I) and quadrature magnitude signals 1232 (Q) according to Eqn. (1):

$$M = \sqrt{I^2 + Q^2} \qquad \text{Eqn. (1)}$$

The signal magnitudes from the light detectors 222/224 calculated using Eqn. (1) are normalized by the monitor photodiode magnitude for each measurement set corresponding to the measurements obtained during illumination by one of the LED light sources 218/220 at either the excitation or emission wavelength. Because both monitor photodiodes 904/906 may positioned in the same source well 902 as both LED light sources 218/220 (see FIG. 9), the average of the two monitor photodiode magnitudes from the corresponding measurement set is used.

In an aspect, the in-phase intensity signal 1224, quadrature intensity signal 1228, and average intensity signal 1226 (see FIG. 12) are further processed for the number of accumulated samples and ADC scaling such that the intensity signals 1224/1226/1228 are returned as fraction of the full range of the high-speed ADC 1102 (i.e. ranging from a minimum of 0 to a maximum of 1). The measurements of the monitor photodiodes 904/906 (see FIG. 11) are similarly scaled as a fraction of the full range of the low-speed ADC 1104.

In one aspect, $G_{correction}$ may incorporate a power correction to correct for the effects of fluctuations in the LED power supply. In this aspect, the signals from the first monitor photodiode 904 and the second monitor photodiode 906 are calibrated by measuring optical output power with a power meter as light intensities from the light sources 218/220 are varied. The calibration coefficients for each light source 218/220, $C_{source1}$ and $C_{source2}$, are calculated as detector-measured milliWatts per recorded monitor photodiode signal value. $C_{source1}$ and $C_{source2}$ are used to determine the absolute light output into tissue at each wavelength.

Referring again to FIG. 22B, the detector temperature correction module 2206a corrects signal magnitudes for the varying intensity of the LEDs by normalizing the temperature-corrected detected signals using the LED output signal $PD_{magnitude}$ measured by the first monitor photodiode 904 and/or the second monitor photodiode 906. In this case, the $G_{correction}$ variable for each light source 218/220 from above is amended as follows:

$$G_{correction} = \frac{G_{useCase}}{G_{nominal}} * PD_{magnitude} \qquad \text{Eqn. (7)}$$

Light Directionality Correction Module

Referring again to FIG. 22A, the pre-processing subunit 1302 in this aspect includes a light directionality correction module 2208 configured to enable a correction to variations in the detected signals associated with differences in the scattering and absorption of light of different wavelengths through the tissues of the patient 202 during data acquisition. In one aspect, a correction term for light directionality may be measured by acquiring data from one or more homogeneous tissue phantoms and using a sensor configuration in which no emission filters are present. The ratio of the signals detected by the first light detector 222 (Det1) and the signals detected by the second light detector 224 (Det2) measured are used to determine a coefficient $G_{ex}$ or $G_{em}$ for signals obtained in association with illumination by light at the excitation and emission wavelengths, respectively. The coefficients are used to modify the signal detected by the first light detector 222. In one aspect, the correction of the signals acquired in a homogeneous medium by the first light detector 222 using the coefficients $G_{ex}$ or $G_{em}$ render the signals measured by the first and second detectors 222/224, as equivalent to within 20% of one another. In other aspects, the correction of the signals acquired in a homogeneous medium by the first light detector 222 using the coefficients $G_{ex}$ or $G_{em}$ render the signals measured by the first and second detectors 222/224 as equivalent to within about 10%, to within about 5%, to within about 2%, and to within about 1%.

Detector Non-Linear Response Correction Module

Referring again to FIG. 22A, the pre-processing subunit 1302 in this aspect includes a detector non-linear response correction module 2210 configured to enable a correction to variations in the detected signals associated with non-linear response of the detectors. In this aspect, a calibration curve based on average data may be used to scale the magnitude data obtained by the detectors 222/224.

Filter Throughput Temperature Correction (Emission) Module

Referring again to FIG. 22A, the pre-processing subunit 1302 in this aspect includes a filter throughput temperature correction (emission) module 2212 configured to enable a correction to variations in the detected signals associated with temperature-dependent optical properties of the optical filter 244 associated with the second light detector 224 during emission-wavelength illumination. In this aspect, the signals Det2 detected by the second light detector 224 may be corrected according to Eqn. (8):

$$Det2 = \frac{Det2 - Det2(C_{emF,slopeT}(T - T_{nom}))}{C_{emF,nom}} \qquad \text{Eqn. (8)}$$

In various aspects, the signal Det2 measured by the second light detector 224 may be monitored while ambient temperature is cycled over a range including the operating temperature range or a large enough subset of the range to adequately determine the temperature-dependence of the emission filter. These data are acquired with the optical filter 244 installed on the second light detector 224 from a homogeneous, non-fluorescent phantom. Further, simultaneous measurements are monitored from the first light detector 222, and a ratio of the measurements Det2/Det1 is determined. The nominal filter coefficient $C_{emF,nom}$ is calculated as the nominal ratio of Det2/Det1 obtained at a nominal operating temperature $T_{nom}$. In this aspect, the coefficient $C_{emF,slopeT}$ is obtained from the slope of Det2/Det1 obtained over a range of ambient temperatures during emission-wavelength illumination of the homogeneous, non-fluorescent phantom.

Tissue Heterogeneity Correction Module

Referring again to FIG. 22A, the pre-processing subunit 1302 in this aspect includes a tissue heterogeneity correction module 2216 configured to enable a correction to variations in the detected signals associated with heterogeneity of the tissues intervening between the first region 206 illuminated by light sources 218/220 and the second and third regions 208/210 at which the light detectors 222/224 are positioned. In this aspect, the signal Det1 corrected for light directionality by the light directionality correction module 2208 and the signal Det2 corrected for filter effects by the filter throughput temperature correction (emission) module 2212 are used to calculate $C_{hetero}$, a coefficient to correct for tissue heterogeneity, according to Eqn. (9):

$$C_{hetero} = Det2/Det1 \qquad \text{Eqn. (9)}$$

Filter Throughput Temperature Correction (Excitation) and Signal Decomposition Module Referring again to FIG. 22A, the pre-processing subunit 1302 in this aspect includes a filter throughput temperature correction (excitation) module and signal decomposition module 2214 configured to enable a correction to variations in the detected signals associated with temperature-dependent optical properties of the optical filter 244 associated with the second light detector 224 during excitation-wavelength illumination. In this aspect, because the emission filter is configured to block light at the excitation wavelength, the filter throughput temperature correction (excitation) module and signal decomposition module 2214 performs a correction to variance to the amount of excitation light leakthrough due to temperature-related changes in the optical properties of the optical filter 244. Further, the filter throughput temperature correction (excitation) module and signal decomposition module 2214 enables corrections of the signals measured by the first light detector 222 during excitation-wavelength illumination due to the presence of fluorescence induced by the excitation-wavelength illumination superimposed over the portion of the signal associated with the excitation-wavelength illumination.

In this aspect, the effects of temperature-dependent variation on leakthrough of excitation-wavelength by the optical filter 244 are calculated as expressed in Eqn. (10):

$$C_{exLT} = C_{exLT,nom} + C_{exLT,slopeT}(T - T_{nom}) \qquad \text{Eqn. (10)}$$

In this aspect, $C_{exLT,nom}$ is calculated from the ratio of signals Det1 and Det2 measured from a homogeneous, non-fluorescent phantom at the nominal operating temperature $T_{nom}$ during excitation-wavelength illumination. $C_{exLT,slopeT}$ is calculated as the slope of the signal Det2 measured from a homogeneous, non-fluorescent phantom at a range of operating temperatures T during emission-wavelength illumination.

In this aspect, the filter throughput temperature correction (excitation) module and signal decomposition module 2214 further performs a signal extraction to isolate portions of the detected signals associated with diffuse reflectance of the excitation-wavelength illumination and fluorescence. $DR_{ex2}$, which is the amount of excitation light impingent on the second light detector 224 in the absence of an optical filter 244, is not measurable, due to the presence of the optical filter 244. Further, the signal Det1 measured by the first light detector 222 is a composite signal from both diffuse reflectance of the excitation-wavelength illumination $DR_{ex1}$ and fluorescence Flr1. $C_{Hetero}$ is obtained using the tissue heterogeneity correction module 2216 as described above. The underlying signals are extracted by use of the following system of equations:

$$Det_2 = C_{exLT} DR_{ex2} + Flr2 \qquad \text{Eqn. (11)}$$

$$Det_1 = DR_{ex1} + Flr_1 \qquad \text{Eqn. (12)}$$

$$Flr_2 = C_{Hetero} Flr_1 \qquad \text{Eqn. (13)}$$

$$DR_{ex2} = C_{Hetero} DR_{ex1} \qquad \text{Eqn. (14)}$$

In this aspect, $Flr_2$ is determined by solving the above system of equations using only measurable signals Det1 and Det2 as demonstrated below:

$$Det_2 = C_{exLT} C_{Hetero} DR_{ex1} + Flr_2 \qquad \text{Eqn. (15)}$$

$$Det_2 = C_{exLT} C_{Hetero}(Det_1 - Flr_1) + Flr_2 \qquad \text{Eqn. (16)}$$

$$Det_2 = C_{exLT} C_{Hetero} Det_1 - C_{exLT} C_{Hetero} Flr_1 + Flr_2 \qquad \text{Eqn. (17)}$$

$$Det_2 - C_{exLT} C_{Hetero} Det_1 = Flr_2(1 - C_{exLT}) \qquad \text{Eqn. (18)}$$

$$Flr_2 = \frac{Det_2 - C_{exLT} C_{Hetero} Det_1}{1 - C_{exLT}} \qquad \text{Eqn. (19)}$$

In this aspect, once Flr2 is obtained as described above, the other signals $Flr_1$, $DR_{ex1}$, and $DR_{ex2}$ may be readily obtained through insertion into the system of equations (Eqns. (11)-(14)) presented above.

Fractional Photon Normalization Module

Referring again to FIG. 22A, the pre-processing subunit 1302 in this aspect includes a fractional photon normalization module 2218 configured to convert the detector signals, after preprocessing as described above, into units of fractional photons for use in subsequent background subtraction and intrinsic fluorescence correction algorithms as described herein. In this aspect, the detector signals may be converted to photocurrent by reversing the scaling associated with the ADC and the transimpedance amplifier used to acquire the detected signals to obtain the signals in units of photocurrents. Once photocurrent is obtained, a detector responsivity supplied by the light detector's manufacturer is used to convert the detector photocurrents to units of Watts. The detector signals in Watts are then ratioed to the source power in Watts as measured by additional light detectors 226 used to monitor the output of the light sources 218/220 to obtain the number of fractional photons detected.

Optical Power Correction Module

Referring again to FIG. 22A and FIG. 22B, the pre-processing subunit 1302/1302a in this aspect includes a fractional photon normalization module 2218/2218a configured to convert the detector signals, after preprocessing as described above, into units of fractional photons for use in subsequent background subtraction and intrinsic fluorescence correction algorithms as described herein. In this aspect, the detector signals may be converted to photocurrent by reversing the scaling associated with the ADC and the transimpedance amplifier used to acquire the detected signals to obtain the signals in units of photocurrents. Once photocurrent is obtained, a detector responsivity supplied by the light detector's manufacturer is used to convert the detector photocurrents to units of Watts. The detector signals in Watts are then ratioed to the source power in Watts as measured by additional light detectors 226 used to monitor the output of the light sources 218/220 to obtain the number of fractional photons detected.

Excitation Light Leakthrough Subtraction Module

Referring again to FIG. 22B, the pre-processing subunit 1302a in this aspect includes a fractional photon normalization module 2222 configured to perform an excitation leakthrough subtraction on the $Flr_{meas}$ signal. To arrive at a fluorescence signal due only to fluorescent photons ($Flr_{photons}$), an excitation leakthrough subtraction is performed. To remove the contribution of excitation light, the excitation leakthrough is taken to be a fraction of the diffuse reflectance excitation ($DR_{ex_{meas}}$) signal, where a universal calibration factor, $C_{ExLT}$, determines the fraction of the signal to subtract from $Flr_{meas}$ as expressed below:

$$ExLT = C_{ExLT} * DR_{ex_{meas}}$$

where $C_{ExLT}$ is a calibration factor that is obtained by computing the ratio between the excitation light detected by both detectors on a non-fluorescing optical phantom as described below:

$$C_{ExLT} = \frac{Flr_{meas}}{DR_{ex_{meas}}}$$

This signal is then subtracted from $Flr_{meas}$ to provide a fluorescence signal due only to fluorescent photons as expressed below:

$$Flr_{photons} = Flr_{meas} - ExLT$$

Fluorescence Light Leakthrough Subtraction Module

Referring again to FIG. 22B, the pre-processing subunit 1302a in this aspect includes a fluorescence light leakthrough subtraction module 2224a configured to perform a fluorescence leakthrough subtraction on the $Flr_{meas}$ signal. To obtain the diffuse reflectance, defined herein as the excitation signal due to only excitation photons ($DRex_{photons}$), a fluorescence leakthrough subtraction is performed. To remove the fluorescence leakthrough, a calibration factor, $C_{FlrLT}$, was determined based on the relationship between the amount of fluorescence leakthrough observed on a database of human subject data and tissue heterogeneity as measured by the relationship between the diffuse reflectance, emission signals $$\left(\frac{DRemFilt}{DRem}\right).$$

The relationship is a linear relation as expressed below:

$$C_{FlrLT} = p1 * \left(\frac{DRem}{DRemFilt}\right) + p2$$

where p1 and p2 are approximately 0.61 and 0.01, respectively, in one aspect, as determined by the above-mentioned relationship. In another aspect, p1 and p2 may assume any other value without limitation as defined by the above relationship.

The $DRex_{photons}$ signal is then calculated by subtracting this fraction of measured fluorescence from the diffuse reflectance excitation signal, as follows:

$$DRex_{photons} = DR_{ex_{meas}} - Flr_{meas} * C_{FlrLT}$$

b) Baseline Subtraction Subunit

Referring again to FIG. 13, the processing unit 236 further includes a baseline subtraction subunit 1304. In an aspect, the baseline subtraction subunit 1304 subtracts a baseline signal from the light detector measurements to correct for the effects of autofluorescence and light leakage. The baseline period, as used herein, refers to an initial time period of measurements obtained prior to injection of the exogenous fluorescent agent. During the baseline period, the fluorescence signal measured by the system 200 may be assumed to be associated with tissue autofluorescence and/or excitation light from the LED light sources 218/220 leaking through the optical filter 244 of the second light detector 224. In an aspect, the average signal measured during the baseline period, referred to herein as a baseline signal, may be subtracted from subsequent fluorescence measurements to yield a measurement associated solely with the fluorescence produced by the exogenous fluorescent agent within the tissues of the patient.

In another aspect, the corrections for excitation light leakthrough and autofluorescence may be implemented in cooperation with the background correction subunit 1306. In this other aspect, rather than subtracting an average signal measured during the baseline period, the background correction subunit 1306 may dynamically calculate the effects of excitation light leak-through and autofluorescence at each data acquisition cycle. As a result, subtraction of the effects of excitation light leak-through may be performed prior to the diffuse reflectance correction described herein below, and a subtraction of the effects of autofluorescence may be updated at each data acquisition cycle by the background correction subunit 1306.

c) Background Correction Subunit

In an aspect, the background correction subunit 1306 may correct the measured fluorescence data to remove the effects of changes to the optical properties (absorption and scattering) of the tissues of the patient 202 during monitoring of renal extraction of an exogenous fluorescent agent within the tissues of a patient. As described herein above, the optical properties of the tissues may change due to any one or more factors including, but not limited to: vasodilation, vasoconstriction, oxygen saturation, hydration, edema, and any other suitable factor within the region of interest monitored by the system, associated with changes in the concentrations of endogenous fluorophores such as hemoglobin, collagen, and melanin.

In one aspect, the background correction subunit 1306 may determine the intrinsic autofluorescence ($IF_{auto}$) signal, representing the emission-wavelength light emitted by endogenous fluorophores within the tissues of the patient during data acquisition. In this aspect, the $IF_{auto}$ signal is obtained from the mean or median of $IF_{bkrnd}$ (the background intrinsic fluorescence data prior to agent injection). The $IF_{bkrnd}$ signal is found as follows:

$$IF_{bkrnd} = \frac{Flr_{bkrnd}}{DR_{ex}^{bkx} DR_{em}^{bkm} DR_{emFilt}^{bkmFilt}}$$

where the coefficients bkx, bkm, and kmFilt are found via a global error surface method.

In one aspect, the values of the powers used in the equation above are determined empirically using a global error surface method. The method in this aspect includes selecting ranges of values for each of the powers (bkx, bkm, bkmFilt) for each of the diffuse reflectance signals ($DR_{ex}$, $DR_{em}$, $DR_{em,filtered}$) selected by a user. In various aspects, the ranges of values for each of the powers may be influenced by any one or more of a variety of factors including, but not limited to: the design of the system 200, including the design of the sensor head 204; the properties of the selected exogenous fluorescent agent such as excitatory/emission wavelengths, absorption efficiency, emission efficiency, and concentration of initial dose in the patient's tissues; the species of the patient 202 and corresponding concentrations of endogenous chromophores; the position of the sensor head 204 on the patient 202; and any other relevant factor.

In one aspect, the method may include choosing a wide range for each coefficient (bkx, bkm, bkmFilt) and conduct a broad search. The error surfaces from this broad search may be analyzed to locate wells in the error surface and the associated ranges for each of the coefficients. The method in this one aspect includes adapting the ranges of each coefficient to include the regions from the broad search within which wells in the error surface were observed and repeating the analysis. This method may be iterated until a suitably fine resolution is achieved that is capable of accurately capturing the minimum error.

Step sizes may be selected at 1404 for the ranges of values selected for each power (bkx, bkm, bkmFilt). In an aspect, the step size for each factor may be selected based on any one or more of at least several factors including, but not limited to: the anticipated sensitivity of the IF values calculated above to changes in each factor; a suitable total number of combinations of powers used to calculate IF considered factors including available computational resources, acceptable data processing times, or any other relevant factors; and any other suitable criterion for step size.

In various aspects, the step sizes may be the same value for all powers (bkx, bkm, bkmFilt). By way of non-limiting example, the step size for all powers may be 0.5. In various other aspects, the step sizes may be constant for all values of a single power (bkx, bkm, bkmFilt), but the step sizes selected for each power may be different between different powers. By way of non-limiting example, the selected step size for bkx may be 0.01 and the selected step size for bkm and bkmFilt may be 0.6. In various additional aspects, the step size within one or more of the powers may vary within the range of values for each power. In these various additional aspects, the step size may be reduced within subranges of values for a power for which the IF calculated above is predicted to be more sensitive to small changes in that power. Non-limiting examples of suitable varying step sizes within a range of values for a single power include: different step sizes selected by a user, random step sizes, a linear increase and/or decrease in step size, a non-linear distribution of different step sizes such as a logarithmic distribution, an exponential distribution, or any other suitable non-linear distribution of step sizes.

The selected ranges of exponents, together with the selected step sizes, may be used to form vectors of potential values of bkx, bkm, bkmFilt. For each combination of exponents amongst all vectors, IF is calculated from the measurements Flr, $DR_{ex}$, $DR_{em}$, and $DR_{em,filtered}$ using the above equation. For each combination of exponents, a plurality of IF values are calculated in which each IF value corresponds to one of the data acquisition cycles By way of non-limiting example, using the vectors of potential exponents listed herein above, a total of 405 (5*9*9) pluralities of IF signals would be calculated.

In an aspect, the plurality of combinations of potential exponents may be evaluated to select one combination of exponents from the plurality to assign for use in subsequent diffuse reflectance corrections calculated using the above equation. An estimate of error of the corrected Flr signal data (i.e. IF signal data calculated using the above equation may be calculated. Any estimate of error may be calculated including, but not limited to, a quantity related to residuals of the IF signal data relative to a curve fit of the IF signal data. Any type of known curve-fitting method may be used to curve-fit the IF signal data including, but not limited to, a single-exponential curve fit. Without being limited to any particular theory, it is thought that the rate of clearance of an exogenous fluorescent agent, such as MB-102, from the kidneys is expected to be a constant exponential decay characterized by the renal decay time constant RDTC.

Intrinsic autofluorescence ($IF_{auto}$) is then simply the mean or median of $IF_{bkrnd}$. The autofluorescence signal, $Flr_{auto}$, is then projected by performing the inverse background diffuse reflectance correction, as follows:

$$Flr_{auto} = IF_{auto} * (DR_{em}^{bkm}/DR_{ex}^{bkx}/DR_{emFilt}^{bkmFilt})$$

This autofluorescence signal, $Flr_{auto}$ is then removed from the measured fluorescence signal, Flr to determine the agent intrinsic fluorescence ($IF_{agent}$) specifically representing the emission-wavelength light emitted by the exogenous fluorescent agent.

Without being limited to any particular theory, the fluorescence measurements obtained by the system 200 that are used to determine renal function include emission-wavelength photons that are detected by the second (filtered) light detector 224. These emission-wavelength photons are emitted by the exogenous fluorescence agent introduced into the tissues of the patient in response to illumination by excitation-wavelength photons. The emission-wavelength photons travel from the fluorescence source (i.e. the exogenous fluorescence agent) to the second (filtered) light detector 224 through third region 210 of the patient's skin. However, the emission-wavelength light that is detected by the second (filtered) light detector 224 may also include autofluorescence emitted by endogenous chromophores such as keratin and collagen within the tissues of the patient, as well as leak-through of excitatory-wavelength light through the optical filter 244 of the second light detector 224. The excitation-wavelength photons that induce fluorescence of the exogenous fluorescent agent are produced by the first light source 218 and are directed into the first region 206 of the patient's skin. If the optical properties of the patient's skin (scattering and/or absorption) varies over the time interval at which the detector data used to determine renal function is acquired (i.e. from a few hours to about 24 hours or more), the accuracy of the fluorescence measurements may be impacted, as discussed previously above.

During each measurement cycle in an aspect, the system 200 may direct light into the first region 206 of the patient's skin with a pulse of emission-wavelength light and a pulse of excitation-wavelength light in an alternating series and may detect all light emerging from the second region of the patients skin using the first (unfiltered) light detector 222 and a portion of the light emerging from the third region 210 of the patient's skin using the second (filtered) light detector 224. The light intensity detected by each combination of excitation and emission wavelength illumination of the first region 206 and detection by the unfiltered/filtered light detectors 222/224 contain information not only about the concentration of the exogenous fluorescent agent in the patient's tissues, but also information about the optical properties of the patient's skin.

TABLE 2

Light Detector Measurements After Temperature and Power Fluctuation Corrections

| Illumination wavelength | First (Reference) Light Detector Unfiltered | Second (Primary) Light Detector Filtered |
|---|---|---|
| Excitation-wavelength | $DR_{ex}$ | Flr |
| Emission-wavelength | $DR_{em}$ | $DR_{em, filtered}$ |

The primary measurement of fluorescence is $Flr_{meas}$, the intensity of fluorescent light measured at the filtered detector.

The diffuse reflectance measurement $Flr_{meas}$ represents the propagation of photons to the non-filtered arm and is composed primarily of excitation photons.

$DR_{em}$ and $DR_{em,filtered}$ represent the propagation of emission-only photons.

Referring to Table 2, light intensity measured by the second (filtered) light detector 224 during illumination by the excitation-wavelength light captures the raw intensity of light emitted by the exogenous fluorescent agents ($Flr_{meas}$) prior to any corrections for tissue optical properties in various aspects. After baseline subtraction corrections as described herein previously, the emission-wavelength light contained in $Flr_{meas}$ is assumed to originate predominantly from the exogenous fluorescent agent, with only minor contributions due to auto-fluorescence by endogenous fluorophores, and is therefore termed $Flr_{agent}$. In an aspect, if no change in the optical properties of the patient's skin is assumed, all autofluorescence contributions would be subtracted off during the baseline correction described herein above.

However, if the optical properties of the patient's skin change during the acquisition of data, slightly more or less of the autofluorescence may emerge from the patient's skin at the emission wavelength, thereby introducing uncertainty into the accuracy of the background subtraction correction performed previously. In addition, varied skin optical properties may further alter the intensity of light at the excitation wavelength reaching the exogenous fluorescent agent, thereby altering the amount of energy absorbed by the exogenous fluorescent agent and the intensity of induced fluorescence from the exogenous fluorescent emitted in response to illumination by the excitation-wavelength light. In various aspects, the remaining three light measurements enable monitoring of the optical properties of the patient's skin and provide data that may be used to adjust for any changes in the optical properties of the patient's skin including the effects of autofluorescence and excitatory-wavelength light bleed-through.

Referring again to Table 2, light intensity measured by the first (unfiltered reference) light detector 222 during illumination by excitation-wavelength light captures a measure of the diffuse reflectance of excitation-wavelength light propagated through the patient's skin ($DR_{ex}$). Although the first light detector 222 is configured to detect both excitation-wavelength and emission-wavelength light, the intensity of the excitation-wavelength light is orders of magnitude higher than the intensity of the emission-wavelength light as a result of the lower efficiency of producing light via fluorescence. In various aspects, the proportion of emission-wavelength light within $DR_{ex}$ is assumed to be negligible. In other aspects, the proportion of emission-wavelength light within $DR_{ex}$ is estimated and subtracted. Without being limited to any particular theory, because the intensity of the excitation-wavelength light directed into the patient's skin is assumed to be relatively constant with negligible losses due to absorption by the exogenous fluorescent agent, and is subject to power corrections as described herein previously, $DR_{ex}$ serves as a benchmark measurement to assess changes in the optical properties of the patient's skin with respect to the excitation-wavelength light.

Light intensity measured by the first (unfiltered reference) light detector 222 during illumination by emission-wavelength light captures a measure of the diffuse reflectance of emission-wavelength light propagated through the patient's skin ($DR_{em}$). Without being limited to any particular theory, because the exogenous fluorescent agent is not induced to emit emission-wavelength light due to the absence of excitation-wavelength illumination during this phase of the data acquisition cycle, and because the intensity of the emission-wavelength light directed into the patient's skin is relatively constant and subject to power corrections as described herein previously, $DR_{ex}$ serves as a benchmark measurement to assess changes in the optical properties of the patient's skin with respect to the emission-wavelength light.

Light intensity measured by the second (filtered) light detector 224 during illumination by emission-wavelength light captures a second measure of the diffuse reflectance of emission-wavelength light propagated through the patient's skin ($DR_{em,filtered}$). In one aspect, $DR_{em,filtered}$ is subject to the same assumptions as $DR_{em}$ as described herein above. In addition, $DR_{em,filtered}$ provides a means of assessing heterogeneity of the tissue's optical properties. Because $DR_{em,filtered}$ is measured by the second light detector 224 configured to detect light emerging from the patient's skin at the third region 210 (see FIG. 2), the intensity of light measured in $DR_{em,filtered}$ has propagated along an optical path through the skin of the patient that is different from the optical path travelled by the light measured in $DR_{em}$. Without being limited to any particular theory, because the distances of the first detector aperture 1004 and second light aperture 2006 through which light is delivered to the first and second light detectors 222/224, respectively are designed to be equidistant from the light delivery aperture 1002 (see FIG. 10), any differences between $DR_{em,filtered}$ and $DR_{em}$ are assumed to be a result of heterogeneity on the optical properties of the skin traversed by the two different optical paths.

Excitation-Wavelength Light Leak-Through Correction

In one aspect, $DR_{ex_{meas}}$ serves as a basis for the estimation of leak-through of excitatory-wavelength light into the second (filtered reference) light detector 224 used as part of the method of removing the effects of variation in background signal described herein. Without being limited to any particular theory, it is assumed that the amount of leak-through of excitatory-wavelength light into the second (filtered reference) light detector 224 is proportional to the $DR_{ex}$ signal, and that this proportion is influenced exclusively by device-related factors, rather than factors related to the optical properties of the patient's skin. As a result, the proportion of the $DR_{ex}$ signal representing leak-through light is assumed to be constant, as described herein below.

In one aspect, the excitation-wavelength light leak-through (ExLT) included within the raw fluorescence signal (Flr) is assumed to be a constant fraction $C_{ExLT}$ of the $DR_{ex_{meas}}$ signal according to Eqn. (21):

$$ExLT = C_{ExLT} * DR_{ex_{meas}} \qquad \text{Eqn. (21)}$$

where $C_{ExLT}$ is a sensor-head specific calibration factor.

In one aspect, $C_{ExLT}$ is obtained by computing the ratio between the excitation light detected by first and second light detectors 222/224 (Det1/Det2) on a non-fluorescing optical phantom according to Eqn. (22):

$$C_{ExLT} = \frac{Det2}{Det1} = \frac{Flr_{meas}}{DR_{ex_{meas}}} \qquad \text{Eqn. (22)}$$

In another aspect, the excitation light reaching the filtered detector is assumed to be different than the light reaching the non-filtered detector due to tissue heterogeneity. In this aspect, the ratio of the emission-wavelength light at each detector is used to correct for this heterogeneity.

In various aspects, the calibration factor $C_{ExLT}$ may be specific to an individual sensor head 204 or $C_{ExLT}$ may be applicable to all sensor heads 204 of a system 200 depending on various factors including, but not limited to, manufacturing tolerances. In an aspect, if the system 200 is used to obtain $C_{ExLT}$, $Flr_{meas}$ and $DR_{ex_{meas}}$ are from a non-fluorescent, homogeneous phantom in the context of the system 200 as described herein above. It is to be noted that Eqn. (22) assumes that the tissue monitored by the system 200 is homogeneous.

In an aspect, the excitation-wavelength light leak-through (ExLT) determined by Eqn. (21) may be subtracted from the raw fluorescence signal ($Flr_{meas}$) to obtain a corrected fluorescence signal $F_{photons}$ as described in Eqn. (23):

$$Flr_{photons} = Flr_{meas} - ExLT \qquad \text{Eqn. (23)}$$

Figure 17A:
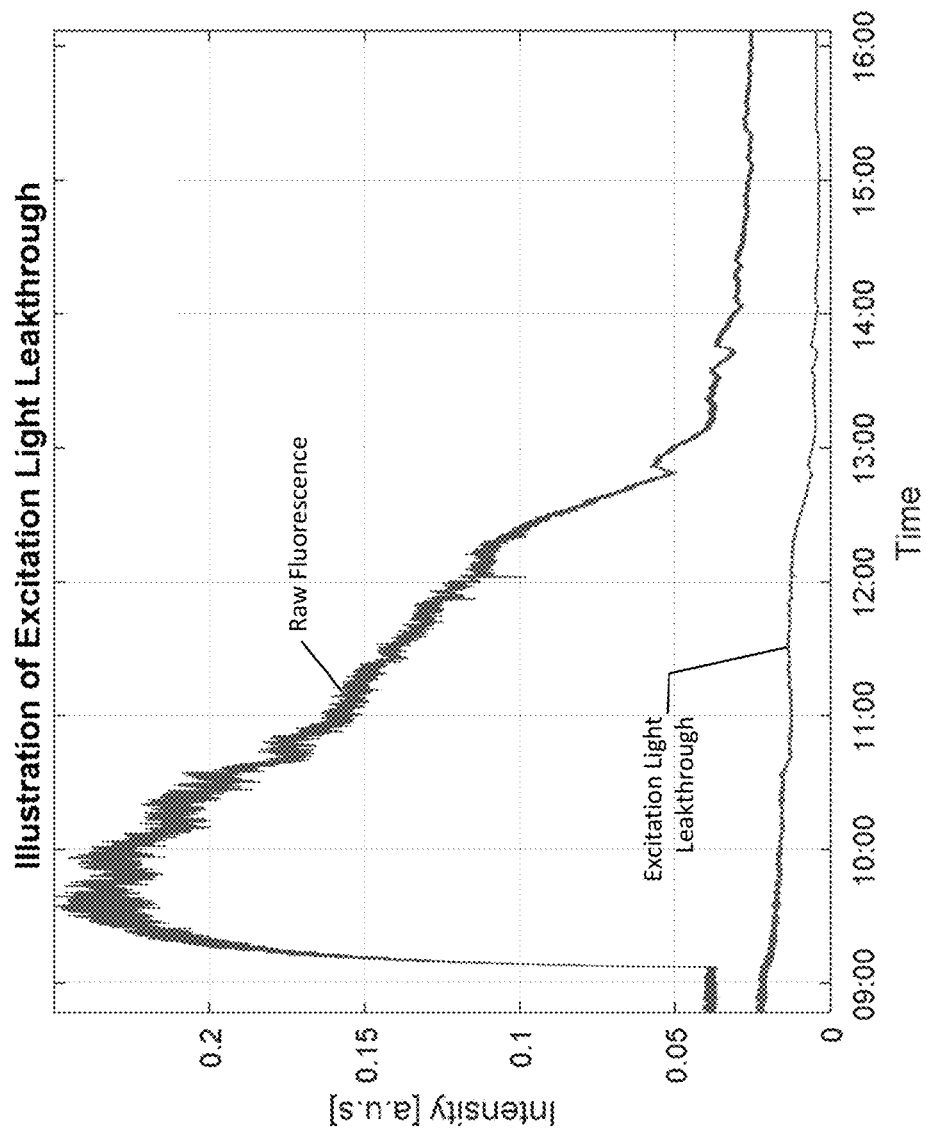
FIG. 17A is a graph of raw fluorescence signal and excitation light leak-through as a function of time.
Figure 17B:
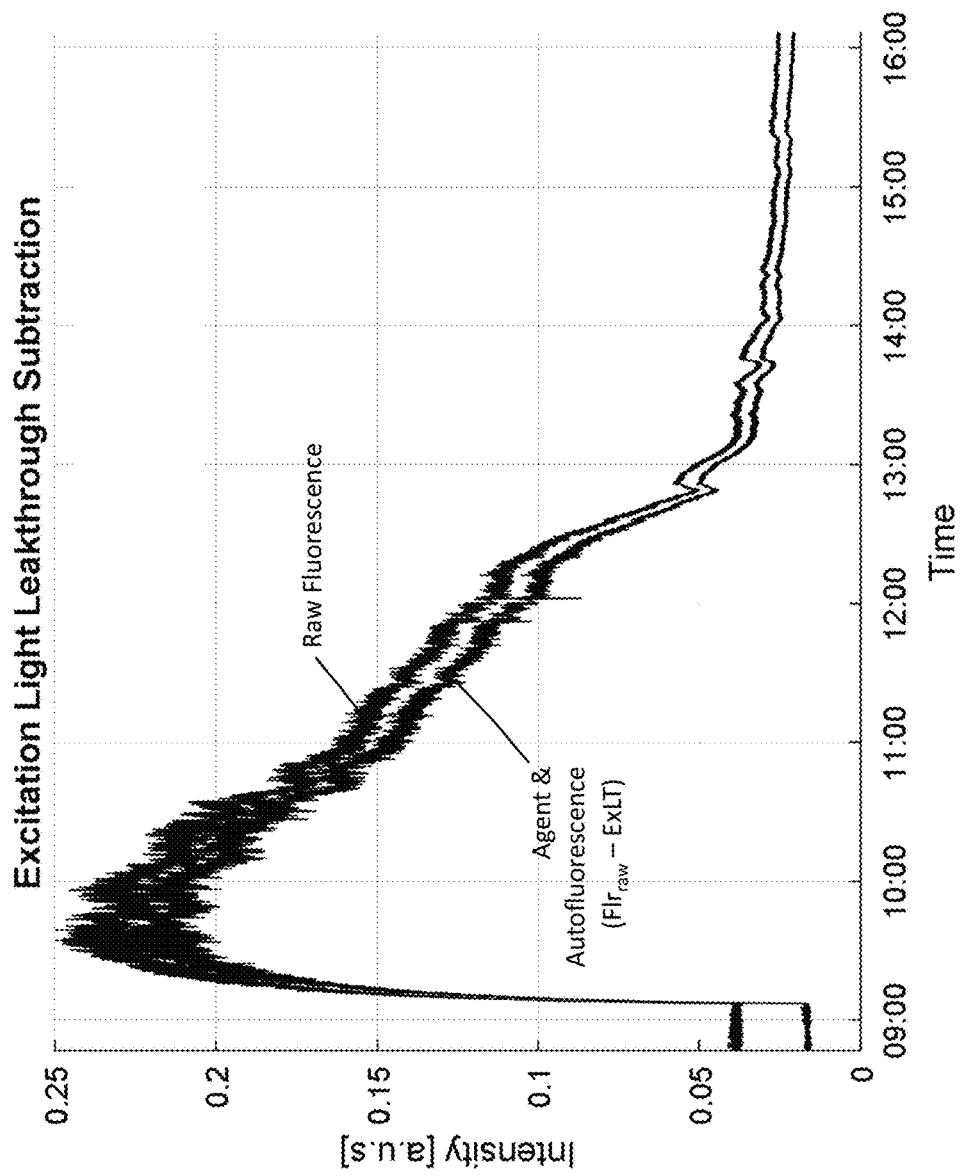
FIG. 17B is a graph of raw fluorescence signal of FIG. 17A and a corrected fluorescence signal comprising the raw fluorescence signal with the excitation light leak-through of FIG. 17A removed.

FIG. 17A is a graph of a raw fluorescence signal ($Flr_{meas}$, blue line) and the corresponding excitation-wavelength light leak-through (ExLT, red line) determined using Eqn. (23) obtained by a system 200 in one aspect before and after the injection of an exogenous fluorescence agent. As illustrated in FIG. 17A, the ExLT signal varies over the course of data acquisition. FIG. 17B is a graph comparing the raw fluorescence signal ($Flr_{meas}$, blue line) and the fluorescence signal with the excitation-wavelength light leak-through removed ($Flr_{photonsT}$, green line) as described herein above in Eqn. (23).

In one aspect, the raw fluorescence signals $Flr_{meas}$ are first corrected to remove the effects of excitation-wavelength light leak-through using Eqn. (23). In this aspect, subsequent corrections to remove the effects of autofluorescence are implemented using the corrected fluorescence signal $Flr_{photons}$ as a basis as described herein below.

Fluorescence Leak-Through Correction

Without being limited to any particular theory, the light detected by the unfiltered light detector during illumination by light at the excitatory wavelength is a mixture of diffuse reflectance of the excitation wavelength light and light from agent fluorescence. In one aspect, the diffuse reflectance is assumed to be sufficiently more intense than the fluorescence such that the contribution of fluorescence to the unfiltered detector measurement was negligible.

Figure 27:
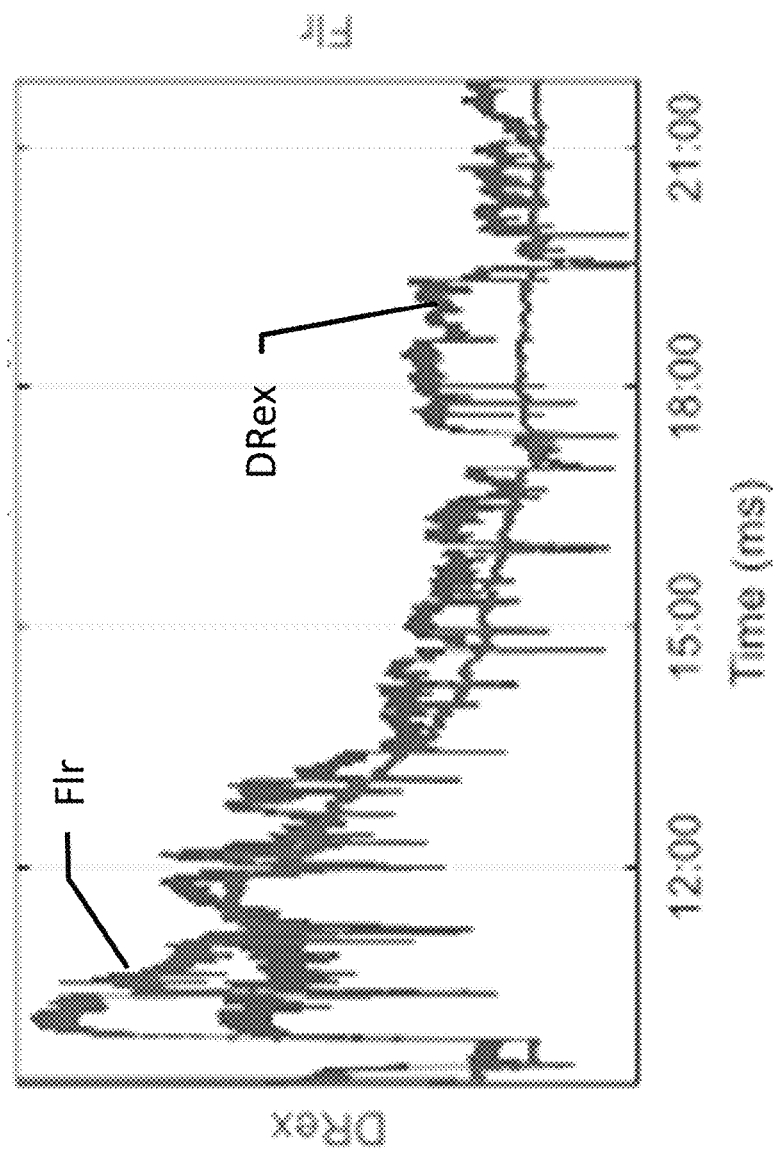
FIG. 27 is a graph showing $DR_{ex_{meas}}$ and $Flr_{meas}$ over a full day in the absence of administration of an exogenous fluorescent agent.
Figure 28:
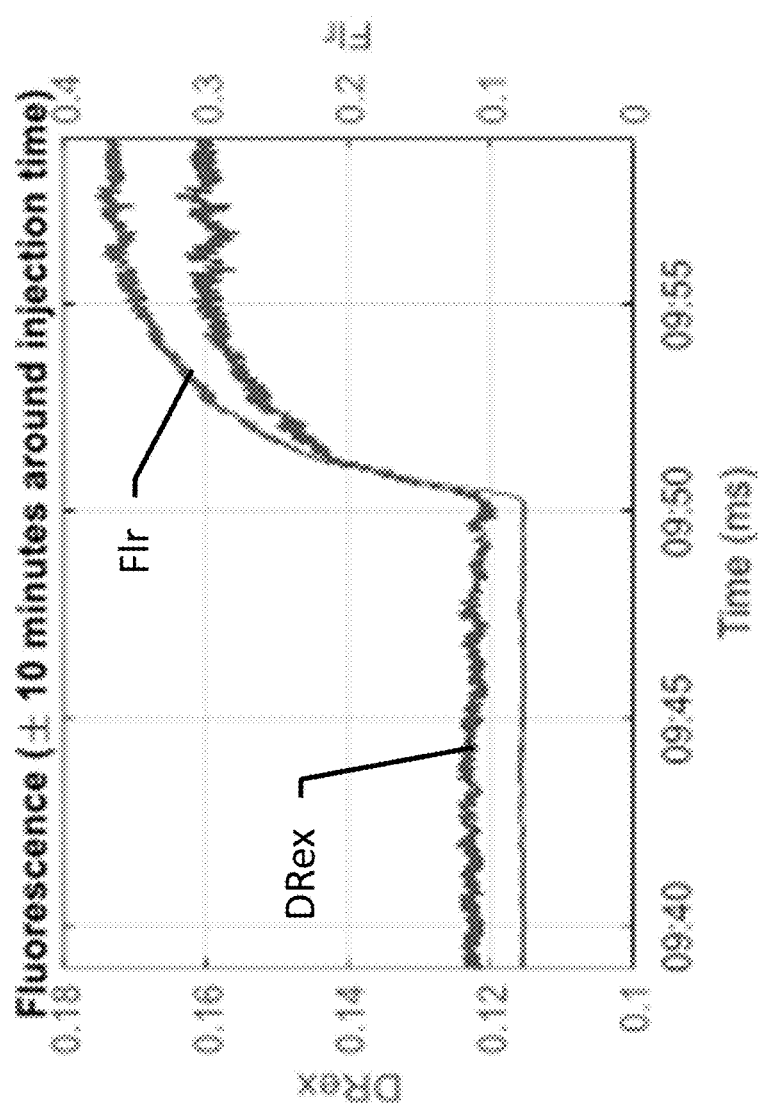
FIG. 28 is a graph showing $DR_{ex_{meas}}$ and $Flr_{meas}$ immediately preceding and following administration of an exogenous fluorescent agent.

In another aspect, the contribution of fluorescence to the unfiltered detector measurement may be non-negligible. By way of non-limiting example, FIG. 27 is a graph showing $DR_{ex_{meas}}$ and $Flr_{meas}$ over a full day in the absence of administration of an exogenous fluorescent agent. However, as illustrated in FIG. 28, the $DR_{ex_{meas}}$ signal occasionally showed leak through of fluorescence, as evidenced by a correlated signal rise after agent administration into the patient's bloodstream.

In one aspect, the portion of the diffuse reflectance excitation signals due only to excitation photons are removed from the raw $DR_{ex_{meas}}$ signal according to Eqn. (24):

$$DRex_{photons} = DRex_{meas} - Flr_{meas} * C_{FlrLT} \qquad \text{Eqn. (24)}$$

In various aspects, the coefficient $C_{FlrLT}$ is empirically determined using the relationship between a measured amount of fluorescence leak-through ($Flr_{leakthrough}$) on the $DRex_{meas}$ signal, in relation to tissue heterogeneity as expressed by the ratio $$\frac{DRemFilt}{DRem}$$

Figure 29:
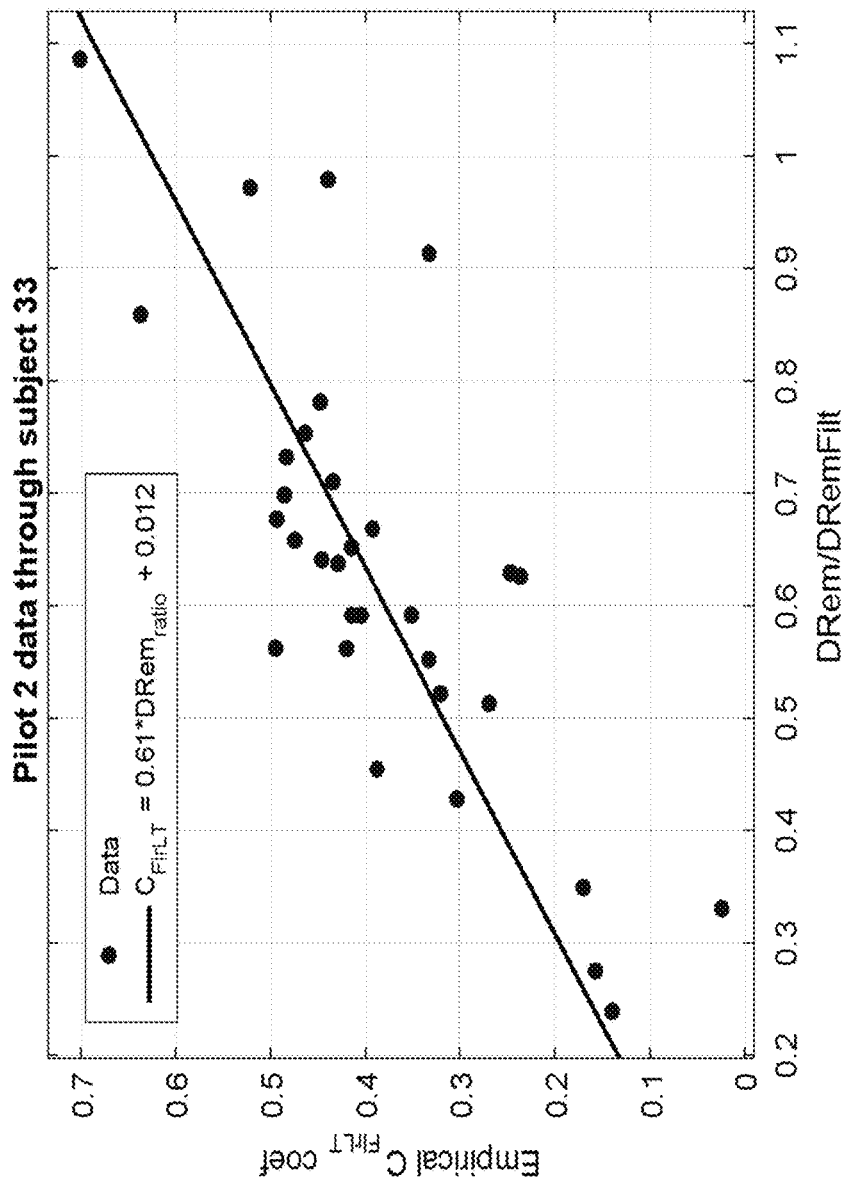
FIG. 29 is a graph summarizing a relationship between empirically determined $Flr_{leakthrough}$ and $$\frac{DRem}{DRemFilt}$$

(see discussion below). In one aspect, the measurements may be obtained from a plurality of subjects. By way of non-limiting example, FIG. 29 is a graph summarizing a relationship between empirically determined $Flr_{leakthrough}$ and $$\frac{DRem}{DRemFilt}$$

derived from a database of 33 patients. In this aspect, this empirically-derived relationship was checked on multiple patient datasets and found to be consistent. The correction coefficient $C_{FlrLT}$ was set to incorporate the relationship between tissue heterogeneity and amount of fluorescence leak through, as defined below:

$$C_{FlrLT} = p1 * \left(\frac{DRem}{DRemFilt}\right) + p2 \qquad \text{Eqn. (25)}$$

In one aspect, Eqn. (25) includes p1=0.6138 and p2=0.01095, as determined by a bisquares weighted linear fit to the relationship illustrated in FIG. 29.

In another aspect, $C_{FlrLT}$ is determined by obtaining measurements on optical phantoms provided with increasing fluorescence concentrations, where the only change signals is due to concentration of exogenous fluorescence agent concentration.

Isolation of Fluorescence and Excitation Wavelength Diffuse Reflectance

In various aspects, the number of photons due to either $DR_{ex}$ or $Flr$ on either the filtered or unfiltered detector depends on light directionality and the gain of each detector at the detected wavelength, as shown below:

$$DRex_{meas} = A_1 * DRex_{photons} + B_1 * Flr_{photons} \qquad \text{Eqn. (26)}$$

$$Flr_{meas} = A_2 * DRex_{photons} + B_2 * Flr_{photons} \qquad \text{Eqn. (27)}$$

where the coefficients $A_1$, $A_2$, $B_1$, and $B2$ include a directionality and gain factor. By way of non-limiting example, $A_1$ may be provided in the form of Eqn. (28):

$$A_1 = d450_{SPM1} * G_{SPM1@450} \qquad \text{Eqn. (28)}$$

where $d450_{SPM1}$ and $G_{SPM1@450}$ are directionality and gain factors of a detector SPM1 at an illumination wavelength of 450 nm.

In one aspect, the photon signals may be isolated as expressed in Eqns. (29) and (30):

$$B_1\left(\frac{B_2}{B_1} - \frac{A_2}{A_1}\right) Flr_{photons} = Flr_{meas} - \frac{A_2}{A_1} DR_{ex_{meas}} \qquad \text{Eqn. (29)}$$

$$A_2\left(\frac{A_1}{A_2} - \frac{B_1}{B_2}\right) DRex_{photons} = DR_{ex_{meas}} - \frac{B_1}{B_2} Flr_{meas} \qquad \text{Eqn. (30)}$$

In various aspects, the constant terms in front of the photon signals, such as $$B_1\left(\frac{B_2}{B_1} - \frac{A_2}{A_1}\right)$$

are not needed, because the renal function monitors as disclosed herein measure rates of change of intrinsic fluorescence (IF) as expressed by Eqn. (31):

$$IF = C_0 + C_1 e^{-t/\tau} \rightarrow \log(IF) = \log(C_1) - \frac{1}{t} \qquad \text{Eqn. (31)}$$

In one aspect, the terms $$\frac{A_2}{A_1} (\text{or } C_{ExLT}) \text{ and } \frac{B_1}{B_2} (\text{or } C_{FlrLT})$$

are determined experimentally to isolate $Flr_{photons}$ and $DRex_{photons}$, respectively, as described above.

Autofluorescence Correction

In various aspects, the method of correcting the measured fluorescence to remove the time-varying effects of background may further include removing the effects of autofluorescence in addition to removing the effects of excitation-wavelength leak-though. Autofluorescence, as used herein, refers to the emission-wavelength light produced by endogenous chromophores, such as keratin and collagen, in response to illumination by excitation-wavelength light. In various aspects, autofluorescence may vary over the course of acquiring fluorescence measurements using the systems and methods described herein. Without being limited to any particular theory, changes in the optical properties of the patient's skin, such as changes in the concentration of chromophores such as hemoglobin and/or melanin may cause variation in autofluorescence levels.

Figure 18:
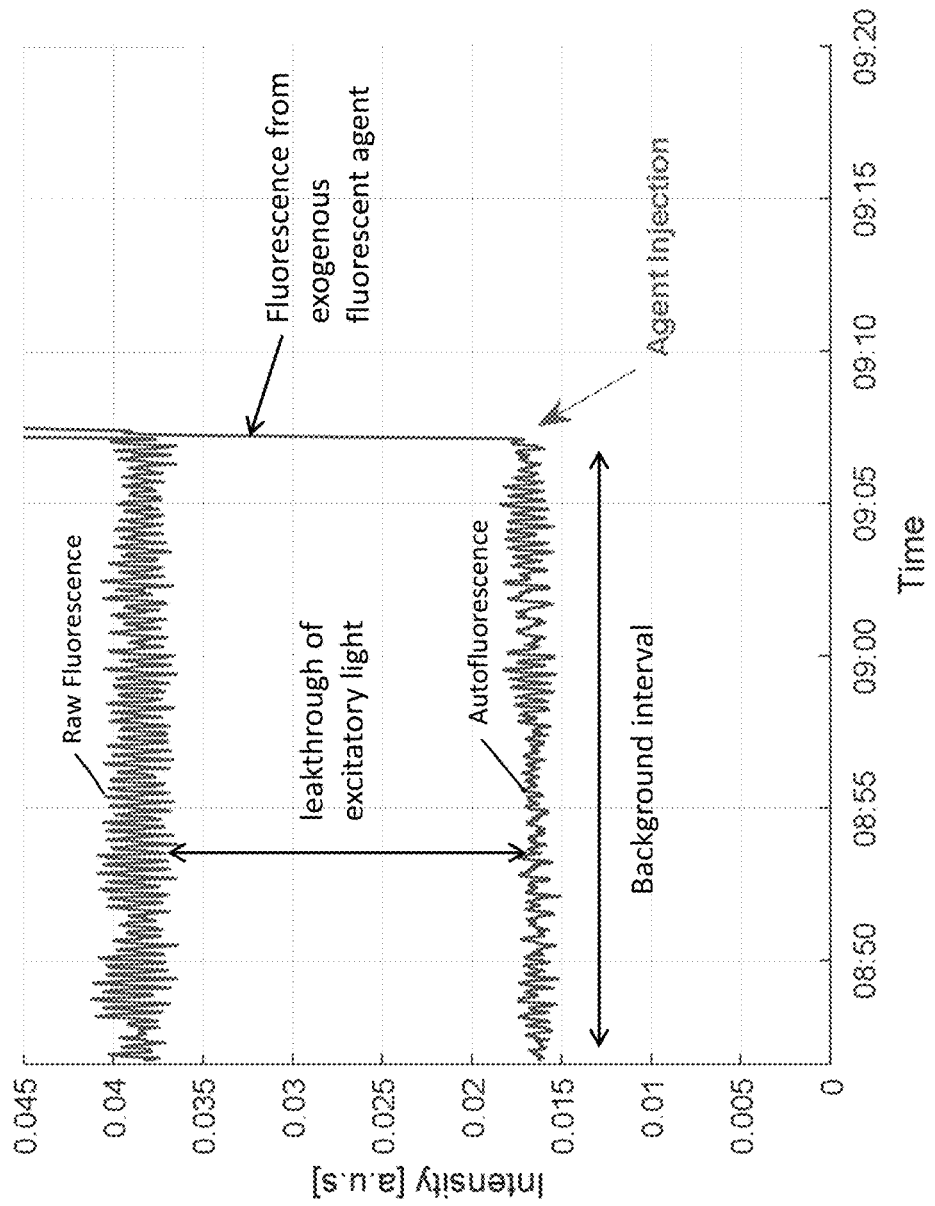
FIG. 18 is a graph comparing raw fluorescence signal (blue line) and autofluorescence signal (green line) obtained prior to injection of an exogenous fluorescent agent.

FIG. 18 is a graph summarizing the measurements of raw fluorescence ($Flr_{meas}$, blue line) obtained during the background interval, defined herein as the interval prior to injection of the exogenous fluorescent agent into the patient 202, when the patient's tissues are assumed to contain no exogenous fluorescent agents. Also shown in FIG. 18 is the signal resulting from the removal of the effects of leak-through of excitatory-wavelength light (ExLT) from $Flr_{meas}$ using Eqn. (5) as described herein above. The remaining fluorescence signal detected during the background interval, shown as a green line in FIG. 18, may be assumed to be attributable to autofluorescence in various aspects.

In one aspect, the intrinsic autofluorescence ($IF_{auto}$), defined here as the measured fluorescence at the emission wavelength attributable only to emission by endogenous chromophores, such as keratin and collagen, may be calculated as the median value of the corrected fluorescence signal $Flr_{photons}$ (see Eqn. 23) obtained during the background interval according to Eqn. (32).

$$IF_{Auto} = \text{median}(Flr_{photons}(1:endBackground)) \quad \text{Eqn. (32)}$$

where endBackground is the index of the data acquisition in the dataset corresponding to the end of the background interval just prior to injection of the exogenous fluorescent agent.

In an aspect, the autofluorescence may be assumed to be relatively stable throughout the entire data acquisition process, including the interval following injection of an exogenous fluorescent agent. In this aspect, the effect of autofluorescence may be removed by subtracting the $IF_{Auto}$ value obtained in Eqn. (32) from the corrected fluorescence signal $Flr_{photons}$ as expressed in Eqn. (33):

$$IF_{agent} = Flr_{photons} - IF_{Auto} \quad \text{Eqn. (33)}$$

where $IF_{agent}$ denotes the intrinsic fluorescence specifically representing the emission-wavelength light emitted by the exogenous fluorescent agent.

Figure 19A:
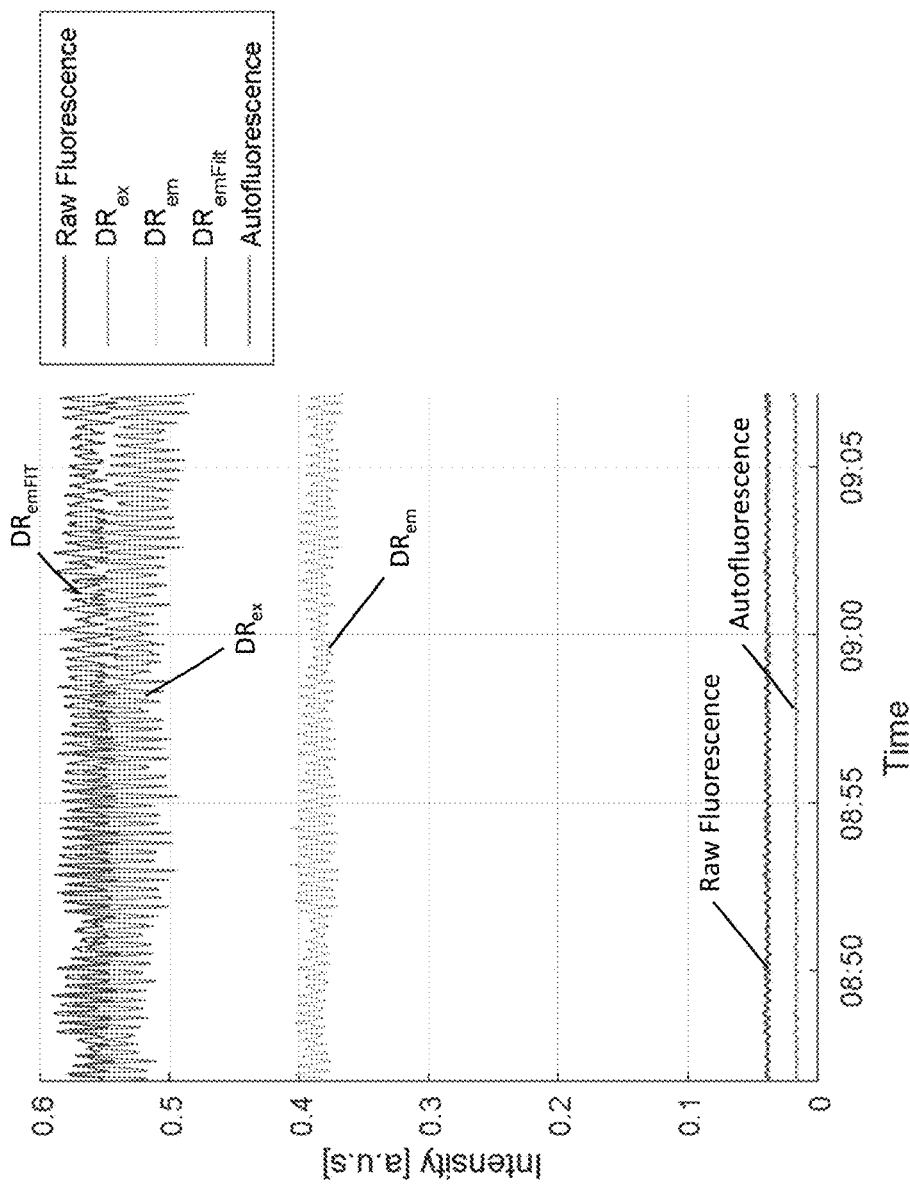
FIG. 19A is a graph comparing raw fluorescence signal, autofluorescence signal, and diffuse reflectance signals $DR_{ex_{meas}}$, $DR_{em}$, and $DR_{em,filtered}$ obtained prior to injection of an exogenous fluorescent agent.

FIG. 19A is a graph summarizing various measurements obtained during the background interval: raw fluorescence ($Flr_{meas}$), $DR_{ex_{meas}}$ (red line), $DR_{em}$ (orange line), and $DR_{em,filtered}$ (purple line). In addition, the intrinsic autofluorescence ($IF_{auto}$, green line) calculated using Eqn. (32) is also shown in FIG. 19A. During the background interval shown in FIG. 19A, all quantities were relatively stable in value.

Figure 19B:
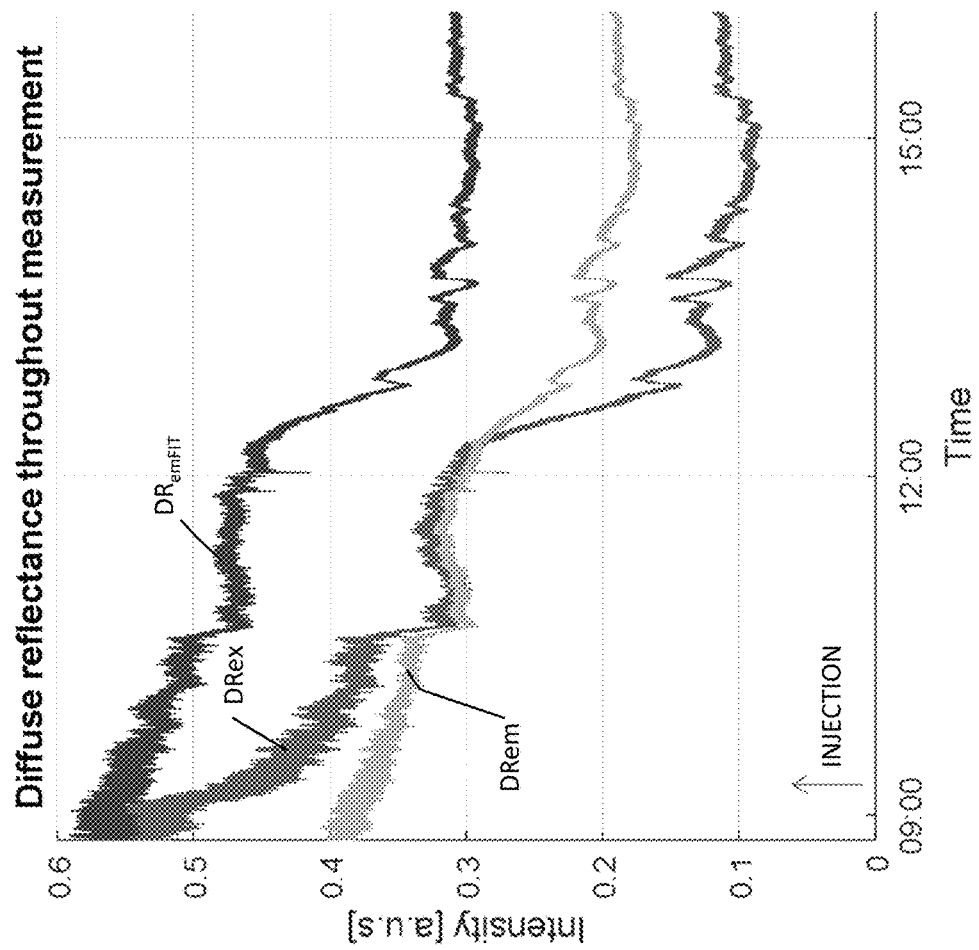
FIG. 19B is a graph comparing raw fluorescence signal, autofluorescence signal, and diffuse reflectance signals $DR_{ex_{meas}}$, $DR_{em}$, and $DR_{em,filtered}$ obtained after injection of an exogenous fluorescent agent.

FIG. 19B is a graph summarizing the diffuse reflection measurements shown in FIG. 19A: $DR_{ex_{meas}}$ (red line), $DR_{em}$ (orange line), and $DR_{em,filtered}$ (purple line). Over the course of obtaining fluorescence measurements after injection of the exogenous fluorescent agent (i.e. after a time of about 9:07 as shown in FIG. 18), the diffuse reflection measurements decrease significantly, indicating that the optical properties of the patient's skin, which impact the measured signal from autofluorescence, may also change during this time period.

In an additional aspect, diffuse reflectance measurements may be used to project the underlying autofluorescence signal for the full measurement period, thereby accounting for changes in the optical properties of the patient's skin over the full course of data measurements. In one aspect, diffuse reflection measurements may be used to scale the corrected fluorescence signal $Flr_{photons}$ to account for changes in the optical properties of the patient's skin, resulting in an intrinsic fluorescence. In this aspect, to correct the fluorescence measurements obtained after the injection of the exogenous fluorescence agent, the intrinsic autofluorescence ($IF_{auto}$) calculated from Eqn. (32) may be subtracted from the combined intrinsic fluorescence $IF_{AgentAndAuto}$ obtained from Eqn. (33), as expressed in Eqn. (34):

$$IF_{agent} = IF_{AgentAndAuto} - IF_{Auto} \quad \text{Eqn. (34)}$$

Figure 20:
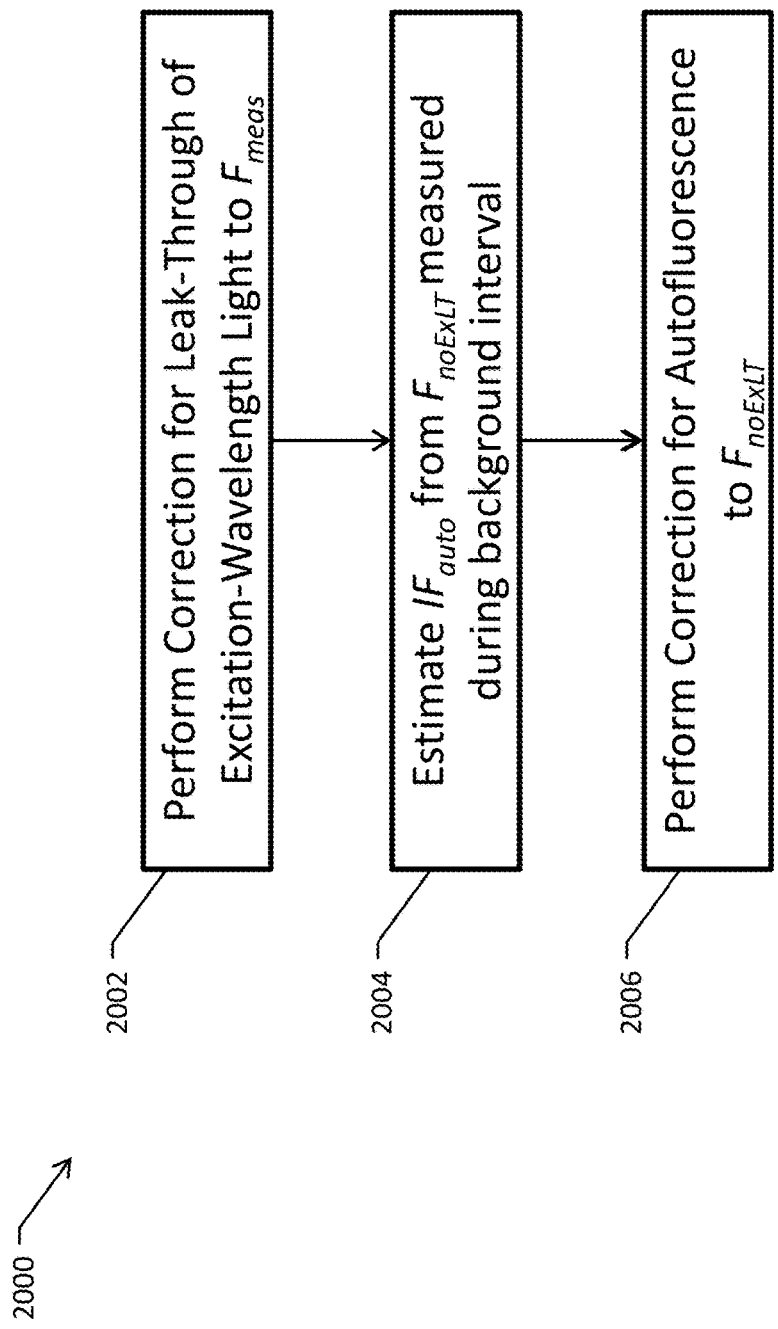
FIG. 20 is a flow chart summarizing the steps of a background correction method for removing the effects of excitation-wavelength light leak-through and autofluorescence from the raw measured fluorescence signal.

In one aspect, the background correction subunit 1306 may enable a background correction method 2000 as summarized in the block diagram of FIG. 20. The method 2000 may include performing a correction at 2002 to remove the effects of the leak-through of emission-wavelength light into the second (filtered reference) light detector 224 as described in Eqns. (29), (30), and (31) above. The method 2000 may further include estimating the level of autofluorescence ($IF_{auto}$) at 2004 from an analysis of the measurements obtained during the background interval as described in Eqn. (32) above. The method 2000 may additionally include performing a correction at 2006 to remove the effects of autofluorescence from the fluorescence measurements as described in Eqn. (33) above. In effect, the autofluorescence signal $IF_{auto}$ is projected forward into subsequent fluorescence measurements and is removed at 2006. The intrinsic fluorescence $IF_{agent}$ resulting from the removal of background effects from the raw fluorescence measurements may transformed by the RDTC calculation subunit 1310 as described herein below into a parameter including, but not limited to, glomerular filtration rate (GFR) and/or renal decay time constant (RDTC) representing renal function.

e) Fault Detection Subunit

Referring again to FIG. 13, the processing unit 236 of the controller 212 may further include a fault detection subunit 1312 configured to monitor the function of the light sources 218/220 and light detectors 222/224 and to inform the user of any irregularities of any detected faults within the system 200 via the display unit 216. In various aspects, the fault detection subunit 1312 may enable the basic identification of fault and notice states by examining the signal levels received from the light sources 218/220 and light detectors 222/224 and associated additional temperature sensors 228 and additional light detectors 226 of the sensor head 204 (see FIG. 2). In various aspects, the signal magnitudes (see Eqn. (1)) and average signals may be used to determine the peak and nadir levels of the modulation of the LED light sources 218/220. The nadir of the signal, defined herein as the average signal minus half the peak-to-peak signal, may be used to monitor ambient light levels in one aspect. Without being limited to any particular theory, additional contributions to the nadir levels of the modulated signals, such as amplifier DC offset, may be neglected as small and constant relative to the contributions of ambient light leakage. In an aspect, if the detected ambient light levels register in excess of about one quarter of the high-speed ADC 1102 range at low detector amplifier gain, an ambient light notice is issued to the user via the display unit 216.

In various other aspects, saturation of the light detectors 222/224 detectors may also be monitored by the fault detection subunit 1312. In these other aspects, the saturation may be monitored by calculating the peak value of the signal, defined herein as the average signal value plus half the peak-to-peak signal. If the signal's peak value falls within is within 5% of saturation of the ADC range, the fault detection subunit 1312 may issue a saturation notice to the user via the display unit 216. If saturation event is detected by the fault detection subunit 1312, the ambient light level may then be checked to determine if the saturation event is associated with ambient light saturation, defined herein as a saturation event occurring concurrently with an ambient light notice as described herein above. If an ambient light saturation event is detected, the fault detection subunit 1312 issues an ambient light saturation notice to the user via the display unit 216, and data acquisition by the acquisition unit 234 is continued in this notice state to allow the user to resolve the condition. If a saturation event is detected that is not associated with an excess of ambient light, the fault detection subunit 1312 may signal the light detector control unit 232 to perform an adjustment of detector gain and/or may signal the light source control unit 230 to perform an adjustment to the LED current source 1126 to adjust LED intensity. In various aspects, the fault detection subunit 1312 issues a notification to the user via the display unit to report either the ambient light saturation event, or the saturation event not associated with an excess of ambient light. In some aspects, if a saturation event is detected, but the automatic gain adjustment has been disabled by a user when the system 200 is configured in the Engineering Mode as described herein above, the user is also notified via the display unit.

e) Post-Agent Administration Selection Subunit

Referring again to FIG. 13, the processing unit 236 may further include a post-agent administration subunit 1308 configured to automatically identify the portion of the measurement data set that corresponds to an post-agent administration region, as described herein below.

Figure 21:
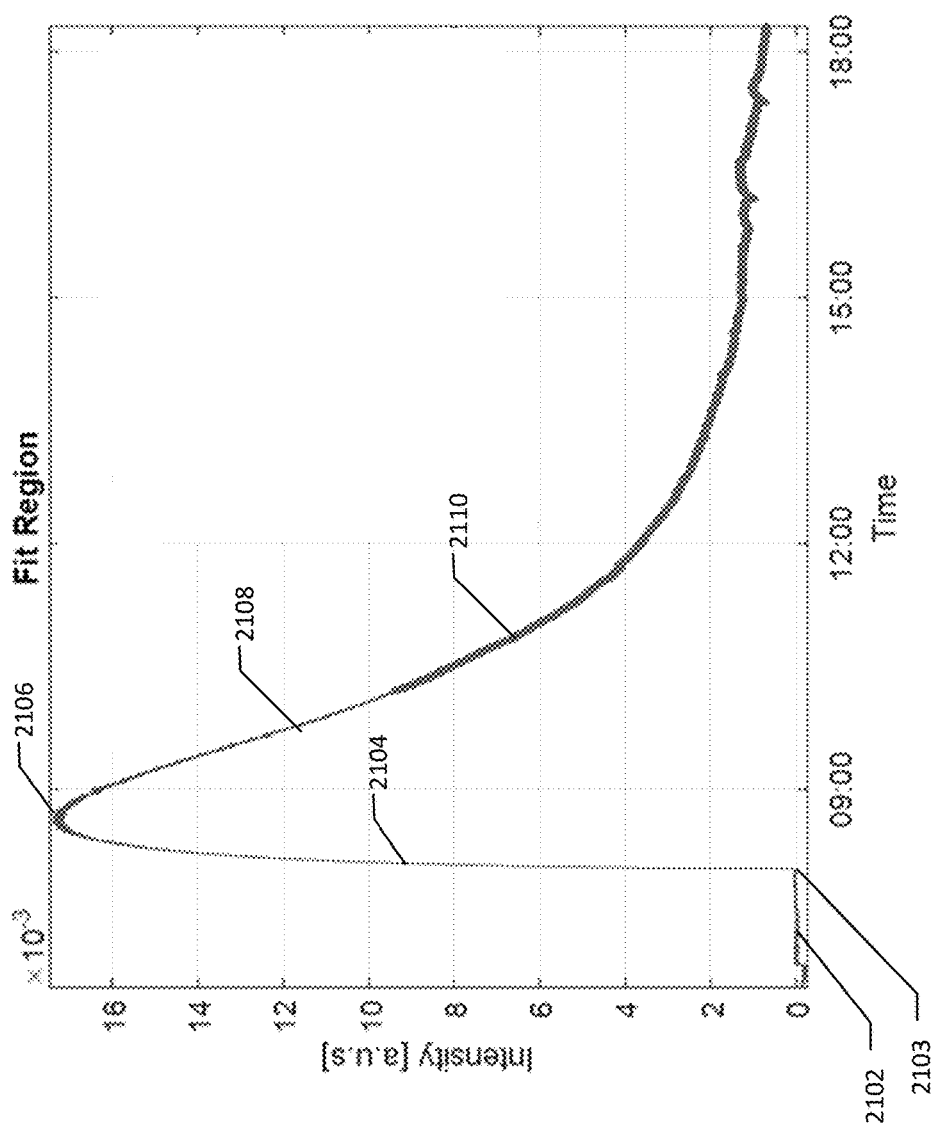
FIG. 21 is a graph of representative raw fluorescence signal measurements ($IF_{agent}$) detected by a renal monitoring device obtained before and after injection of an exogenous fluorescent agent.

FIG. 21 is a graph of fluorescence measurements obtained from a patient over a period of about 10 hours after injection of an exogenous fluorescence agent such as MB-102 after a pre-injection period 2102 of about 3 hours. Referring to FIG. 21, the pre-injection/baseline period 2102 is characterized by a relatively low and stable fluorescence level, likely due the absence of exogenous fluorescent agent in the blood of the patient. After the injection 2103 of the exogenous fluorescence agent, the fluorescence measurements exhibit a sharp increase 2106 to a peak concentration 2108, followed by a relatively smooth exponential decrease back to background fluorescence levels at the kidneys eliminate the exogenous fluorescence agent from the blood of the patient. Without being limited to any particular theory, it is thought the injected exogenous fluorescent agent is likely well-mixed after an amount of time in the exponential concentration decrease has elapsed.

Referring again to FIG. 21, after an exogenous fluorescent agent, such as MB-102, is injected into the bloodstream of a patient, the exogenous fluorescent agent undergoes an equilibration period of diffusion from the bloodstream into the rest of the extracellular tissues of the patient. After agent injection 2103, the temporal profile of the fluorescence signal IF may be characterized as a two-exponential signal profile described by Eqn. (35):

$$IF_{pre\text{-}equilibration} = C_0 + C_1 e^{-t/\tau_1} + C_2 e^{-t/\tau_2} \qquad \text{Eqn. (35)}$$

in which $C_0$ is the baseline signal that is typically removed by baseline subtraction as described herein above.

Referring again to FIG. 21, once the diffusion of the exogenous fluorescent agent into the extracellular tissues of the patient reaches a quasi-steady state condition, post-equilibration 2110 is achieved and the fluorescence signal may be characterized as a linear decay. Without being limited to any particular theory, the post-equilibration region 2110 of the measurement data set is assumed to be characterized as a temporal region of the IF dataset that, when log-transformed, is well-described by a linear equation. In one aspect, the post-equilibration region is well-described described by Eqn. (36):

$$IF_{post\text{-}equilibration} = C_0 + C_1 e^{-t/\tau} \qquad \text{Eqn. (36)}$$

In an aspect, the post-agent administration selection subunit 1308 may identify the post-equilibration period 2110 automatically by performing a single-exponent curve fit at different portions of the IF data set and analyzing the associated curve fitting errors for each of the different portions. In various aspects, the post-agent administration selection subunit 1308 may select the earliest-occurring portion of the IF data set in which the curve-fit error associated with a single-exponent curve fit falls below a threshold value as the initial post-equilibration portion of the IF data set suitable for data correction and analysis as described herein above. Any analysis method suitable for comparing curve-fit errors association with single-exponential curve fits of different portions of the IF data set may be used in the post-agent administration selection subunit 1308 including, but not limited to, linear curve-fitting portions of the IF data set falling within overlapping or non-overlapping data windows and comparing the curve-fit errors of the corresponding data windows. In an aspect, the post-agent administration selection subunit 1308 may produce at least one signal configured to signal the time range within the IF data set corresponding to the post-equilibration period 2110 to the RDTC calculation subunit 1310 to enable the selection of a suitable portion of the IF data set to correct and analyze as disclosed herein.

In another aspect, a linear fit and a 2-exponential fit to the IF data may be compared. In this other aspect, equilibration may be identified as complete once the fitting error is equivalent (corrected for the extra degrees of freedom in the 2-exponential fit).

f) RDTC Calculation Subunit

In various aspects, the system 200 is configured to transform the various measurements from the light detectors 222/224 and associated light sources 218/220 and other thermal and light sensors into a corrected intrinsic fluorescent (IF) signal corresponding to the detected fluorescence attributable solely to emission of fluorescence by the exogenous fluorescent agent at the emission wavelength in response to illumination by light at the excitatory wavelength. In various aspects, the exponential decrease of the IF signals during the post-agent administration portion of the IF data set may be analyzed to monitor and quantify renal function.

In one aspect, the exponential decrease of the IF signals during the post-agent administration portion of the IF data set may be transformed into a glomerular filtration rate (GFR) configured to quantify renal function. In another aspect, the exponential decrease of the IF signals during the post-equilibration portion of the IF data set may be transformed into a renal decay time constant (RDTC), also configured to quantify renal function. In another aspect, the exponential decrease of the IF signals during the post-equilibration portion of the IF data set may be transformed into a renal decay rate, also configured to quantify renal function.

Referring again to FIG. 13, the processing unit 236 may further include an RDTC calculation subunit 1310 configured to automatically transform the IF signals into a renal decay time constant (RDTC). As used herein, renal decay time constant (RDTC) is defined as the time constant associated with the post-equilibration single-exponential decay described in Eqn. (36) herein above. In one aspect, after accurate baseline subtraction by the baseline subtraction subunit 1304, the renal decay time constant z may be calculated by performing a linear regression on the log-transformed IF signal data (log (IF)), as described in Eqn. (37):

$$\log(IF) = \log(C_1) - \frac{1}{\tau}t \qquad \text{Eqn. (37)}$$

In various aspects the RDTC calculation subunit 1310 may produce signals configured to produce a display of the calculated RDTC using the display unit 216. The display of the calculated RDTC may be provided to the display unit 216 in any suitable format including, but not limited to: a graph of RDTC as a function of time, a single discrete RDTC value, a table of RDTC values as a function of time, a color-coded display or other graphical representation configured to specific whether the calculated RDTC may be classified as normal/healthy, abnormal, high, low, and any other suitable classification. In various other aspects, any of the graphical formats described above may be continuously or non-continuously updates as additional data is obtained and analyzed. In one aspect, the RDTC calculation subunit 1310 may calculate RDTC as described herein above within non-overlapping and/or overlapping windows within the IF data set.

In another aspect, the RDTC calculation subunit 1310 may convert RDTC into glomerular filtration rate (GFR) using known methods. In this aspect, RDTC may be inverted and multiplied by a slope, resulting in cGFR, a prediction of GFR that may be corrected for body size (e.g. body surface area, or volume of distribution).

v) Memory

Referring again to FIG. 2, the controller 212 of the system 200 may further include a memory 242 configured to facilitate data storage in the system 200. In some embodiments, the memory 242 includes a plurality of storage components such as, but not limited to, a hard disk drive, flash memory, random access memory, and a magnetic or optical disk. Alternatively or additionally, the memory 242 may include remote storage such a server in communication with the controller 212. The memory 242 stores at least one computer program that, when received by the at least one processor, cause the at least one processor to perform any of the functions of the controller 212 described above. In one implementation, the memory 242 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more functions, such as those described herein. The information carrier may be a non-transitory computer- or machine-readable medium, such as the memory 242 or memory on the processor 238.

In various aspects, the system 200 may record raw measurements and processed data to a series of files. Each file may contain a header, which contains information about the operator, instrument, and session. Each experimental session records a set of files into a separate folder for each sensor head used in that session. The raw data file may contains in-phase, quadrature, and average measurements from the detectors and monitors during the active periods of both the excitation wavelength and the emission wavelength LEDs, along with the gain settings of the LEDs and detectors at the time of data acquisition.

In various other aspects, the processed data file may contain the fluorescence and diffuse reflectance measurements after magnitude calculation and correction for the monitor readings, along with the gain settings of the LEDs and detectors. The intrinsic fluorescence data file may contain the intrinsic fluorescence measurements resulting from the diffuse reflectance correction of the raw fluorescence signals. The GFR file may contain the calculated GFR as a function of time, classified to indicate whether post-equilibration has occurred, along with confidence bounds. The telemetry file may contain the temperature and voltage measurements. The event record file may contain both user and automatically generated event records.

vi) GUI Unit

Referring again to FIG. 2, the controller 212 may include a GUI unit 240 configured to receive a plurality of signals encoding various measured and transformed data from other units of the system in various aspects. In addition, the GUI unit may be configured to produce signals configured to operate the display unit 216 in order to display data, frames, forms, and/or any other communications of information between the user and the system 200.

vii) Processor

Referring again to FIG. 2, the controller 212 may further include a processor 238. The processor 238 may include any type of conventional processor, microprocessor, or processing logic that interprets and executes instructions. The processor 238 may be configured to process instructions for execution within the controller 212, including instructions stored in the memory 242 to display graphical information for a GUI on an external input/output device, such as display unit 216 coupled to a high speed interface. In other implementations, multiple processors and/or multiple buses may be used, as appropriate, along with multiple memories and types of memory. Also, multiple controllers 212 may be connected, with each device providing portions of the necessary operations to enable the functions of the system 200. In some embodiments, the processor 238 may include the acquisition unit 234, the light detector control unit 232, the light source control unit 230, and/or the processing unit 236.

As used herein, a processor such as the processor 238 may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As described herein, computing devices and computer systems include a processor and a memory. However, any processor in a computer device referred to herein may also refer to one or more processors wherein the processor may be in one computing device or a plurality of computing devices acting in parallel. Additionally, any memory in a computer device referred to herein may also refer to one or more memories wherein the memories may be in one computing device or a plurality of computing devices acting in parallel.

C. Operation Unit

The operation unit 214 may be configured to enable a user to interface (e.g., visual, audio, touch, button presses, stylus taps, etc.) with the controller 212 to control the operation of the system 200. In some embodiments, the operation unit 214 may be further coupled to each sensor head 204 to control the operation of each sensor head 204.

D. Display Unit

Referring again to FIG. 2, the system 200 may further include a display unit 216 configured to enable a user to view data and control information of the system 200. The display unit 216 may further be coupled to other components of the system 200 such as the sensor head 204. The display unit 216 may include a visual display such as a cathode ray tube (CRT) display, liquid crystal display (LCD), light emitting diode (LED) display, or "electronic ink" display. In some embodiments, the display unit 216 may be configured to present a graphical user interface (e.g., a web browser and/or a client application) to the user. A graphical user interface may include, for example, an display for GFR values as described herein above as produced by the system 200, and operational data of the system 200

Exogenous Markers

Without being limited to any particular theory, molecules which are highly hydrophilic and small (creatinine, molecular weight=113) to moderately sized (inulin, molecular weight ~5500) are known to be rapidly cleared from systemic circulation by glomerular filtration. In addition to these properties, an ideal GFR agent would not be reabsorbed nor secreted by the renal tubule, would exhibit negligible binding to plasma proteins, and would have very low toxicity. In order to design optical probes that satisfy all of these requirements a balance was struck between photophysical properties, and the molecular size and hydrophilicity of the fluorophore. For example, while hydrophobic cyanine and indocyanine dyes absorb and emit optimally within the near infrared (NIR) biological window (700-900 nm), hydrophilicity is not sufficiently high to function as pure GFR agents. Smaller dye molecules may be more easily converted to the extremely hydrophilic species required for renal clearance, but the limited 2-systems resulting from these lower molecular weight compounds generally enable one photon excitation and emission in the ultraviolet (UV).

To resolve the pharmacokinetic issues in concert with enhancing the photophysical properties, simple derivatives of 2,5-diaminopyrazine-3,6-dicarboxylic acid act as very low molecular weight fluorescent scaffold systems with bright emission in the yellow-to-red region of the electromagnetic spectrum. SAR studies have been carried out using amide-linked variants of these derivatives for the simultaneous optimization of GFR pharmacokinetics and photophysical properties. A variety of hydrophilic functionalities for enabling rapid renal clearance of this class of pyrazine fluorophores including carbohydrate, alcohol, amino acid and various PEG-based linker strategies may be employed. PEG substitution maybe used to increase hydrophilicity and solubility, reduce toxicity, and modulate aggregation of the resulting pyrazine derivatives. Variations of molecular weight and architecture (and hence hydrodynamic volume) in a series of moderately sized PEG-pyrazine derivatives may also be suitable for use as endogenous fluorescent agents.

In one aspect, the exogenous fluorescent agent is MB-102.

EXAMPLES

The following example illustrates various aspects of the disclosed systems and methods.

Example 1: Sensor Head with Flared Housing

Figure 23:
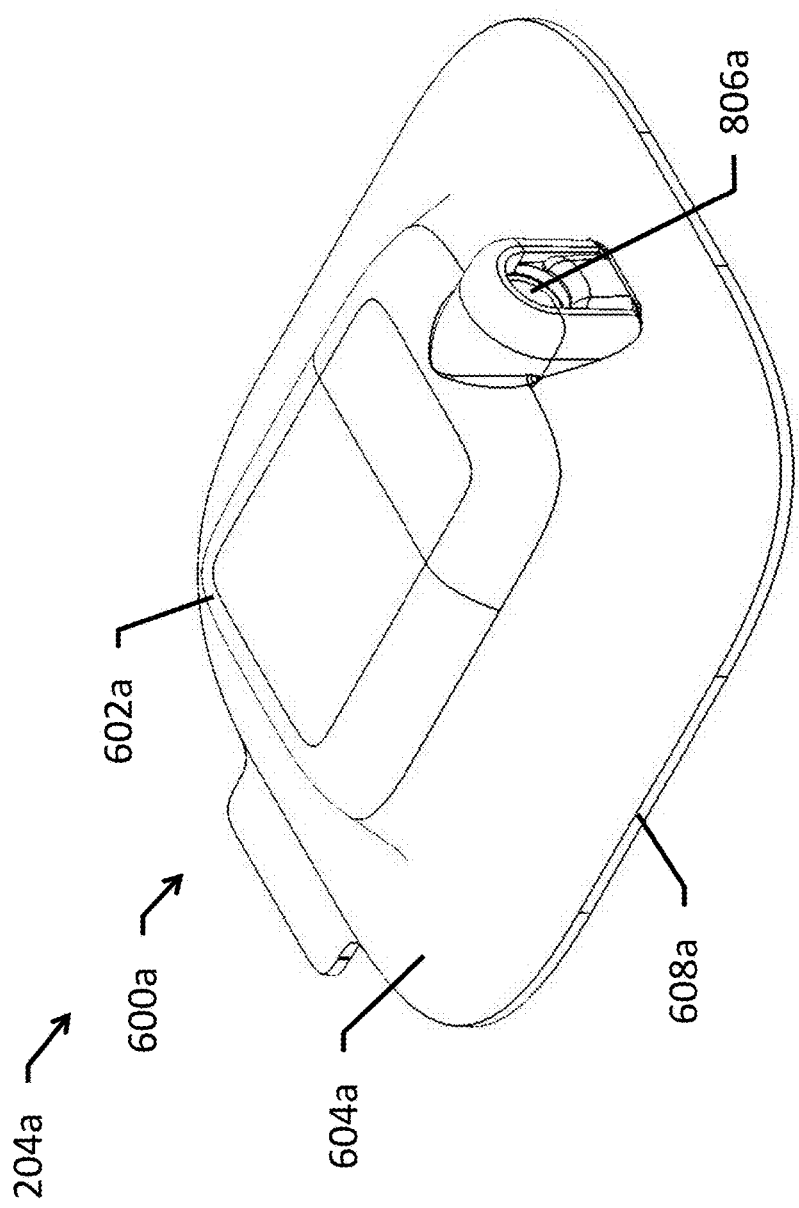
FIG. 23 is an isometric view of a sensor head of a renal function monitoring system in a second aspect.

FIG. 23 is a perspective view of a sensor head 204a in another aspect. In this other aspect, the sensor head 204a includes a housing 600a formed from an upper housing 602a and a flared lower housing 604a. The surface area of the lower housing 604a expands to form an enlarged bottom surface 608a. The housing 600a further includes a cable opening 806a formed through the upper housing 602a.

Figure 24:
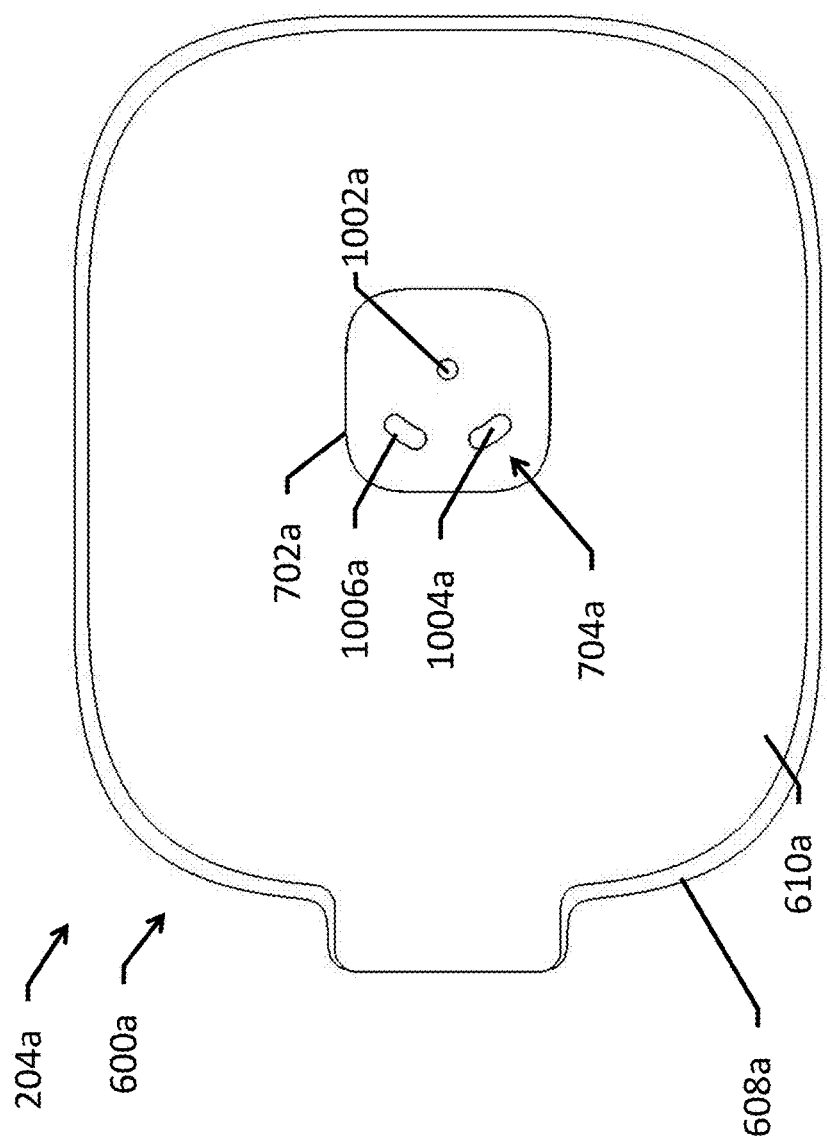
FIG. 24 is a bottom view of the sensor head of a renal function monitoring system illustrated in FIG. 23.

FIG. 24 is a bottom view of the sensor head 204a showing the bottom surface 608a of the housing 600a. The bottom surface 608a may include an aperture plate 702a including one or more apertures 704a configured to transmit light between the skin of the patient and the light sources and light detectors contained inside the housing 600. As illustrated in FIG. 24, the apertures 704a include a light delivery aperture 1002a configured to deliver illumination produced by the first and second light sources 218/220 to tissues of the patient 202, as well as first and second detector apertures 1004/1006 configured to receive light from the tissues of the patient 202. In one aspect, the bottom surface 608a enables the positioning of the apertures 704a beneath a relatively large area obscured from ambient light conditions by the bottom surface 608a. This reduction of scattered ambient light entering the first and second detector apertures 1004/1006 reduces noise introduced into the light intensity measurements obtained by the first and second light detectors 222/224.

In various aspects, the bottom surface 608a of the housing 600a may be attached the patient's skin using a biocompatible and transparent adhesive material 610a including, but not limited to, a clear double-sided medical grade adhesive, as illustrated in FIG. 24. The transparent adhesive material 610a may be positioned on the bottom surface 608a such that the adhesive material 610a covers the apertures 704a.

Figure 25:
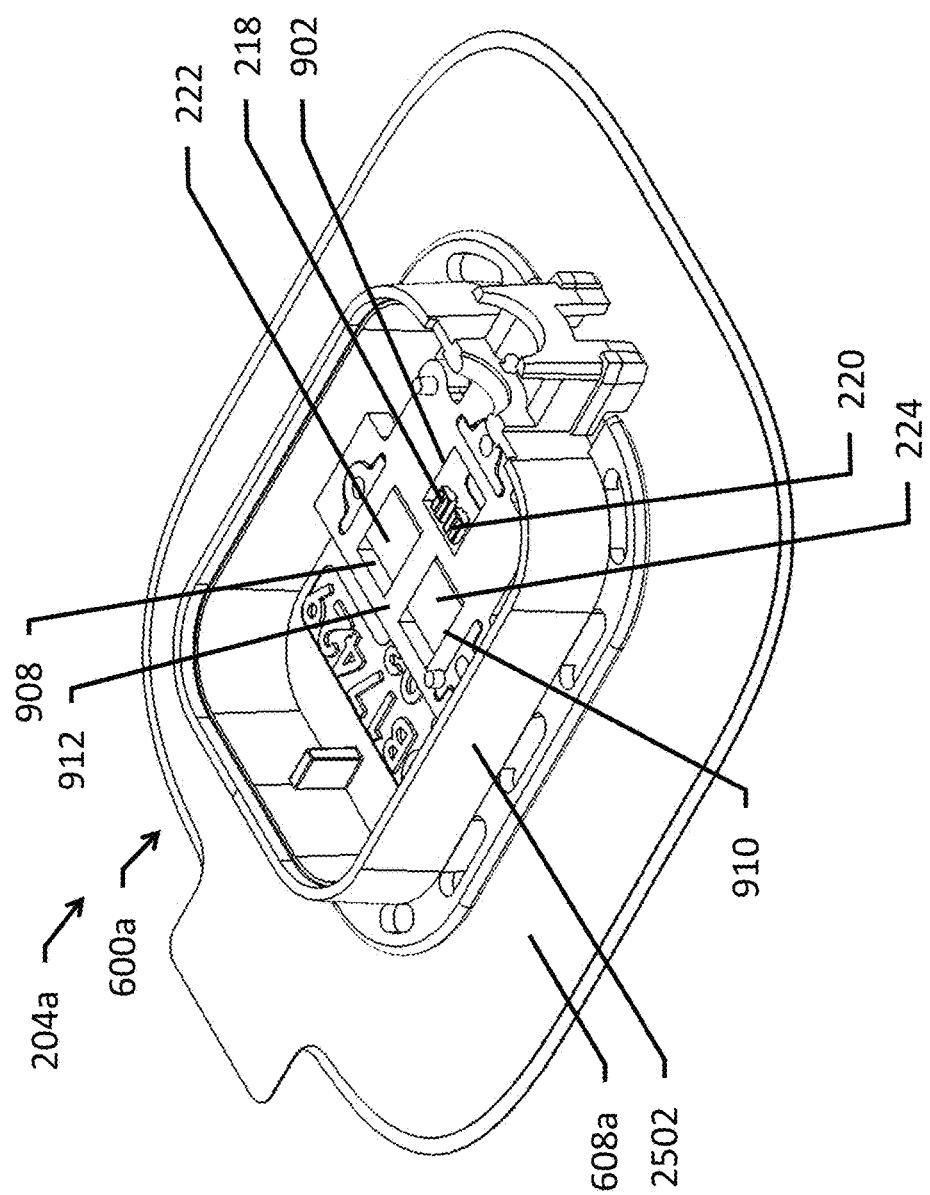
FIG. 25 is an isometric view of the sensor head of a renal function monitoring system illustrated in FIG. 23 with the upper housing and various electrical components removed to expose an inner housing.
Figure 26:
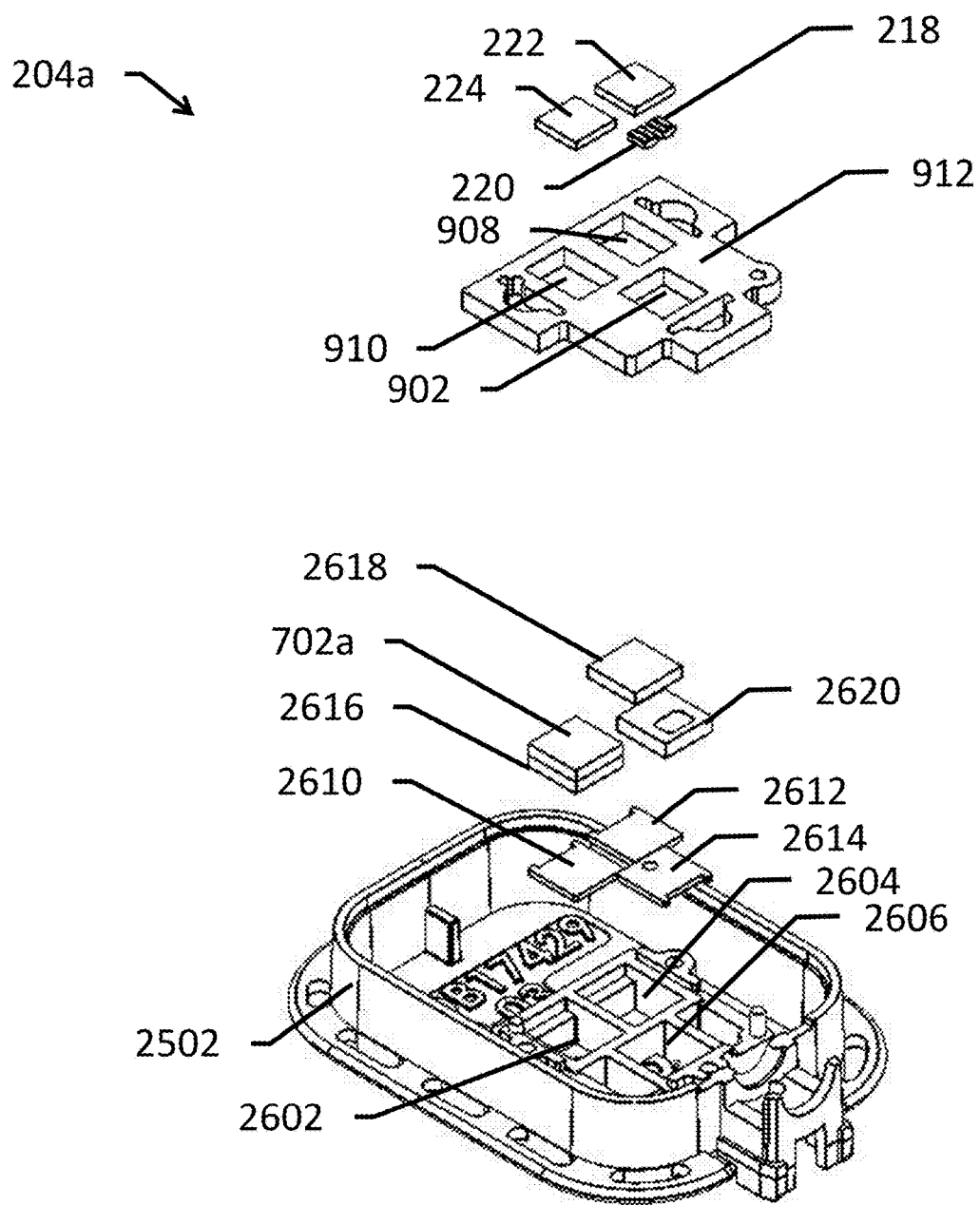
FIG. 26 is an exploded view of the inner housing of the sensor head illustrated in FIG. 25.

FIG. 25 is an isometric view of the sensor head 204a with the upper housing 602a and various electrical components removed to expose an inner housing 2502. FIG. 26 is an exploded view of the inner housing 2502 and associated electrical components illustrated in FIG. 25. Referring to FIG. 25 and FIG. 26, the inner housing 2502 is contained within the housing 600a and is mounted to the lower housing 608a. The inner housing 2502 contains a sensor mount 912 with a first detection well 908, a second detection well 910, and a light source well 902 formed therethrough. The first light detector 222 is mounted within the first detection well 908 and the second light detector 224 is mounted within the second detection well 910. The first and second light sources 218/220 are mounted within the light source well 902. In an aspect, the first detection well 908, second detection well 910, and light source well 902 of the sensor mount 912 are optically isolated from one another to ensure that light from the light sources 218/220 does not reach the light detectors 222/224 without coupling through the skin of the patient 202. The separation between the two detection wells 908/910 ensures that the detected fluorescence signal from the exogenous fluorescent agent is distinguishable from the unfiltered excitation light, as described in detail above.

Referring to FIG. 26, the inner housing 2502 includes a first detection aperture 2602, second detection aperture 2604, and light source aperture 2606. The sensor mount 912 is coupled to the inner housing 2502 so that the first detection aperture 2602, second detection aperture 2604, and light source aperture 2606 are aligned with the first detection well 908, second detection well 910, and light source well 902 of the sensor mount 912, respectively.

In one aspect, optically transparent windows 2610, 2612, and 2614 are coupled within first detection aperture 2602, second detection aperture 2604, and light source aperture 2606, respectively, to seal the apertures while also providing optically transparent conduits between the tissues and the interior of the sensor head 204a. In addition, diffusers 2616, 2618, and 2620 are coupled over optically transparent windows 2610, 2612, and 2614, respectively. The diffusers 2616, 2618, and 2620 are provided to spatially homogenize light delivered to the tissues by light sources 218/220 and to spatially homogenize light detected by light detectors 222/224. In an aspect, the absorption filter 244 is coupled to the diffuser 2616. In one aspect, an optically transparent adhesive is used to couple the absorption filter 244 is coupled to the diffuser 2616.

In view of the above, it will be seen that the several advantages of the disclosure are achieved and other advantageous results attained. As various changes could be made in the above methods and systems without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method of monitoring a time-varying fluorescence emitted from a fluorescent agent from within a diffuse reflecting medium with time-varying optical properties, the method comprising:
providing a measurement data set comprising a plurality of measurement entries, each measurement data entry comprising at least two measurements obtained at one data acquisition time from a patient before and after administration of the fluorescent agent, the at least two measurements comprising an $Flr_{meas}$ (fluorescence emission) signal detected at a third region adjacent to the diffuse reflecting medium by a filtered light detector during illumination of the diffuse reflecting medium by excitatory-wavelength light from the first region, and at least one DR (diffuse reflection) signal selected from:
a $DRex_{meas}$ signal detected at a second region adjacent to the diffuse reflecting medium by an unfiltered light detector during illumination of the diffuse reflecting medium by excitatory-wavelength light from a first region adjacent to the diffuse reflecting medium;
a $DR_{em}$ signal detected at the second region by the unfiltered light detector during illumination of the diffuse reflecting medium by emission-wavelength light from the first position; and
a $DR_{em,filtered}$ signal detected at the third region by the filtered light detector during illumination of the diffuse reflecting medium by emission-wavelength light from the first position; and;
identifying a post-agent-administration portion of the measurement data set;
transforming the $Flr_{meas}$ signal of each measurement data entry within the post-agent-administration portion of the measurement data set to an $IF_{agent}$ (intrinsic fluorescence) signal representing a detected fluorescence intensity emitted solely by the fluorescent agent from within the diffuse reflecting medium, wherein the transforming comprises at least one of removing the effects of leak-through of excitation-level light into the $Flr_{meas}$ signal and removing the autofluorescence contribution to the $Flr_{meas}$ signal; and
monitoring the $IF_{agent}$ signal for each measurement data entry within the post-agent-administration portion of the measurement data set.

2. The method of claim 1, wherein removing the effects of leak-through of excitation-level light into the $Flr_{meas}$ signal comprises transforming the $DRex_{meas}$ signal into an ExLT (excitation-wavelength light leak-through) signal representing a level of excitation-wavelength light leak using the equation:

$$ExLT = C_{ExLT} * DR_{ex_{meas}}$$

where $C_{ExLT}$ is a calibration factor.

3. The method of claim 2, wherein removing the effects of leak-through of excitation-level light into the $Flr_{meas}$ signal further comprises transforming the $Flr_{meas}$ signal into a corrected fluorescence signal $Flr_{photons}$, representing detected emission-wavelength fluorescence only, using the equation:

$$Flr_{photons} = Flr_{meas} - ExLT.$$

4. The method of claim 3, wherein removing the effects of autofluorescence comprises determining $IF_{auto}$, representing intrinsic autofluorescence emitted by chromophores within the diffuse reflecting medium in addition to the fluorescent agent, by replacing the $Flr_{photons}$ signals obtained prior to administration of the fluorescent agent with a central value selected from the group consisting of mean, median, mode, and trimmed mean.

5. The method of claim 4, wherein removing the effects of autofluorescence further comprises subtracting $IF_{auto}$ from $Flr_{photons}$ to obtain the $IF_{agent}$ signal.

6. The method of claim 2, wherein $C_{ExLT}$ is obtained by:
obtaining measurements from a solid phantom, the measurements comprising:
the fluorescence signal $Flr_{meas}$ representing emission-wavelength fluorescence measured using the filtered light detector;
the excitation-wavelength light signal $DRex_{meas}$ measured using the non-filtered light detector; and
computing $C_{ExLT}$ using the equation:

$$C_{ExLT} = \frac{Flr_{meas}}{DR_{ex_{meas}}}.$$

7. A method of determining renal function in a patient, the method comprising:
   providing a measurement data set comprising a plurality of measurement entries, each measurement data entry comprising at least two measurements obtained at a corresponding data acquisition time from a tissue of a patient before and after administration of an exogenous fluorescent agent, the at least two measurements comprising an $Flr_{meas}$ (fluorescence emission) signal detected at a third region adjacent to the diffuse reflecting medium by a filtered light detector during illumination of the diffuse reflecting medium by excitatory-wavelength light from the first region, and at least one DR (diffuse reflection) signal selected from:
      a $DRex_{meas}$ signal detected at a second region adjacent to the diffuse reflecting medium by an unfiltered light detector during illumination of the diffuse reflecting medium by excitatory-wavelength light from a first region adjacent to the diffuse reflecting medium;
      the $Flr_{meas}$ signal detected at a third region adjacent to the diffuse reflecting medium by a filtered light detector during illumination of the diffuse reflecting medium by excitatory-wavelength light from the first region;
      a $DR_{em}$ signal detected at the second region by the unfiltered light detector during illumination of the diffuse reflecting medium by emission-wavelength light from the first position; and
      a $DR_{em,filtered}$ signal detected at the third region by the filtered light detector during illumination of the diffuse reflecting medium by emission-wavelength light from the first position;
   transforming the $Flr_{meas}$ signal of each measurement data entry within the post-agent-administration portion of the measurement data set to an $IF_{agent}$ (intrinsic fluorescence) signal representing a detected fluorescence intensity emitted solely by the fluorescent agent from within the diffuse reflecting medium, wherein transforming the $Flr_{meas}$ signal comprises at least one of removing the effects of leak-through of excitation-level light into the $Flr_{meas}$ signal and removing the autofluorescence contribution to the $Flr_{meas}$ signal;
   identifying a post-equilibration portion of the measurement data set;
   transforming the $IF_{agent}$ signals corresponding to the post-equilibration portion of the measurement data set to a rate of change of the $IF_{agent}$ signals; and
   transforming
   determining the renal function in the patient based on the rate of change of the $IF_{agent}$ signals.

8. The method of claim 7, wherein removing the effects of leak-through of excitation-level light into the $Flr_{meas}$ signal comprises transforming each the $DRex_{meas}$ signal into an ExLT (excitation-wavelength light leak-through) signal representing a level of excitation-wavelength light leak-through using the equation:

$$ExLT = C_{ExLT} * DR_{ex_{meas}}$$

where $C_{ExLT}$ is a calibration factor.

9. The method of claim 8, wherein removing the effects of leak-through of excitation-level light into the $Flr_{meas}$ signal further comprises transforming the $Flr_{meas}$ signal into a corrected fluorescence signal $Flr_{photons}$, representing detected emission-wavelength fluorescence only, using the equation:

$$Flr_{photons} = F_{meas} - ExLT.$$

10. The method of claim 9, wherein removing the effects of autofluorescence comprises determining $IF_{auto}$, representing intrinsic autofluorescence emitted by chromophores within the diffuse reflecting medium in addition to the fluorescent agent, by determining a central value of the $Flr_{photons}$ signals over a portion of the measurement dataset obtained prior to administration of the fluorescent agent, the central value selected from the group consisting of mean, median, mode, and trimmed mean.

11. The method of claim 10, wherein removing the effects of autofluorescence further comprises subtracting $IF_{auto}$ from $Flr_{photons}$ to obtain the $IF_{agent}$ signal.

12. The method of claim 8, wherein $C_{ExLT}$ is obtained by:
   obtaining measurements from a solid phantom, the measurements comprising:
      the fluorescence signal $Flr_{meas}$ representing emission-wavelength fluorescence measured using the filtered light detector;
      the excitation-wavelength light signal $DRex_{meas}$ measured using the non-filtered light detector; and
      computing $C_{ExLT}$ using the equation:

$$C_{ExLT} = \frac{Flr_{meas}}{DR_{ex_{meas}}}.$$

13. The method of claim 4, wherein replacing the $Flr_{photons}$ signals obtained prior to administration of the fluorescent agent with a central value comprises transforming the $Flr_{photons}$ signals obtained prior to administration of the fluorescent agent using the equation:

$$IF_{Auto} = \text{median}(Flr_{photons}(1:\text{endBackground}))$$

wherein (1:endBackground) represents a portion of the measurement dataset obtained prior to administration of the fluorescent agent.

14. The method of claim 7, wherein transforming the $IF_{agent}$ signals corresponding to the post-equilibration portion of the measurement data set to the rate of change of the $IF_{agent}$ signals comprises:
   performing a single-exponent curve-fit of the $IF_{agent}$ signals according to the equation:

$$IF_{post\text{-}equilibration} C_0 + C_1 e^{-t/\tau}$$

where $IF_{post\text{-}equilibration}$ represents $IF_{agent}$ signals corresponding to the post-equilibration portion of the measurement data set, C0 and C1 are curve-fit constants, t is time, and $\tau$ is a time constant; and
   assigning the time constant r as the renal decay time constant (RDTC), wherein RDTC represents the rate of change of the $IF_{agent}$ signals.

15. The method of claim 7, wherein transforming the $IF_{agent}$ signals corresponding to the post-equilibration portion of the measurement data set to the rate of change of the $IF_{agent}$ signals comprises:
   log-transforming the $IF_{agent}$ signals at each corresponding data acquisition time;
   performing a linear regression of the log-transformed $IF_{agent}$ signals as a function of the corresponding data acquisition time to obtain a slope;
   inverting the slope to obtain the RDTC, wherein RDTC represents the rate of change of the $IF_{agent}$ signals.

16. The method of claim 10, wherein determining $IF_{auto}$ by determining a central value of the $Flr_{photons}$ signals comprises determining $IF_{auto}$ using the equation:

$$IF_{Auto} = \text{median}(Flr_{photons}(1:\text{endBackground}))$$

wherein (1:endBackground) represents a portion of the measurement dataset obtained prior to administration of the fluorescent agent.

\* \* \* \* \*

UNITED STATES PATENT AND TRADEMARK OFFICE
CERTIFICATE OF CORRECTION

| | |
|---|---|
| PATENT NO. | : 10,194,854 B2 |
| APPLICATION NO. | : 15/884371 |
| DATED | : February 5, 2019 |
| INVENTOR(S) | : Keating et al. |

Page 1 of 1

It is certified that error appears in the above-identified patent and that said Letters Patent is hereby corrected as shown below:

In the Claims

Column 55, Claim 1, Line 63, delete "the" and insert therefor --a--.

Column 56, Claim 1, Line 1, delete "a" and insert therefor --the--.

Column 56, Claim 1, Line 6, delete "position" and insert therefor --region--.

Column 56, Claim 1, Line 10, delete "position" and insert therefor --region--.

Column 57, Claim 7, Line 13, delete "the" and insert therefor --a--.

Column 57, Claim 7, Line 18, delete "a" and insert therefor --a--.

Column 57, Claim 7, Lines 20-24, delete "the Flrmeas signal detected at a third region adjacent to the diffuse reflecting medium by a filtered light detector during illumination of the diffuse reflecting medium by excitatory-wavelength light from the first region;".

Column 57, Claim 7, Line 28, delete "position" and insert therefor --region--.

Column 57, Claim 7, Line 32, delete "position" and insert therefor --region--.

Column 57, Claim 9, Line 67, delete "Fmeas" and insert therefor --Flrmeas--.

Signed and Sealed this
Twentieth Day of December, 2022

Katherine Kelly Vidal
*Director of the United States Patent and Trademark Office*